US008438043B2

(12) United States Patent
Nagaeda

(10) Patent No.: US 8,438,043 B2
(45) Date of Patent: May 7, 2013

(54) NURSING INFORMATION MANAGEMENT METHOD AND NURSING INFORMATION MANAGEMENT APPARATUS FOR MANAGING NURSING ACTIONS

(75) Inventor: Tsuyoshi Nagaeda, Tokyo (JP)

(73) Assignee: Olympus Medical Systems Corp., Tokyo (JP)

( * ) Notice: Subject to any disclaimer, the term of this patent is extended or adjusted under 35 U.S.C. 154(b) by 1286 days.

(21) Appl. No.: 11/787,120

(22) Filed: Apr. 13, 2007

(65) Prior Publication Data

US 2007/0244723 A1 Oct. 18, 2007

(30) Foreign Application Priority Data

Apr. 13, 2006 (JP) ................................ 2006-111358

(51) Int. Cl.
*G06Q 50/00* (2006.01)

(52) U.S. Cl.
USPC .................................................. 705/3; 705/2

(58) Field of Classification Search .................. 705/2-3
See application file for complete search history.

(56) References Cited

U.S. PATENT DOCUMENTS

| | | | | |
|---|---|---|---|---|
| 6,523,009 | B1 * | 2/2003 | Wilkins | 705/3 |
| 7,089,247 | B2 * | 8/2006 | Kloos et al. | 1/1 |
| 2003/0149597 | A1 * | 8/2003 | Zaleski | 705/2 |
| 2003/0225597 | A1 * | 12/2003 | Levine | 705/3 |
| 2004/0117215 | A1 * | 6/2004 | Marchosky | 705/3 |

FOREIGN PATENT DOCUMENTS

| | | |
|---|---|---|
| EP | 1 365 344 A2 | 11/2003 |
| JP | 2001-052056 A | 2/2001 |
| JP | 2003-331055 A | 11/2003 |
| JP | 2004-110818 | 4/2004 |
| JP | 2005-165513 A | 6/2005 |
| JP | 2006-133910 | 5/2006 |
| WO | WO 99/33390 | 7/1999 |
| WO | WO 02/086655 A3 | 10/2002 |

OTHER PUBLICATIONS

Japanese Office Action dated Jan. 31, 2012 issued in counterpart Japanese Patent Application No. 2006-111358.

Official Action, dated Mar. 22, 2011, from the Japan Patent Office in counterpart Japanese Patent Application No. 2006-111358, together with a partial English language translation.

* cited by examiner

*Primary Examiner* — Gerald J. O'Connor
*Assistant Examiner* — Sind Phongsvirajati
(74) *Attorney, Agent, or Firm* — Scully, Scott, Murphy & Presser, P.C.

(57) ABSTRACT

In cooperation with a first database, a problem preparation supporting unit supports the preparation of nursing problem items for patients. Based on the nursing problem items prepared, a plan preparation supporting unit supports the preparation of nursing care plans by conducting search through a second database. In cooperation with a third database, a specification unit specifies an implementation of nursing items contained in the prepared nursing care plan. When a communication unit receives an implementation result of the nursing items, the communication unit outputs the result to a recording unit. A nurse enters an evaluation of the implementation result of the nursing items to an operation apparatus. The evaluation entered is recorded in the recording unit. Among the nursing problem items stored in the recording unit, the nursing items contained in the nursing care plans, the implementation results and the evaluations, the management unit associates them with one another by bringing them into correspondence with each other.

10 Claims, 56 Drawing Sheets

PATIENT ID :1234567
PATIENT NAME:TARO TOKYO

| ID NO. (100) | NURSING PROBLEM (102) | NURSING CARE PLAN (104) | IMPLEMENTATION RESULT (106) | NURSING RECORD (108) | VARIANCE FACTOR (110) |
|---|---|---|---|---|---|
| #1 | THERE IS A RISK OF SUFFERING FROM A HEMORRHAGIC SHOCK DUE TO HEMATEMESIS OR MELENA | (OP)<br>① VITAL SIGN<br>⋮ | BODY TEMPERATURE: 36.5 °C<br>⋮ | [S]···<br>[O]···<br>[A]···<br>[P]··· | |
| #2 | THERE IS A POSSIBILITY THAT WATER BALANCE IS DISRUPTED BY THE LACK OF BLOOD | (OP)<br>⋮ | AMOUNT OF HEMATEMESIS: 50cc | [S]···<br>[O]···<br>[A]···<br>[P] | PATIENT/FAMILY (+) |
| #N | ··· | ··· | ··· | ··· | |

| PATIENT ID (112) | PATIENT NAMES (114) | SEX (116) | AGE (118) | ADMISSION DATE (120) | EXPECTED DISCHARGE DATE (122) | HOSPITAL DAYS (124) | COMMENTS (126) |
|---|---|---|---|---|---|---|---|
| 100001 | TARO KYOTO | M | 19 YEARS AND 6 MONTHS OLD | 2003/12/01 | 2003/12/21 | 12 DAYS | |
| 100002 | SABURO SHIGA | M | 22 YEARS AND 4 MONTHS OLD | 2003/12/02 | 2003/12/30 | 11 DAYS | |
| ... | ... | ... | ... | ... | ... | ... | ... |

60

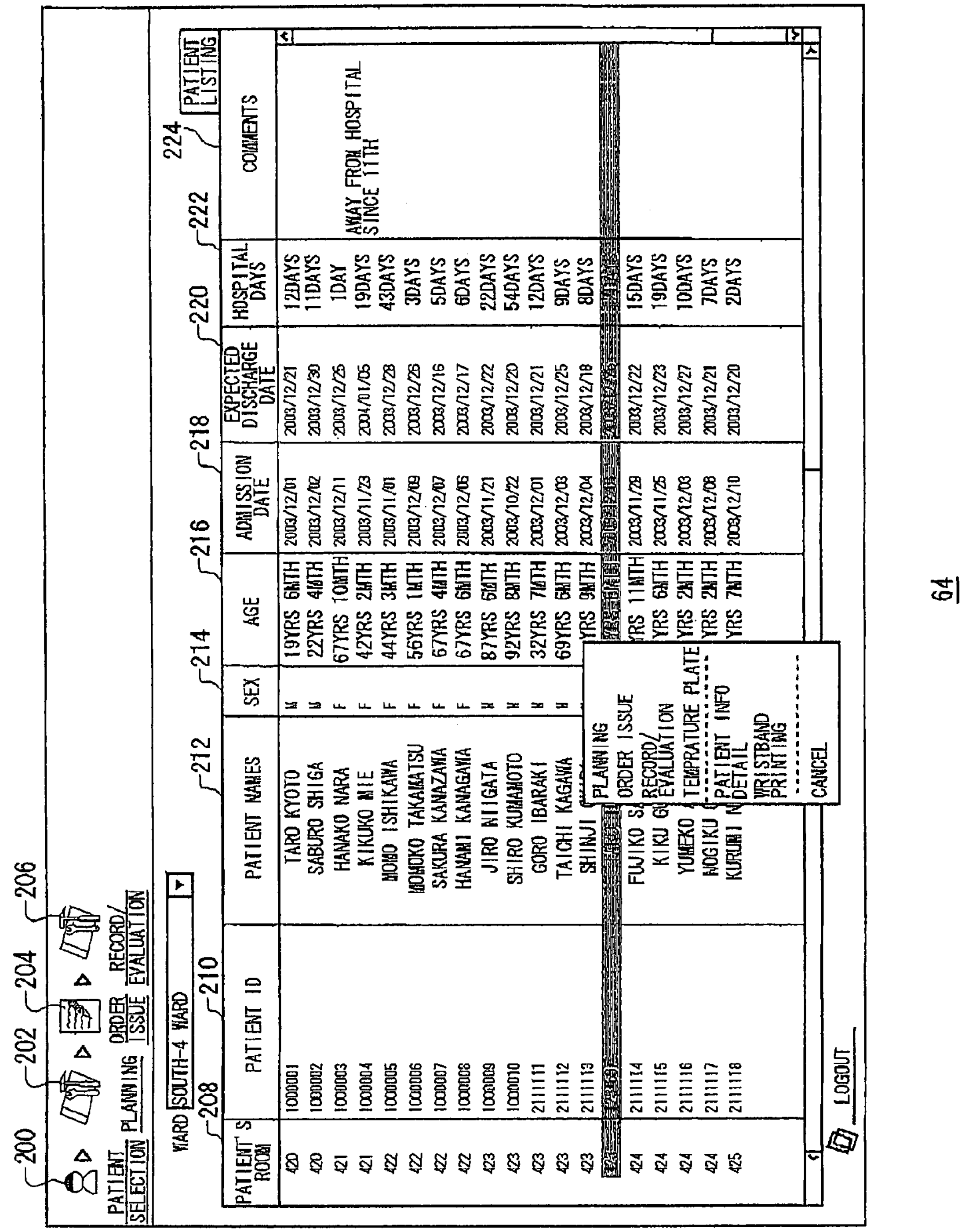

FIG.7

| PATIENT'S ROOM | PATIENT ID | PATIENT NAMES | SEX | AGE | ADMISSION DATE | EXPECTED DISCHARGE DATE | HOSPITAL DAYS | COMMENTS |
|---|---|---|---|---|---|---|---|---|
| 420 | 1000001 | TARO KYOTO | M | 19YRS 6MTH | 2003/12/01 | 2003/12/21 | 12DAYS | |
| 420 | 1000002 | SABURO SHIGA | M | 22YRS 4MTH | 2003/12/02 | 2003/12/30 | 11DAYS | |
| 421 | 1000003 | HANAKO NARA | F | 67YRS 10MTH | 2003/12/11 | 2003/12/25 | 1DAY | |
| 421 | 1000004 | KIKUKO MIE | F | 42YRS 2MTH | 2003/11/23 | 2004/01/05 | 19DAYS | |
| 421 | 1000005 | MOMO ISHIKAWA | F | 44YRS 3MTH | 2003/11/01 | 2003/12/28 | 43DAYS | |
| 422 | 1000006 | MOMOKO TAKAMATSU | F | 56YRS 1MTH | 2003/12/09 | 2003/12/26 | 3DAYS | AWAY FROM HOSPITAL SINCE 11TH |
| 422 | 1000007 | SAKURA KANAZAWA | F | 67YRS 4MTH | 2003/12/07 | 2003/12/16 | 5DAYS | |
| 422 | 1000008 | HANAMI KANAGAWA | F | 67YRS 6MTH | 2003/12/06 | 2003/12/17 | 6DAYS | |
| 423 | 1000009 | JIRO NIIGATA | M | 87YRS 5MTH | 2003/11/21 | 2003/12/22 | 22DAYS | |
| 423 | 1000010 | SHIRO KUMAMOTO | M | 92YRS 6MTH | 2002/10/22 | 2003/12/20 | 54DAYS | |
| 423 | 2111111 | TAICHI KAGAWA | M | 32YRS 7MTH | 2003/12/01 | 2003/12/21 | 12DAYS | |
| 423 | 2111112 | SHINJI | M | 69YRS 9MTH | 2003/12/04 | 2003/12/18 | 9DAYS | |
| 423 | 2111113 | | | | | | 8DAYS | |
| 424 | 2111114 | FUJIKO | | YRS 11MTH | 2003/11/29 | 2003/12/22 | 15DAYS | |
| 424 | 2111115 | KIKU G | | YRS 6MTH | 2003/11/25 | 2003/12/23 | 19DAYS | |
| 424 | 2111116 | YUMEKO | | YRS 2MTH | 2003/12/03 | 2003/12/27 | 10DAYS | |
| 424 | 2111117 | NOGIKU | | YRS 2MTH | 2003/12/08 | 2003/12/21 | 7DAYS | |
| 425 | 2111118 | KURUMI | | YRS 7MTH | 2003/12/10 | 2003/12/20 | 2DAYS | |

Popup menu:
- PLANNING
- ORDER ISSUE
- RECORD/EVALUATION
- TEMPERATURE PLATE
- PATIENT INFO DETAIL
- WRISTBAND PRINTING
- CANCEL

PATIENT SELECTION — PLANNING — ORDER ISSUE — RECORD/EVALUATION

WARD SOUTH-4 WARD

PATIENT LISTING

LOGOUT

FIG.8

| DEPARTMENT (130) | DISEASE (132) | NURSING PROBLEM (134) | NURSING PROBLEM CODE (136) |
|---|---|---|---|
| GASTROENTEROLOGY | ESOPHAGITIS | . . . . | 0001 . . . |
| | COLON CANCER | THERE IS A RISK OF SUFFERING FROM A HEMORRHAGIC SHOCK DUE TO HEMATEMESIS OR MELENA | 1000 |
| | | . . . | . . . |
| | | THERE IS A POSSIBILITY THAT WATER BALANCE IS DISRUPTED BY BLOOD LOSS | 1XXX |
| PEDIATRICS | . . . | . . . . | 9000 . . . 9XXX |

| 140 NURSING PROBLEM CODE | 142 TARGET | 144 PLAN |
| --- | --- | --- |
| 1000 | FIND THE BLEEDING IN EARLY STAGES AND PREVENT A CRITICAL SHOCK STATE<br>◆ FROM WHEN BLEEDING STARTS FROM ESOPHAGEAL VARIX UNTIL ARREST OF BLEEDING IS VERIFIED | (OP)<br>① VAITAL SIGN<br>1)BP<br>2)PULSE<br>. . .<br>(CP)<br>① SECURE BLOOD VESSEL, EMERGENCY CART, PREPARATION OF A MONITOR<br>. . .<br>(EP)<br>① NECESSITY OF BED REST DEPENDING ON MENTAL STATUS |
| 9XXX | . . . | . . . |

| ITEM | VARIATION |
|---|---|
| BODY TEMPERATURE | GREATER THAN 1°C |
| URINE VOLUME | GREATER THAN 50 cc |
| PULSE | GREATER THAN 10 |

| VARIANCE | FACTORS | # OF TIMES |
|---|---|---|
| + | PATIENT/FAMILY | 13 |
| | MEDICAL STAFF MEMBER | 50 |
| | SYSTEM | 11 |
| | OTHER | 4 |
| − | PATIENT/FAMILY | 6 |
| | MEDICAL STAFF MEMBER | 10 |
| | SYSTEM | 48 |
| | OTHER | 2 |

58

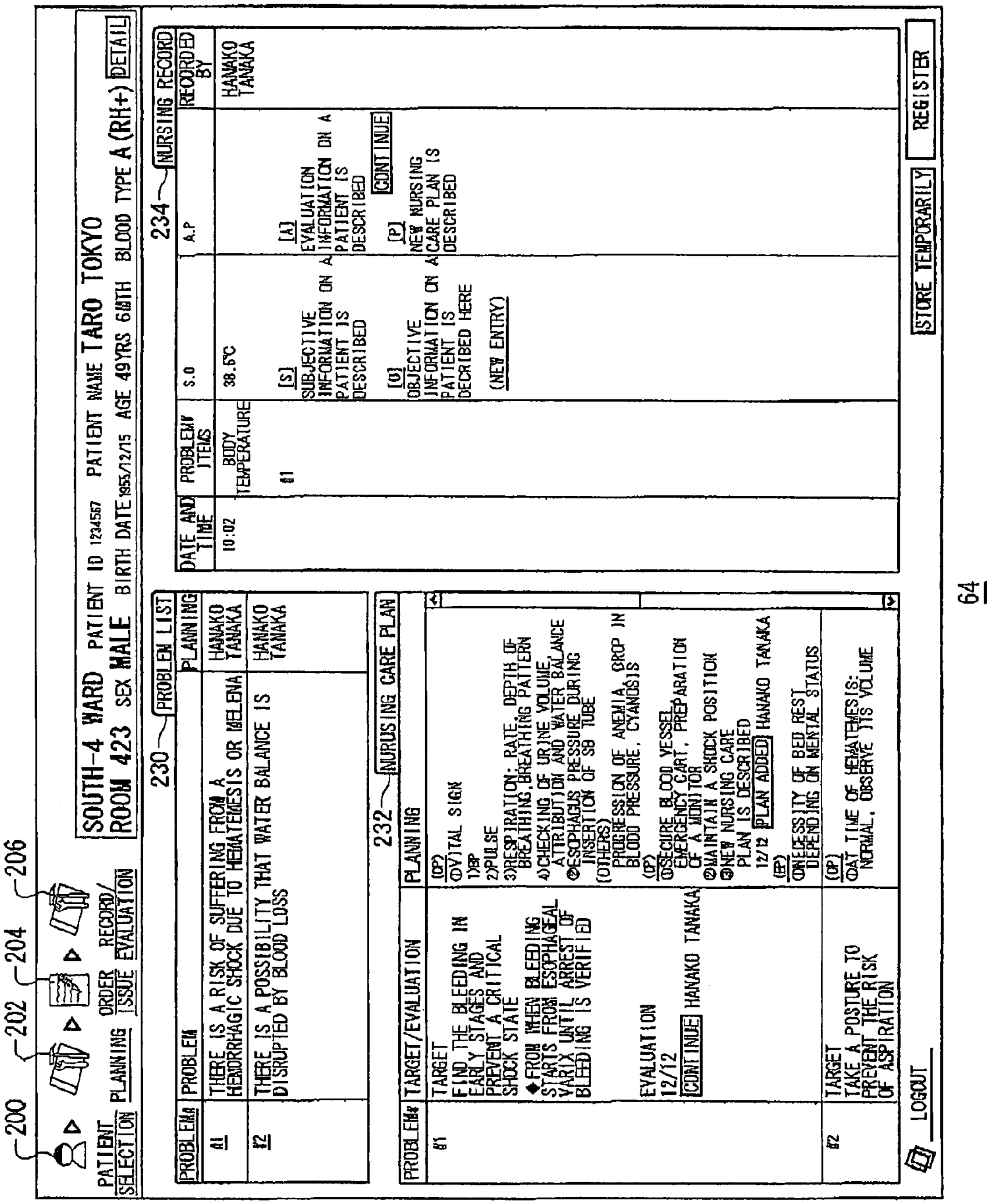

FIG.38

| PATIENT SELECTION | PLANNING | ORDER ISSUE | RECORD/ EVALUATION | | | | |
|---|---|---|---|---|---|---|---|

SOUTH-4 WARD   PATIENT ID 1234567   PATIENT NAME TARO TOKYO
ROOM 423   SEX MALE   BIRTH DATE 1955/12/15   AGE 49YRS 6MTH   BLOOD TYPE A (RH+) [DETAIL]

230 — [PROBLEM LIST]

| PROBLEM# | PROBLEM | PLANNING |
|---|---|---|
| #1 | THERE IS A RISK OF SUFFERING FROM A HEMORRHAGIC SHOCK DUE TO HEMATEMESIS OR MELENA | HANAKO TANAKA |
| #2 | THERE IS A POSSIBILITY THAT WATER BALANCE IS DISRUPTED BY BLOOD LOSS | HANAKO TANAKA |

232 — [NURUSING CARE PLAN]

| PROBLEM# | TARGET/EVALUATION | PLANNING |
|---|---|---|
| #1 | TARGET<br>FIND THE BLEEDING IN EARLY STAGES AND PREVENT A CRITICAL SHOCK STATE<br>◆FROM WHEN BLEEDING STARTS FROM ESOPHAGEAL VARIX UNTIL ARREST OF BLEEDING IS VERIFIED<br>EVALUATION 12/12<br>[CONTINUE] HANAKO TANAKA | (OP)<br>①VITAL SIGN<br>1)BP<br>2)PULSE<br>3)RESPIRATION: RATE, DEPTH OF BREATHING, BREATHING PATTERN<br>4)CHECKING OF URINE VOLUME, ATTRIBUTION AND WATER BALANCE<br>⑤ESOPHAGUS PRESSURE DURING INSERTION OF SB TUBE<br>(OTHERS)<br>⑥PROGRESSION OF ANEMIA, DROP IN BLOOD PRESSURE, CYANOSIS<br>(CP)<br>①SECURE BLOOD VESSEL<br>②PREPARATION OF EMERGENCY CART, PREPARATION OF A MONITOR<br>③MAINTAIN A SHOCK POSITION<br>④NEW NURSING CARE<br>PLAN IS DESCRIBED<br>12/12 [PLAN ADDED] HANAKO TANAKA<br>(EP)<br>①NECESSITY OF BED REST DEPENDING ON MENTAL STATUS |
| #2 | TARGET<br>TAKE A POSTURE TO PREVENT THE RISK OF ASPIRATION | (OP)<br>①AT TIME OF HEMATEMESIS: NORMAL, OBSERVE ITS VOLUME |

234 — [NURSING RECORD]

| DATE AND TIME | PROBLEM ITEMS | S.O | A.P | RECORDED BY |
|---|---|---|---|---|
| 10:02 | BODY TEMPERATURE<br>#1 | 38.5°C<br>[S]<br>SUBJECTIVE INFORMATION ON PATIENT IS DESCRIBED<br>[O]<br>OBJECTIVE INFORMATION ON PATIENT IS DECRIBED HERE<br>(NEW ENTRY) | [A]<br>EVALUATION INFORMATION ON A PATIENT IS DESCRIBED [CONTINUE]<br>[P]<br>NEW NURSING CARE PLAN IS DESCRIBED | HANAKO TANAKA |

[STORE TEMPORARILY]   [REGISTER]

LOGOUT

FIG.40

| | SELECTABILITY OF PER DEPARTMENT | SELECTABILITY OF PER DISEASE | SELECTABILITY OF PER PROBLEM |
|---|---|---|---|
| IF PER HOSPIALIZAION IS SELECTED IN UNITS OF VARIANCE ENTRY | NOT SELECTABLE | NOT SELECTABLE | NOT SELECTABLE |
| IF PER DEPARTMENT IS SELECTED IN UNITS OF VARIANCE ENTRY | SELECTABLE | NOT SELECTABLE | NOT SELECTABLE |
| IF PER DISEASE IS SELECTED IN UNITS OF VARIANCE ENTRY | SELECTABLE | SELECTABLE | NOT SELECTABLE |
| IF PER PROBLEM IS SELECTED IN UNITS OF VARIANCE ENTRY | SELECTABLE | SELECTABLE | SELECTABLE |

STATISTICAL CHART OF VARIANCES
DEPATMENT TO BE CONSIDERED: GASTROINTESTINAL MEDICINE
PERIOD COVERED: APRIL 1, 2004 TO SEPTEMBER 30, 2004 OUTPUT DATE: OCTOBER 10, 2004 1/5PAGE

| PATIENT NAME | PROBLEM NUMBER | PROBLEM | NEGATIVE | POSITIVE | TOTAL |
|---|---|---|---|---|---|
| NURSING CARE OF A PATIENT WITH ESOPHAGEAL DISEASE | CP1 | OBSTRUCTION,HOARSENESS, BLEEDING, PERFORATION, BRONCHOPLEURAL FISTULA | 111 | 6 | 117 |
| | #1 | ANXIETY | 4 | 34 | 38 |
| | #2 | ABNORMAL NUTRIENT INTAKE/CONSUMPTION:BELOW REQUIREMENT | 42 | 3 | 45 |
| NURSING CARE OF A PATIENT WITH ESOPHAGEAL VARIX RUPTURE | CP1 | REBLEEDING | 10 | 1 | 11 |
| | #1 | ANXIETY | 11 | 2 | 13 |
| NURSING CARE OF A PATIENT RECEIVING EIS | CP1 | BLEEDING, ESOPHAGEAL ULCER, PERFORATION | 12 | 3 | 15 |
| | #1 | COMFORT DISORDER. ACUTE PAIN | 8 | 1 | 9 |
| | #2 | ANXIETY | 6 | 3 | 9 |
| NURSING CARE OF A PATIENT RECEIVING ERCP | CP1 | ACUTE PANCREATITIS, | 8 | 1 | 9 |
| | #1 | ANXIETY | 4 | 4 | 8 |
| NURSING CARE OF A PATIENT RECEIVING EST | CP1 | ACUTE PANCREATITIS, BLEEDING, PERFORATION | 5 | 0 | 5 |
| | #1 | ANXIETY | 11 | 2 | 13 |
| NURSING CARE OF A PATIENT RECEIVING PTCCD | CP1 | PERITONITIS, HEMOPERITONEUM, INFECTION | 7 | 3 | 10 |
| | #1 | SELF-CARE DEFICIT SYNDROME | 9 | 1 | 10 |
| | #2 | ANXIETY | 4 | 2 | 6 |
| | #3 | COMFORT DISORDER. ACUTE PAIN | 8 | 1 | 9 |
| NURSING CARE OF A PATIENT WITH GALLSTONE | CP1 | ACUTE CHOLECYSTITIS, PERITONITIS, SHOCK | 9 | 3 | 12 |
| | #1 | ANXIETY | 3 | 1 | 4 |
| NUURSING CARE OF A PATIENT WITH ACUTE PANCREATITIS | CP1 | SHOCK, DIC, HYPERGLYCEMIA, | 8 | 2 | 10 |
| | #1 | COMFORT DISORDER. ACUTE PAIN | 4 | 5 | 9 |

FIG.44

EVALUATION LISTING PER VARIANCE

DISEASE: NURSING CARE OF A PATIENT WHO UNDERGOES GASTRECTOMY
DESCRIPTION OF PROBLEMS: OBSTRUCTION, HOARSENESS, BLEEDING, PERFORATION, BRONCHOPLEURAL FISTULA
TYPE: NEGATIVE VARIANCE NUMBER OF ITEMS: TOTAL:233 HIT:111
PERIOD COVERED: APRIL 1, 2004 TO SEPTEMBER 30, 2004 WARD: WARD 4
OUTPUT DATE: OCTOBER 10, 2004 1/5 PAGE

| DATE AND TIME OF EVALUATION | EVALUATION CONTENTS [A] | EVALUATED BY (NURSE NAME) |
|---|---|---|
| 2004/9/28 | DISCREPANCY IN VITAL VALUES | HANAKO KANGO |
| 2004/9/28 | SURGERY RESERVATION FULLY BOOKED | TARO KANGO |
| 2004/9/28 | PATIENT DENIED | TARO KANGO |
| 2004/9/28 | SURGERY RESERVATION FULLY BOOKED | TARO KANGO |
| 2004/9/28 | SURGERY RESERVATION FULLY BOOKED | HANAKO KANGO |
| 2004/9/28 | SURGERY RESERVATION FULLY BOOKED | TARO KANGO |
| 2004/9/28 | PATIENT DENIED | TARO KANGO |
| 2004/9/28 | DISCREPANCY IN VITAL VALUES | TARO KANGO |
| 2004/9/28 | DISCREPANCY IN VITAL VALUES | TARO KANGO |
| 2004/9/28 | SURGERY RESERVATION FULLY BOOKED | HANAKO KANGO |
| 2004/9/28 | SURGERY RESERVATION FULLY BOOKED | TARO KANGO |
| 2004/9/28 | SURGERY RESERVATION FULLY BOOKED | HANAKO KANGO |
| 2004/9/28 | DISCREPANCY IN VITAL VALUES | TARO KANGO |
| 2004/9/28 | DISCREPANCY IN VITAL VALUES | HANAKO KANGO |
| 2004/9/28 | SURGERY RESERVATION FULLY BOOKED | HANAKO KANGO |
| 2004/9/28 | SURGERY RESERVATION FULLY BOOKED | TARO KANGO |
| 2004/9/28 | SURGERY RESERVATION FULLY BOOKED | HANAKO KANGO |
| 2004/9/28 | SURGERY RESERVATION FULLY BOOKED | HANAKO KANGO |
| 2004/9/28 | SURGERY RESERVATION FULLY BOOKED | TARO KANGO |
| 2004/9/28 | SURGERY RESERVATION FULLY BOOKED | HANAKO KANGO |

FIG.46A

| | |
|---|---|
| #1 | INSOMNIA |
| #2 | ANXIETY |
| CP1 | PAIN AND COMPLICATION RESULTING FROM SURGERY |
| #3 | CHANGE IN DIETARY CONSTITUENT |

FIG.46B

| | |
|---|---|
| CP1 | PAIN AND COMPLICATION RESULTING FROM SURGERY |
| #1 | INSOMNIA |
| #2 | ANXIETY |
| #3 | CHANGE IN DIETARY CONSTITUENT |

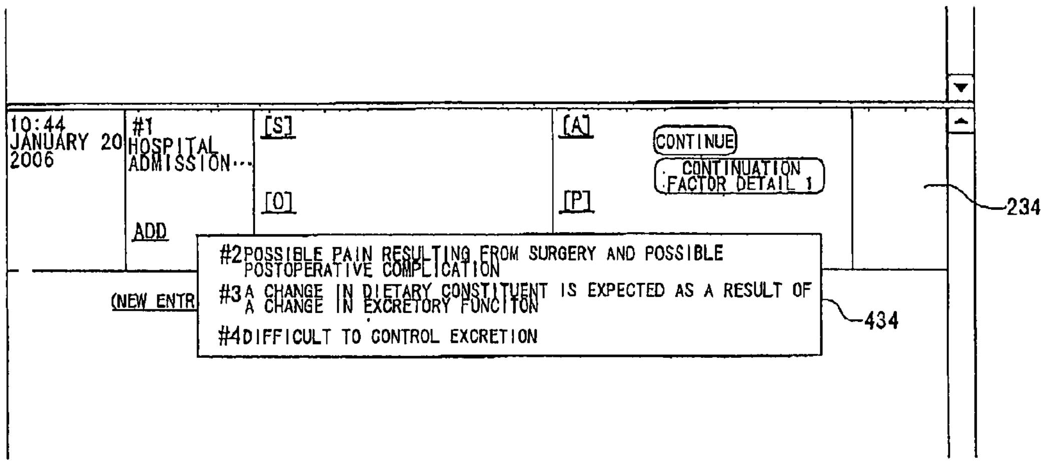

FIG.48A

| 10:44 JANUARY 20 2006 | #1 HOSPITAL ADMISSION··· | [S] | | [A] | CONTINUE |
| | | [O] | | [P] | CONTINUATION FACTOR DETAIL 1 |
| | ADD | | | | |

#2 POSSIBLE PAIN RESULTING FROM SURGERY AND POSSIBLE POSTOPERATIVE COMPLICATION
#3 A CHANGE IN DIETARY CONSTITUENT IS EXPECTED AS A RESULT OF A CHANGE IN EXCRETORY FUNCITON
#4 DIFFICULT TO CONTROL EXCRETION (NEW ENTRY)

—234
—434

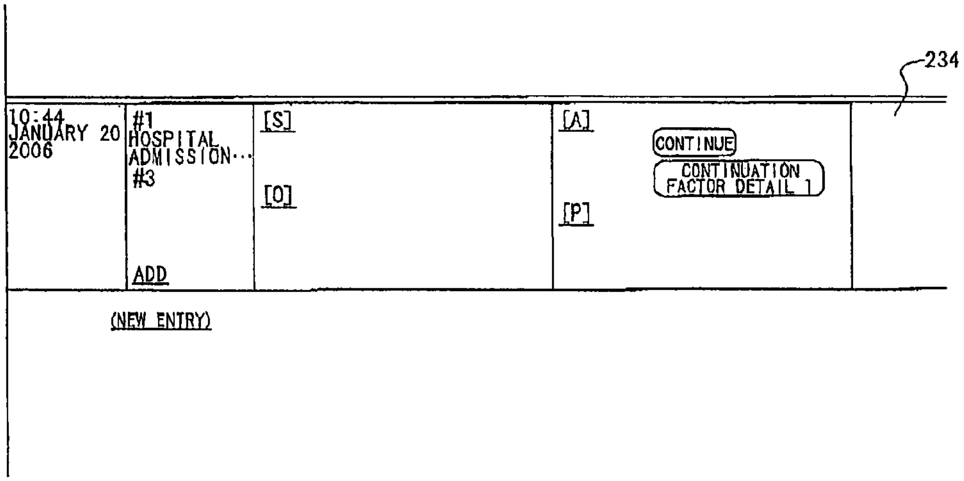

| 10:44 JANUARY 20 2006 | #1 HOSPITAL ADMISSION··· #3 | [S] | [A] | CONTINUE |
| | | [O] | [P] | CONTINUATION FACTOR DETAIL 1 |
| | ADD | | | |

(NEW ENTRY)

SELECTION OF IMEPLEMENTATION RECORDS — 440

| | DATE AND TIME IMPLEMENTED | ITEM NAME | MEASURED VALUE |
|---|---|---|---|
| ☐ | 2006/01/19 19:04 | SPO2 | 33% |
| ☐ | 2006/01/19 19:04 | RESPIRATION RATE | 3/MIN. |
| ☐ | 2006/01/19 19:06 | COMA | GOOD |
| ☐ | 2006/01/20 09:45 | BLOOD PRESSURE SYSTOLE/ LIE POSITION | 132mmHg |
| ☐ | 2006/01/20 09:45 | BLOOD PRESSURE DIASTOLE/ LIE POSITION | 98mmHg |
| ☑ | 2006/01/20 09:45 | BODY TEMPERATURE | 34.0°C |
| ☑ | 2006/01/20 09:45 | PULSE | 68/MIN. |
| ☑ | 2006/01/20 09:45 | HEART RATE | 65/MIN. |
| ☑ | 2006/01/20 09:45 | SPO2 | 96% |
| ☑ | 2006/01/20 09:45 | RESPIRATION RATE | 65/MIN. |

CANCEL  OK

64

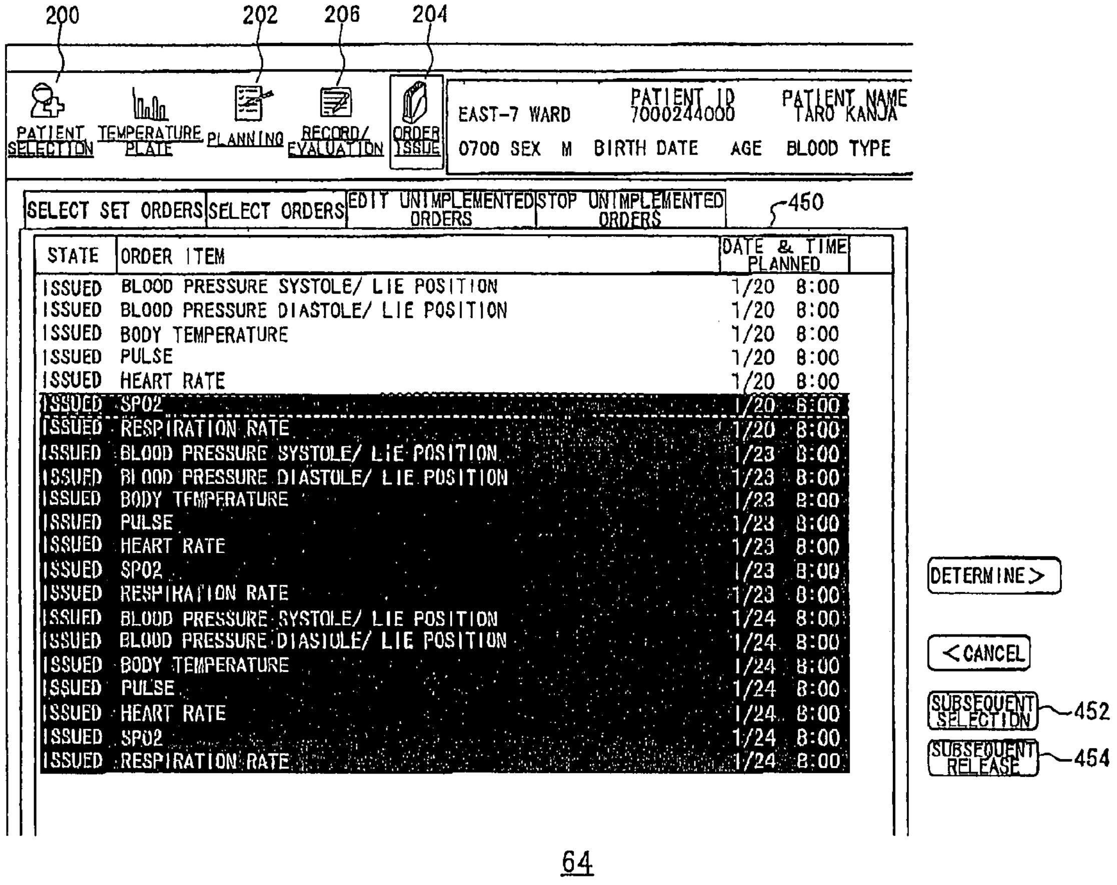

FIG.51A

| | 200 | 202 | 206 | 204 | | | |
|---|---|---|---|---|---|---|---|
| | PATIENT SELECTION | TEMPERATURE PLATE | PLANNING | RECORD/ EVALUATION | ORDER ISSUE | EAST-7 WARD  0700 SEX M | PATIENT ID 7000244000  BIRTH DATE AGE | PATIENT NAME TARO KANJA  BLOOD TYPE |

| SELECT SET ORDERS | SELECT ORDERS | EDIT UNIMPLEMENTED ORDERS | STOP UNIMPLEMENTED ORDERS | ~450 |
|---|---|---|---|---|

| STATE | ORDER ITEM | DATE & TIME PLANNED |
|---|---|---|
| ISSUED | BLOOD PRESSURE SYSTOLE/ LIE POSITION | 1/20 8:00 |
| ISSUED | BLOOD PRESSURE DIASTOLE/ LIE POSITION | 1/20 8:00 |
| ISSUED | BODY TEMPERATURE | 1/20 8:00 |
| ISSUED | PULSE | 1/20 8:00 |
| ISSUED | HEART RATE | 1/20 8:00 |
| ISSUED | SPO2 | 1/20 8:00 |
| ISSUED | RESPIRATION RATE | 1/20 8:00 |
| ISSUED | BLOOD PRESSURE SYSTOLE/ LIE POSITION | 1/23 8:00 |
| ISSUED | BLOOD PRESSURE DIASTOLE/ LIE POSITION | 1/23 8:00 |
| ISSUED | BODY TEMPERATURE | 1/23 8:00 |
| ISSUED | PULSE | 1/23 8:00 |
| ISSUED | HEART RATE | 1/23 8:00 |
| ISSUED | SPO2 | 1/23 8:00 |
| ISSUED | RESPIRATION RATE | 1/23 8:00 |
| ISSUED | BLOOD PRESSURE SYSTOLE/ LIE POSITION | 1/24 8:00 |
| ISSUED | BLOOD PRESSURE DIASTOLE/ LIE POSITION | 1/24 8:00 |
| ISSUED | BODY TEMPERATURE | 1/24 8:00 |
| ISSUED | PULSE | 1/24 8:00 |
| ISSUED | HEART RATE | 1/24 8:00 |
| ISSUED | SPO2 | 1/24 8:00 |
| ISSUED | RESPIRATION RATE | 1/24 8:00 |

[DETERMINE>]

[<CANCEL]

[SUBSEQUENT SELECTION]~452

[SUBSEQUENT RELEASE]~454

64

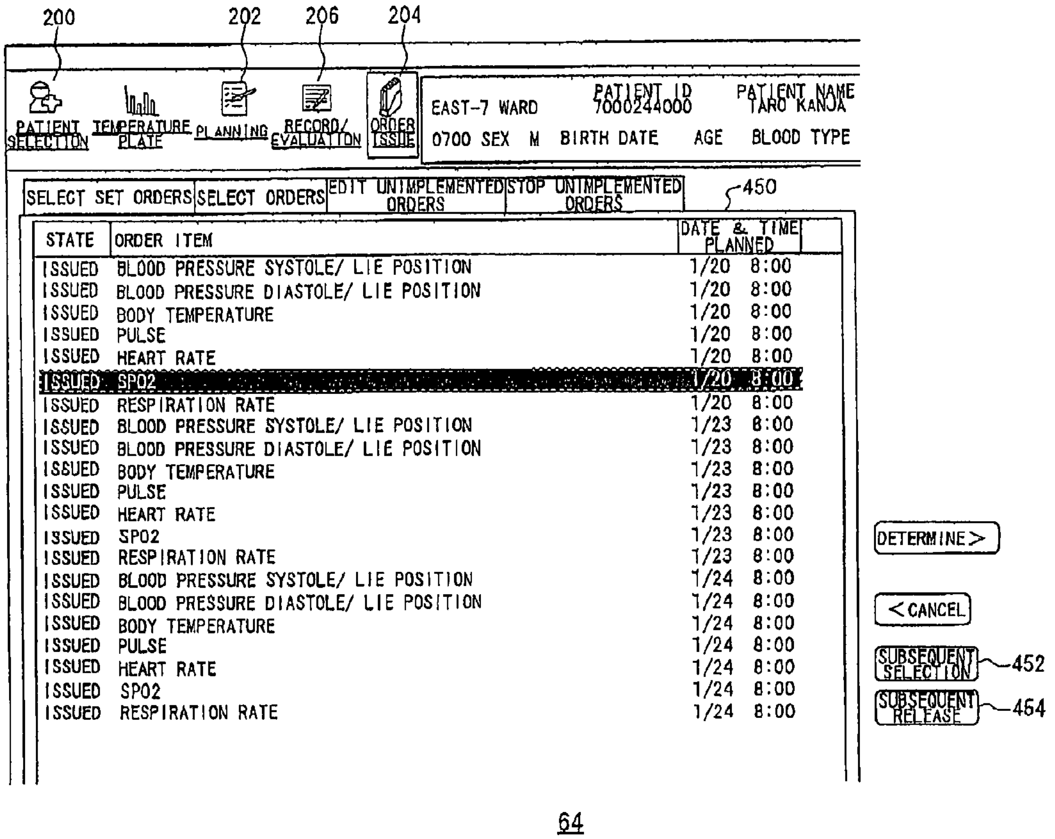

FIG.51B

| STATE | ORDER ITEM | DATE & TIME PLANNED |
|---|---|---|
| ISSUED | BLOOD PRESSURE SYSTOLE/ LIE POSITION | 1/20 8:00 |
| ISSUED | BLOOD PRESSURE DIASTOLE/ LIE POSITION | 1/20 8:00 |
| ISSUED | BODY TEMPERATURE | 1/20 8:00 |
| ISSUED | PULSE | 1/20 8:00 |
| ISSUED | HEART RATE | 1/20 8:00 |
| ISSUED | SPO2 | 1/20 8:00 |
| ISSUED | RESPIRATION RATE | 1/20 8:00 |
| ISSUED | BLOOD PRESSURE SYSTOLE/ LIE POSITION | 1/23 8:00 |
| ISSUED | BLOOD PRESSURE DIASTOLE/ LIE POSITION | 1/23 8:00 |
| ISSUED | BODY TEMPERATURE | 1/23 8:00 |
| ISSUED | PULSE | 1/23 8:00 |
| ISSUED | HEART RATE | 1/23 8:00 |
| ISSUED | SPO2 | 1/23 8:00 |
| ISSUED | RESPIRATION RATE | 1/23 8:00 |
| ISSUED | BLOOD PRESSURE SYSTOLE/ LIE POSITION | 1/24 8:00 |
| ISSUED | BLOOD PRESSURE DIASTOLE/ LIE POSITION | 1/24 8:00 |
| ISSUED | BODY TEMPERATURE | 1/24 8:00 |
| ISSUED | PULSE | 1/24 8:00 |
| ISSUED | HEART RATE | 1/24 8:00 |
| ISSUED | SPO2 | 1/24 8:00 |
| ISSUED | RESPIRATION RATE | 1/24 8:00 |

Patient tabs: PATIENT SELECTION (200), TEMPERATURE PLATE (202), PLANNING, RECORD/EVALUATION (206), ORDER ISSUE (204)

Header: EAST-7 WARD 0700 SEX M BIRTH DATE AGE BLOOD TYPE PATIENT ID 7000244000 PATIENT NAME TARO KANJA Tabs: SELECT SET ORDERS | SELECT ORDERS | EDIT UNIMPLEMENTED ORDERS | STOP UNIMPLEMENTED ORDERS — 450

Buttons: DETERMINE>, <CANCEL, SUBSEQUENT SELECTION —452, SUBSEQUENT RELEASE —454

NURSING INFORMATION MANAGEMENT METHOD AND NURSING INFORMATION MANAGEMENT APPARATUS FOR MANAGING NURSING ACTIONS

CROSS-REFERENCE TO RELATED APPLICATIONS

This application is based upon and claims the benefit of priority from the prior Japanese Patent Application No. 2006-111358, filed Apr. 13, 2006, the entire contents of which are incorporated herein by reference.

BACKGROUND OF THE INVENTION

1. Field of the Invention

The present invention relates to a nursing information management technique and it particularly relates to method and apparatus for managing the nursing information.

2. Description of the Related Art

Systems provided for managing the medical actions, particularly nursing care actions, include a server, personal computers (hereinafter referred to as "PC"), PDAs (Personal Digital Assistants) and the like, which are connected together by wired or wireless LAN (Local Area Network). In such a structure, the server records data used in an entire system and the PC receives the registrations of orders and other information from nurses and the like. The nurses, who carry PDAs with them, conduct intravenous drips upon patients by referring to the work list containing intravenous drips and the like as work schedules to be done. Further, after the work of intravenous drip was conducted on the patients, the nurse would input implementation results into the PDA. The implementation results inputted to the PDA are transmitted to the PC and the server, so that the PC and the server can manage the implementation results (See Reference (1) in the following Related Art List, for instance).

Related Art List (1) Japanese Patent Application Laid-Open No. 2004-110818.

In the conventional technology, the nurses verify the contents of nursing care while operating the PDA in positions where the nursing care is conducted, so that the error in the nursing work can be reduced. Further, since the nurses enter the nursing results while operating the PDAs, the possibility of neglecting the entry of the nursing results can be reduced. The PC is more desirable than PDA in the management of the nursing actions actually implemented and those schedule to be done. In consideration of a general operability of PDAs, a large amount of data is not assumed generally in PDAs and, instead, assumed is the viewing of data on the actual nursing care site such as a patient's room and an operation room. For this reason, the nurses enter a large amount of data into PCs and manage the nursing actions in a nurses' station. In other words, the PC is required to operate in a manner that the nursing actions are managed with accuracy. In general, proper nursing care is required in hospitals and, in order to achieve the proper nursing care, the accurate management of nursing action is also required.

SUMMARY OF THE INVENTION

The present invention has been made in view of the foregoing circumstances, and a general purpose thereof is to provide a nursing information management technology by which to provide proper nursing actions.

In order to resolve the above problems, a nursing information management apparatus according to one embodiment of the present invention comprises: a setting unit which sets a plan on a medical action for a patient; an implementation recording unit which records a content of an implementation of a nursing action conducted along with the plan set by the setting unit; a discrepancy information input unit which inputs, per problem related to a patient's disease, information on a factor of discrepancy between the content of an implementation recorded by the implementation recording unit and the plan set by the setting unit; and a discrepancy information recording unit which records the information on a factor of discrepancy inputted by the discrepancy information input unit and the problem related to the patient's disease by associating the information on a factor of discrepancy and the problem related to the patient's disease.

"Problem related to a patient's disease" is a problem by which to specify the patient's disease, and it includes a diagnosis and treatment department, a disease and a problem, for example. According to this embodiment, the factors of discrepancy are inputted by relating them to the problems on a patient's disease, so that the factors of discrepancy can be managed for each of the problems related to a patient's disease.

Another embodiment of the present invention relates to a nursing information management apparatus. This apparatus comprises: a setting unit which sets a problem related to a patient's disease and a plan for the problem; an implementation recording unit which records a content of an implementation of a nursing action conducted along with the plan set by the setting unit; a discrepancy information input unit which inputs, per problem related to a patient's disease, information on a factor of discrepancy between the content of an implementation recorded by the implementation recording unit and the plan set by the setting unit; and a discrepancy information recording unit which records the information on a factor of discrepancy inputted by the discrepancy information input unit and the problem related to a patient's disease by associating the information on a factor of discrepancy and the problem related to the patient's disease.

According to this embodiment, the factors of discrepancy are entered by relating them to the problems on a patient's disease, so that the factors of discrepancy can be managed for each of the problems related to a patient's disease.

The apparatus may further comprise a standard plan recording unit which records a standard problem for each patient's disease and a standard plan for each of the standard problems. The setting unit may select a problem and a plan for a patient to be attended, from among standard problems and plans therefor recorded in the standard plan recording unit. In such a case, the problem and the plan are selected from among the recorded standard problems and plans, so that the problems and the plans can be easily set.

The apparatus may further comprise a standard plan recording unit which records a standard problem for each patient's disease and a standard plan for each of the standard problems. The discrepancy information recording unit may include: a means which selects another problem than the problem set by the setting unit, from the standard problems recorded in the standard plan recording unit; and a means which inputs information on a factor of discrepancy between the content of an implementation recorded by the implementation recording unit and a standard plan corresponding to the another selected problem, by associating the information with the another selected problem. In such a case, even if another problem occurs while conducting a nursing care, a factor of discrepancy corresponding to this new problem can be inputted.

The standard problems recorded in the standard plan recording unit may further include information on diagnosis and treatment departments; when setting the problems and plans, the setting unit may set the information on diagnosis and treatment departments; and when inputting the information on a factor of discrepancy, the discrepancy information input unit may further input the information on diagnosis and treatment departments. In this case, factors of discrepancy can be managed for each of the diagnosis and treatment departments.

Still another embodiment of the present invention relates to a method for managing nursing information. This method comprises: setting a plan on a medical action for a patient; recording a content of an implementation of a nursing action conducted along with the plan set by the setting; inputting, per problem related to a patient's disease, information on a factor of discrepancy between the content of an implementation recorded by the recording and the plan set by the setting; and recording the information on a factor of discrepancy inputted by the inputting and the problem related to the patient's disease by associating the information on a factor of discrepancy and the problem related to the patient's disease.

It is to be noted that any arbitrary combination of the above-described structural components or rearrangement in the form among a method, an apparatus, a system, a recording medium, a computer program and so forth are all effective as and encompassed by the present embodiments.

BRIEF DESCRIPTION OF THE DRAWINGS

Embodiments will now be described by way of examples only, with reference to the accompanying drawings which are meant to be exemplary, not limiting.

FIG. 3 illustrates a data structure of nursing information recorded in a recording unit of FIG. 2;

FIG. 5 illustrates a data structure of patient information recorded in a recording unit of FIG. 2;

FIG. 7 illustrates a screen, at a stage of patient selection, displayed on a display apparatus of FIG. 2;

FIG. 8 illustrates a data structure of a nursing problem database contained in a first database of FIG. 2;

FIG. 9 illustrates a data structure of a nursing care plan database included in a second database of FIG. 2;

FIG. 23 shows conditions stored in a storage of FIG. 2;

FIG. 31 illustrates a counting result recorded in a counting unit of FIG. 2;

FIG. 38 illustrates a screen obtained after a nursing care plan displayed on a display apparatus of FIG. 2 has been entered;

FIG. 40 illustrates a data structure for an entry setting of variance factors stored in a management unit according to an embodiment;

FIG. 43 shows another counting result recorded in a counting unit of FIG. 2;

FIG. 44 shows still another counting result recorded in a counting unit of FIG. 2;

FIGS. 46A and 46B illustrates identification numbers of nursing problems displayed on a display apparatus of FIG. 2;

FIGS. 48A and 48B each illustrates an entry screen of a nursing problem in a display apparatus of FIG. 2;

FIG. 51A illustrates a display screen for issuing orders in a display apparatus of FIG. 2;

FIG. 51B illustrates a display screen for issuing orders in a display apparatus of FIG. 2;

DETAILED DESCRIPTION OF THE INVENTION

Figure 1:
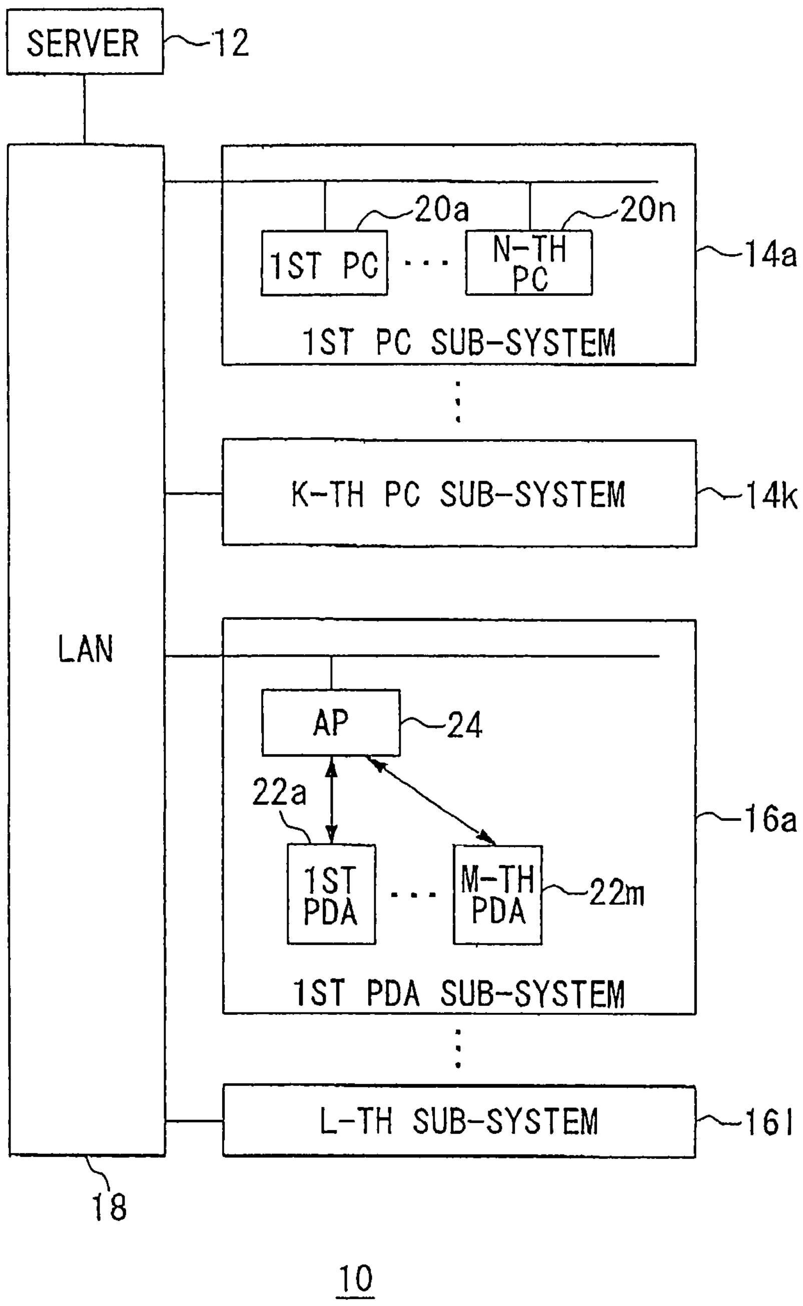
FIG. 1 illustrates a nursing information management system according to an exemplary embodiment of the present invention.

The invention will now be described by reference to the preferred embodiments. This does not intend to limit the scope of the present invention, but to exemplify the invention.

An outline of the present invention will be given before a specific description thereof. Exemplary embodiments of the present invention relate to a nursing system for managing nursing actions performed on patients and nursing actions yet to be performed on the patients. A nursing information management system includes PCs installed in a nurses' station and the like, PDAs carried by nurses and a server for recording data used in the nursing information management system, and all of these are connected with one another via a LAN. The nursing information management system is characterized mainly by the following features.

The first feature is that a plurality of stages are defined for a nursing care activity and the nursing care activity is managed by relating each of stages to one another. Since the plurality of stages are so structured as to be cyclic, ongoing nursing care activity implementation contents can be determined with the past nursing care activity implementation contents taken into consideration. The second feature is that the screen of a PC is structured so that nursing care activity contents at the plurality of stages can be read through. The nurses use PDAs while performing nursing care activities, but they basically use PCs when doing activities other than the nursing care activities. By employing the structure of a screen as above, the nursing care activity contents can be verified and determined by relating each of the plurality of stages to one another.

Third feature is that since adjacent two stages among the plurality of stages must have a relevancy to each other, once one of them having the relevancy is determined, the contents thereof is automatically reflected in the other. As a result, the entry of the other is supported and therefore the load of the entries and possible entry mistakes can be reduced. The fourth feature is that in a case when there is discrepancy between a patient's recovery schedule and an actual recovery, a factor attributed thereto is also entered. By analyzing the discrepancy, the contents of nursing care activities can be improved.

With the above-described features, a general purpose of the nursing information management system according to the embodiments is to provide proper nursing care actions. The following background lies behind this purpose. Under the current health-care system after a reform, strict management of revenue and expenditure is required in hospitals. Given the importance of managing a hospital, the hospital tends to suppress the expenditure. In the current health-care system, the prolonged duration of patient hospitalization will increase the hospital's expenditure. For this reason, it is desired that the nursing care actions be so improved that the length of hospital stay for a patient be shortened. This is beneficial not only from the standpoint of hospitals but also from the standpoint of patients.

A nursing information management system will now be described below. To clarify a description, the entire description is divided into six sections. In section (1), a general outline of the nursing information management system is described, and each part included in the nursing information management system will be described in sections (2) to (8).

1. General Structure

A description of terminologies defined in the nursing information system will be given before a description of a structure of the nursing information management system. "Nursing problem" indicates a symptom to be taken care of by a nursing care, and this corresponds to a problem to be resolved by a nurse's proactive action. Examples of the nursing problems include "there is a concern about rebleeding and its treatment", "comfortable environment cannot be maintained due to hematemesis and nelena" and "mental turmoil is inevitable as a result of massive hematemesis and melena", which are problems all adversely effecting the degree of recovery of a patient. If the nursing problem involves a plurality of items, each will be indicated as "nursing problem item".

"Nursing care plan" indicates a nursing policy for a patient and it corresponds to a plan for a nursing care. The nursing care plan includes four items, namely, (1) a plan to resolve a problem deterring a planned target, (2) an effect expected when it is resolved, (3) a targeted patient condition and (4) an evaluation. A planned target indicates a condition expected for a nursing problem, and corresponds to a desirable patient condition. Examples of targets include "can accept and live with the disease", "can understand the necessity of a long period of treatment and participate positively in the treatment" and "be aware of and have motivation toward self-care and can take daily-life action suited for a symptom".

The plan include an observation plan (OP), a care plan (CP), and an education-guidance plan (EP). OP indicates an observation item for determining a course, CP indicates a medical care, a therapy, a treatment and the like, EP indicates education regarding knowledge, method, technique and the like necessary for coping with the problem prevention, alleviation and resolution for oneself. Examples of OP include "blockage of upper respiratory tract and respiratory discomfort during the night (tongue being flatly positioned toward the back of the mouth; irregular respiration with stertor)" and "respiratory condition (respiration frequency, depth, rhythm, chest motion, the presence or absence of dyspnea on effort". Examples of CP include "a body posture is maintained where there is no strain to the chest motion" and "coughing is encouraged and, at the time of coughing, assist a patient to hold the abdomen tight by both hands". One example of EP is "explain the condition of disease to a patient and his/her family members and ask for their cooperation".

"Nursing items" indicate contents of a nursing care for a patient. The nursing items are contained in the nursing care plan and correspond to the above-described plan. Here, the nursing item includes OP, CP and EP contained in the above-described plan. Note that the nursing item may contain contents other than the above-mentioned ones and it may be any contents as long as it is to be performed by a nurse.

The problems to be resolved here may be indicated as follows. In order for the nursing contents to be most appropriate, it is desired that the correspondence between the nursing contents and the results thereof be clarified. It is desired that mistakes be minimized. It is also desired that alteration of the nursing contents be prevented. It is desired that the responsibility of nurses be clarified as to correction works for the recorded nursing contents. It is also desired that the patient hospitalization length be minimized.

FIG. 1 illustrates a nursing information management system 100 according to an exemplary embodiment of the present invention. The nursing information management system 10 includes a server 12, a first PC subsystem 14*a*, and a Kth PC sub-system 14*k*, which are generically referred to as "PC sub-system 14", a first PDA sub-system 16*a*, . . . and an Lth PDA sub-system 16*l*, which are generically referred to as "PDA sub-system 16", and a LAN 18. The first PC sub-system 14*a* includes a first PC 20*a*, . . . and an Nth PC 20*n*, which are generically referred to as "PC 20". The first PDA sub-system 16*a* includes an AP (Access Point) 24, a first PDA 22*a*, . . . an Mth PDA 22*m*, which are generically referred to as "PDA 22". For clarify of the Figure, the description of the structure of the PC sub-system 14 and the PDA sub-system 16 except for the first PC sub-system 14*a* and the first PDA subsystem 16*a* is omitted. It is assumed, however, that the structures for those omitted in FIG. 1 are the same as those of the first PC sub-system 14*a* and the first PDA sub-system 16*a*.

The PC sub-system 14, which includes a plurality of PCs 20, is provided in a nurses' station, for instance. The respective PC sub-systems 14 are connected to one another via the LAN 18, and the PCs 20 in each PC sub-system 14 are also connected to one another. In the nurses' station, medical staff members, such as nurses, enter data, refer to and verify the data or perform other tasks. The PC 20 supports the nurses in preparing the nursing problem items, supports the preparation of nursing care plans based on the thus prepared items for nursing problems and then specifies the implementation of nursing items contained in the prepared nursing care plans.

Here, in a case when "nursing problem item" contains a plurality of items, the items correspond respectively to the nursing problem items. "Supporting in preparing the nursing problem items" and "support of the preparation of nursing care plans" correspond to the implementation of processings, such as supporting the preparation by the PC 20 when a nurse prepares for a nursing problem and a nursing care plan. Though the detail will be discussed later, the preparation of a nursing care plan is supported by conducting search through a database based on the nursing items prepared for a patient. Here, the database contains nursing care plan items which are respectively associated beforehand with a plurality of kinds of items to be included in the nursing problem.

The PDA sub-system 16 is provided in places, where a nursing care is performed, such as a patient's room, an examination room, an operation room and the like, and the PDA sub-system 16 includes an AP 24 and a PDA 22. The PDA 22 and the AP 24 are connected via a wireless LAM. The PDA sub-system 16 is connected with the PC sub-system 14 via the LAN 18. The PDA 22 has normal PDA functions which include a means, for inputting data, such as a touch panel, a processing means, such as a CPU, for processing the inputted data, a means for storing the data, and a display means for displaying the processed data and the like. The PDA 22 has a communication function using a wireless LAN and a means for reading identification information, such as an identification code reader capable of reading the identification information. The identification information reading means may be an OCR (Optical Character Reader) which optically reads characters, an image scanner which reads in the characters or graphics as an image, a transponder which can read in the identification information by a wireless communication or the like. The identification information may be entered by a user.

The PDA 22, which is equipped with a communication function of a wireless LAN, can access the LAN 18 within a coverage area provided by the AP 24. As a result, the PDA 22 accesses the PC 20 and the server 12 to acquire the nursing care plan items, and then displays the acquired nursing care plan items on a display unit of the PDA 22. The nurse verifies the nursing care plan items displayed on the display unit of the PDA 22 and performs a nursing care according to the nursing care plan items. The nurse also enters implementation results of the nursing items. The PDA 22 transmits the implementation results to the PC 20.

The PC 20 receives the implementation results from the PDA 22. Further, the evaluations for the implementation results of nursing items are entered into the PC 20 by the nurse. The "evaluation" includes subjective and objective evaluations for a patient. The detailed description thereof will be given later. The PC 20 stores the entered evaluations, and the implementation results entered via the PDA 22 are recorded in memory. The PC 20 selects an implementation result that meets a predetermined condition, from among the implementation results recorded in memory, and then displays it on a partial area of screen. The implementation result is displayed on a partial area of screen, and other information such as nursing problems and nursing care plans is displayed on the other areas of screen.

Furthermore, while inputting the evaluations, when there is a discrepancy between an implementation result of a nursing item and a planned target in the nursing item specifying an implementation, the PC 20 also inputs information on a contributing factor of the discrepancy (hereinafter referred to as "variance factor") and records this factor by associating it with the evaluation. Here, the variance factor includes a case where the implementation result shows a more desirable result than the planned target (hereinafter referred to as "positive variance") and a case where the implementation result shows a worse result than the planned target (hereinafter referred to as "negative variance"). The case where the implementation result shows a more desirable result than the planned target corresponds to a case where the actual hospital discharge date comes earlier than a predetermined scheduled hospital discharge date. That is, it means that the recovery is faster than expected.

The server 12 stores data used in the nursing information management system 10. Although it is assumed herein that a single server 12 is provided, a plurality of servers 12 may be provided in the nursing information management system 10. In such a case, the servers 12 may be included in the PC sub-system 14. Furthermore, a hierarchical structure may be formed by a plurality of servers 12. In the following description, a description will be given on the assumption that data are communicated between the PC 20 and the PDA 22, for clarity of explanation. However, these data may be communicated between the PC 20 and the PDA 22 via the server 12. Also, the contents of data recorded in the server 12 and the contents of data recorded in the PC 20 may be subjected to a processing by using a known technique so that they are the identical data.

The PC sub-system 14 and the PDA sub-system 16 correspond, more specifically, to an out-patient system where the registration or the like of orders for injection and so forth is made, a ward system, a pharmaceutical division system where medicines are dispensed and paid out based on the registration of orders like an injection, a medical system where an account processing or the like for medical actions is carried out, a nursing system (or nurses' station system) where nurses perform mixture injections, and the like. The present embodiment relates to a nursing system. In particular, each nurse carries the PDA with her/him in a nurses' station or a ward where nurses conduct nursing care actions, and he/she goes to a place where a nursing action is conducted, namely the bedside of a hospitalized patient. At this spot, data on the particular medical action are inputted and outputted. As a result thereof, the conditions and states of nursing care actions are recorded in a real-time manner and grasped.

Figure 2:
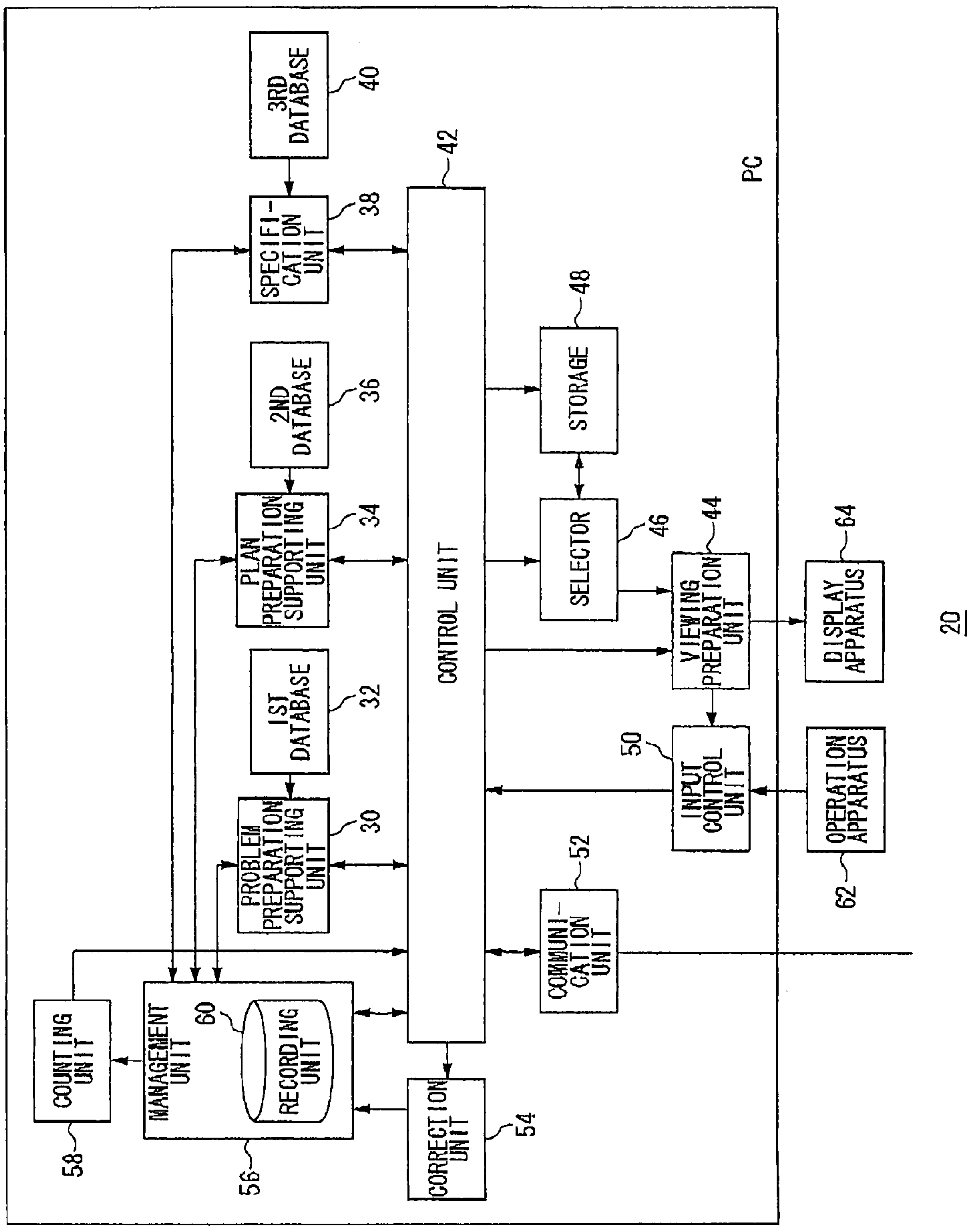
FIG. 2 illustrates a structure of a PC shown in FIG. 1.

FIG. 2 illustrates a structure of the PC 20. The PC 20 includes a problem preparation supporting unit 30, a first database 32, a plan preparation supporting unit 34, a specification unit 38, a third database 40, a control unit 42, a viewing preparation unit, a selector 46, a storage 48, an input control unit 50, a communication unit 52, a correction unit 54, a management unit 56, and a counting unit 58. The management unit 56 includes a recording unit 60. The PC 20 is connected with an operation apparatus 62 and a display apparatus 64.

The display apparatus 64 displays predetermined information. The display apparatus 64 may be structured integrally with the PC 20. The viewing preparation unit 44 generates a screen to be displayed on the display apparatus 64. The viewing preparation unit 44 receives information necessary for generating a screen to be displayed, from the control unit 42. In the present embodiment, a screen generated by the viewing preparation unit 44 is so structured as to be able to read through the respective contents at a plurality of nursing stages. The structure of this screen will be discussed later.

The operation apparatus 62 is operated by a nurse and inputs predetermined information to the PC 20. The operation apparatus 62 is comprised of a keyboard, a mouse and so forth. The operation apparatus 62 may also be integrally structured with the PC 20. The input control unit 50 outputs the received information to the control unit 42. In general, while verifying the screen displayed on the display apparatus 64, a nurse enters predetermined information using the operation apparatus 62. Accordingly, in order to recognize which part of the screen corresponds to the information inputted by the operation apparatus 62, the input control unit 50 receives information on a screen structure from the viewing preparation unit 44.

Figure 18:
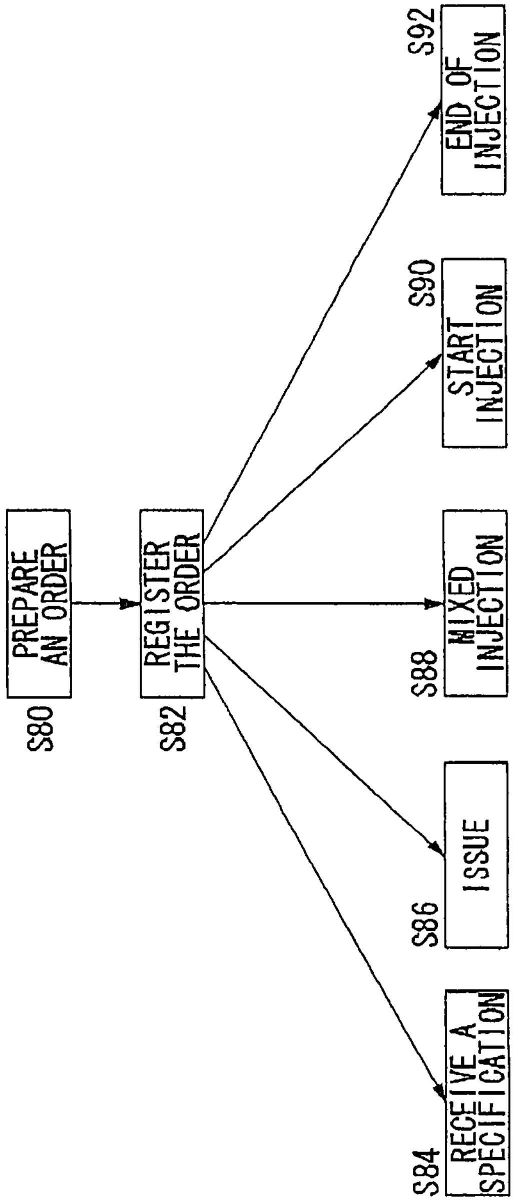
FIG. 18 is a schematic view showing an order issuance processing in a nursing information management system of FIG. 1.

The communication unit 52 is connected with the LAN 18 of FIG. 18, and communicates with the server 12, other PCs 20 and the PDA 22. The communication unit 52 receives information to be transmitted, from the control unit 42 and outputs the received information to the control unit 42. The communication unit 52 communicates with the PDA 22 at a predetermined timing to establish a data synchronism between the PC 20 and the server 12. The control unit 42 controls the input and output of predetermined information between components included in the PC 20. That is, the control unit 42 receives information from one component and then outputs the information to the another component. It is assumed that one component and another component are switched as appropriate. Accordingly, the control unit 42 has a switching function. For clarity of explanation, operations of one component and another component will be described hereinbelow, and the description of the control unit 42 is omitted.

The problem preparation supporting unit 30 supports the preparation of nursing problem items for a patient. In cooperation with the first database 32, the problem preparation supporting unit 30 outputs options necessary for preparing the nursing problems to the display apparatus 64. Subsequently, the problem preparation supporting unit 30 receives the selected options from the operation apparatus 62. By repeating the above operation, the problem preparation supporting unit 30 supports finally the preparation of nursing problem items. Also, the problem preparation supporting unit 30 receives comments to the thus prepared nursing problem items. The problem preparation supporting unit 30 outputs the thus prepared nursing problems items to the plan preparation supporting unit 34 and the recording unit 60, for example. A structure is such that these outputs from the problem preparation supporting unit 30 are fed thereto by way of the control 42 and the management unit 56.

The plan preparation supporting unit 34 supports the preparation of a nursing care plan based on the prepared nursing problem items. The plan preparation supporting unit 34 extracts a nursing care plan corresponding to the prepared nursing problem items, by searching through the second database 36 using the prepared nursing problem items. The contents of data contained in the second database 36 will be discussed later. The plan preparation supporting unit 34 displays the extracted nursing care plan on the display apparatus 64. Further, the plan preparation supporting unit 34 receives comments to the prepared nursing care plans. The plan preparation supporting unit 34 outputs the prepared nursing care plan to the recording unit 60.

In cooperation with the third database 40, the specification unit 38 specifies an implementation of nursing items contained in the nursing care plan. The specification unit 38 transmits the specification of an implementation of nursing items via the communication unit 52. The specification unit 38 may display a specification of nursing items on the display apparatus 64. When the specified nursing item is conducted by a nurse, the nurse enters the result into the PDA 22, and then PDA 22 transmits the implementation result of the nursing items to the communication unit 52. Upon receipt of the implementation result of the nursing items, the communication unit 52 outputs it to the recording unit 60. Further, the nursing result stored in the recording unit 60 is displayed on the display apparatus 64. In so doing, a nursing result to be displayed on the display apparatus 64 is selected by the selector 46 and the storage 48.

The nurse enters an evaluation of the implementation result of nursing items into the operation apparatus 62. The entered evaluation is recorded in the recording unit 60. Among the nursing problem items stored in the recording unit 60, the nursing items contained in the nursing care plan, the implementation results and the evaluations, the management unit 56 relates the mutually corresponding items with one anther, by a series of identifiers. That is, if, for example, "#1" serving as an identifier is assigned to an item of the nursing problems, then "#1" will also be assigned to the nursing items contained in a nursing care plan, the implementation results and the evaluations corresponding to this nursing problem item. As a result, a screen is created so that the nursing problem items, the nursing items contained in the nursing care plan, the implementation results and the evaluations are integrally contained within a single screen. Linked with the entered evaluations, another nursing care plan is inputted to the recording unit 60. The processings performed subsequent to the inputted nursing care plan are the same as those described so far and therefore the repeated description thereof is omitted here. Note that it suffices if the recording unit 60 has a function of storing predetermined information, and the recording unit 60 includes a hard disk or RAM (Random Access Memory). Moreover, the recording unit 60 may be structured by a plurality of recording media, for example, a hard disk and a RAM. For simplicity, no distinction will be made hereinafter therebetween.

The correction unit 54 receives corrections corresponding to at least one of the nursing problem item recorded in the recording unit 60, the nursing item contained in a nursing care plan, the implementation result and the evaluation. In so doing, alteration by the third parties is prevented. Hence, the correction unit 54 performs a management in such a manner that the history of corrections is not deletable. For example, the correction unit 54 manages the history of corrections and, in so doing, it manages also the dates of correction and the persons who enter the correction.

When an evaluation is entered, there are cases where a variance factor is entered into the operation apparatus 62. Though a description will be given later of the variance factor, the recording unit 60 records the variance factors by associating them with nursing problem items and nursing items, implementation results and evaluations contained in a nursing care plan. The counting unit 58 performs a predetermined counting processing on the variance factors recorded in the recording unit 60.

In terms of hardware, this structure described as above can be realized by a CPU, a memory and other LSIs of an arbitrary computer. In terms of software, it can be realized by memory-loaded programs which have a reserved management function or the like, but drawn and described herein are function blocks that are realized in cooperation with those. Hence, it is understood by those skilled in the art that these function blocks can be realized in a variety of forms such as by hardware only, software only or the combination thereof.

FIG. 3 illustrates a data structure of nursing information recorded in the recording unit 60. FIG. 3 illustrates the nursing information for a single patient but the recording unit 60 records the nursing information corresponding to a plurality of patients. The nursing information contains an identification number space 100, a nursing problem space 102, a nursing care plan space 104, an implementation result space 106, a nursing record space 108, and a variance factor space 110. The identification numbers assigned by the management unit 56 are recorded in the identification number space 100. A nursing problem item, a nursing item contained in a nursing care plan, an implementation result, an evaluation and a variance factor corresponding to a predetermined identification number are recorded in the nursing problem item space 108, the nursing care plan space 104, the implementation result space 106, the nursing record space 108 and the variance factor space 110, respectively. The contents of the nursing care plan space 104, the implementation result space 106, the nursing record space 108 and the variance factor space will be discussed later.

Figure 4:
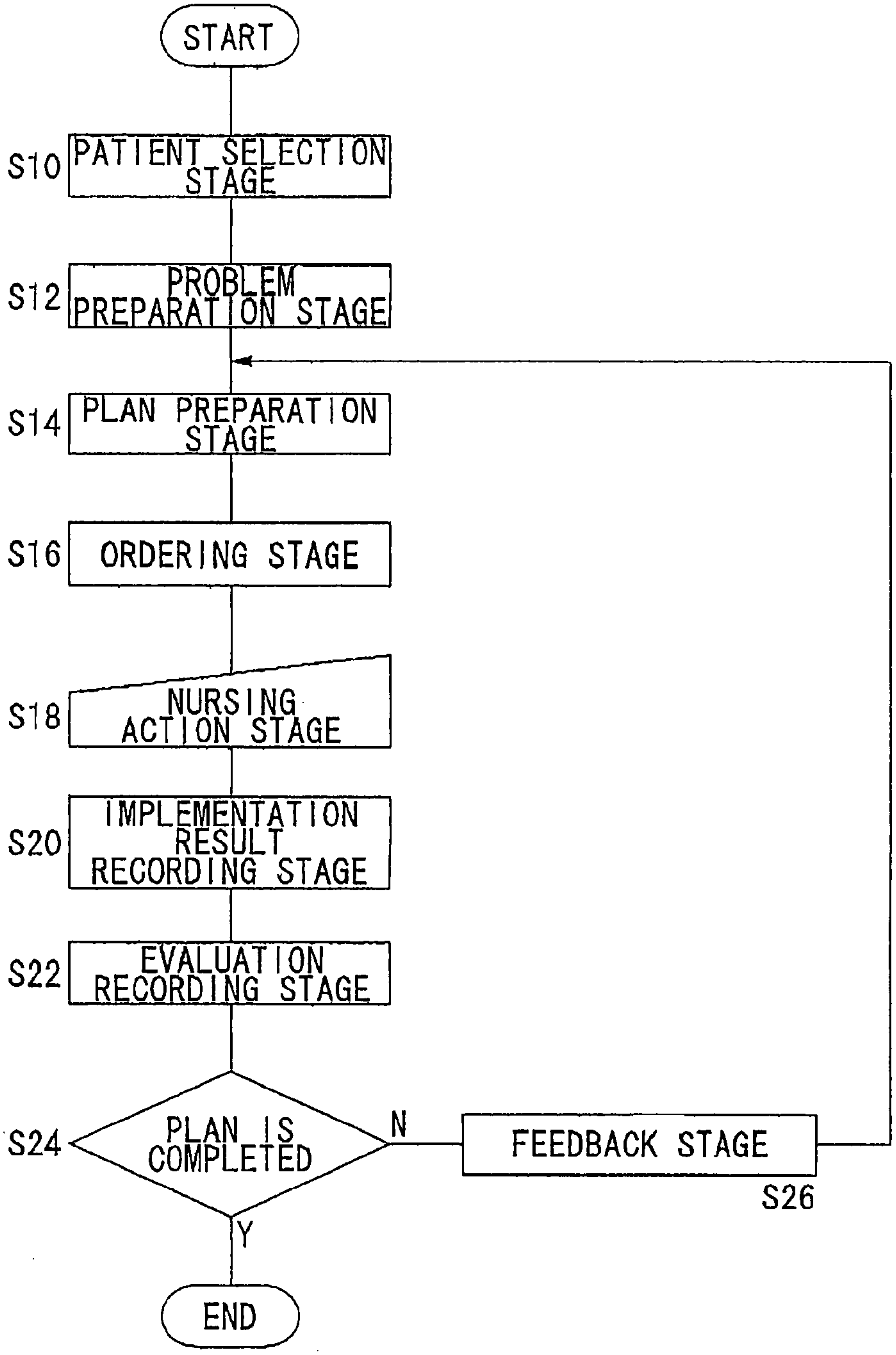
FIG. 4 is a flowchart showing a procedure for managing the nursing information in the nursing information management system of FIG. 1.

FIG. 4 is a flowchart showing a procedure for managing the nursing information in the nursing information management system 10. Each step in the flowchart corresponds to each of a plurality of stages defined for a nursing care. The management unit 56 executes a patient selection stage (S10). The patient selection stage corresponds to a stage where information on a single patient is selected from among information on a plurality of patients recorded in the recording unit 60. In so doing, the nurse selects a patient using the operation apparatus 62. The problem preparation supporting unit 30 executes a problem preparation stage (S12). The problem preparation stage corresponds to a stage where items for a nursing problem are prepared. The plan preparation supporting unit 34 executes a plan preparation stage (S14). The plan preparation stage corresponds to a stage where nursing care plans are prepared. The specification unit 38 executes an order stage (S16). The order stage corresponds to a stage where the implementation of nursing items are specified. At this stage, orders are issued and the contents of nursing items are outputted to the PDA 22.

The nurse performs a nursing care action stage (S18). The nursing care action stage corresponds principally to a stage where a human-induced task is conducted. The PDA 22 and the recording unit 60 execute an implementation result recording stage (S20). The implementation result recording stage corresponds to a stage where the nurse enters an implementation result into the PDA 22, the communication unit 52 receives this implementation result and then the recording unit 60 records the implementation result. The recording unit 60 executes an evaluation recording stage (S22). The evaluation recording stage corresponds to a stage where the recording unit 60 records variance factors via the operation apparatus 62. At this stage, the management unit 56 receives an input as to whether a nursing care plan is to be terminated or not. If the plan is to be terminated (Y of S24), the processing will be terminated. If the plan is not completed (N of S24), the management unit 56 and the like will execute a feedback stage (S26). The feedback stage corresponds to a stage where the processing from Step 14 onward is repeated. In so doing, the nursing care plan may be amended or revised and another nursing care plan may be newly added.

A description will now be given of an operation of the nursing information management system 10 structured as above. The nurse operates the PC 20 installed in the nurses' station and selects a patient or patients to whom a nursing care is to be provided. The nurse prepares nursing problem items using the PC 20, where a nursing care plan is prepared based on the thus prepared nursing problem items. The nurse issues an order to the server 12 from the PC 20, by referring to nursing items contained in the nursing care plan. The order is also sent to the PDA 22. While verifying the nursing items displayed on the PDA 22 in a patient's room, the nurse performs nursing care actions. Further, the nurse enters an implementation result of the nursing care actions into the PDA 22 from which the implementation result is sent to the PC 20. The nurse returns again to the nurse's station and enters an evaluation into the PC 20. The PC 20 records the implementation result received from the PDA 22 and the evaluation by associating them with each other. Also, a nursing care plan is added based on the evaluation.

By employing the above structure, a plurality of stages are defined for a nursing care and the management is performed by relating the plurality of stages to one another, so that the relationship between the nursing contents and the nursing results can be clarified. Also, since the relationship between the nursing contents and the nursing results is clarified, nursing contents required to yield a predetermined nursing result can be grasped. Also, more appropriate nursing contents can be derived by improving the contents. The improvement of the nursing contents can lead to shortening the length of patient hospitalization. The reduced duration of patient hospitalization is also desirable for the patient himself/herself. Since items related to one another, among the items for a nursing problem, the nursing items contained in a nursing care plan and evaluations, are brought into correspondence with one another by the use of a series of identifiers, the occurrence of mistakes in managing these items can be reduced. Also, the management of these items can be facilitated. Since the history of corrections is so managed as not to be deletable, the alteration of the nursing contents can be prevented. With this correction, if any inconvenience is caused in a nursing care, such a particular correction can be specified. Also, this draws the nurses' attention to the correction. Also, shared responsibility by nurses for the corrections can be clarified.

Since the difference between time when a nursing care action to be recorded takes places and time when an actual nursing care action takes place becomes smaller, so that the nursing care actions can be recorded and grasped with accuracy. Since the nurse verifies, by a PDA, the contents of work schedule for nursing care actions at a site where the nursing care actions are conducted, the accuracy of nursing care actions can be enhanced. Since the nurse enters the implementation result at once at the site the nursing care actions take place, the entry can be made with accuracy. Since the nurse verifies, by the PDA, the contents of nursing care actions in arbitrary places at any time, the nursing care action is conducted smoothly. Even in a case where the contents of nursing care actions are changed, the changed contents of nursing care actions can be appropriately dealt with if the nurse uses the PDA at the implementation site and verifies the changed contents of nursing care actions before conducting a nursing care. Since the nursing information management system accurately records the implementation result, an administrator and the like can improve the system by analyzing the recorded data later to achieve a further suitable state.

2. Patient Selection

Patient selection corresponds to Step 10 in FIG. 4. Problems to be resolved here may be expressed as follows. It is desired that the selection of patients be made in a simplified manner. Also, it is desired that the selection of patients be made accurately. To select patients, the viewing preparation unit 44, the display apparatus 64, the operation apparatus 62, the input control unit 50, the control unit 42, the management unit 56 and the recording unit 60 in FIG. 2 are principally used here.

The recording unit 60 records patient information. FIG. 5 illustrates a data structure of patient information recorded in the recording unit 60. The patient information includes a patient ID space 112, a patient name space 114, a gender space 116, an age space 118, an admission date space 120, an expected discharge date space 122, a hospital days space 124, and a comment space 126. The patient ID space 112 records identification numbers assigned to patients, and the patient name space 114 records names of patients. The gender space 116 records the gender of patients, and the age space 118 records the age of patients. The admission date space 120 records dates when patients are admitted to a hospital; the expected discharge date space 122 records dates of expected discharge of patients; and the hospital days space 124 records the number of days for which each patient has been hospitalized. The comment space 126 records comments to patients. The patient information recorded in the recording unit 60 may includes information other than these pieces of information mentioned above. For example, a basic patient profile, such as family structure, occupation and hospital ward, a patient record, a lifestyle habit of each patient before admittance, a background to hospital visiting, a daily action, or a mental side of each patient may be added as the patient information.

The viewing preparation unit 44 displays the listing of patient information recorded in the recording unit 60. The input control unit 50 receives from the operation apparatus 62 an instruction to select a single patient from the patient information. Based on the instruction received by the input control unit 50, the management unit 56 selects patient information and nursing information for a single patient, from the recording unit 60.

Figure 6:
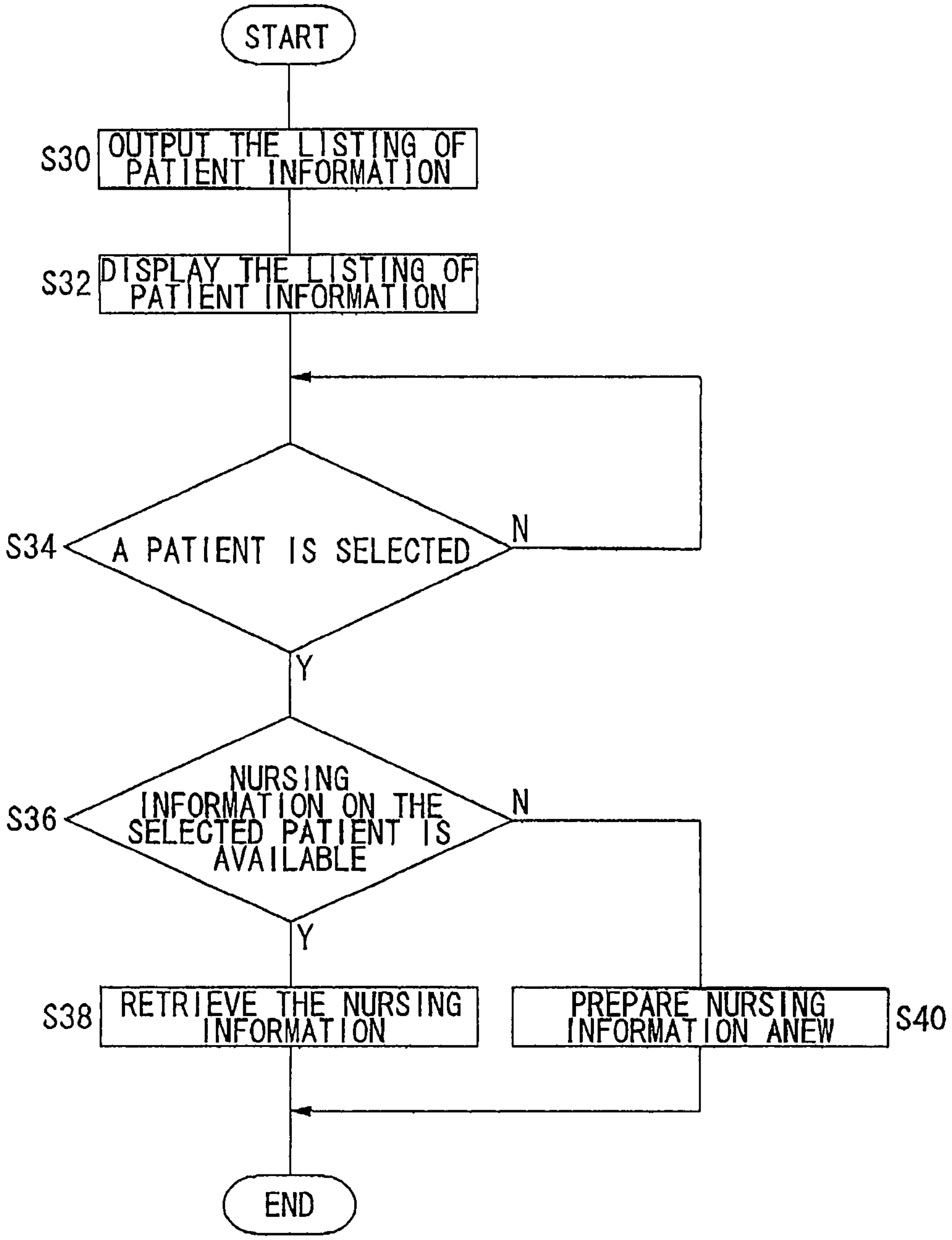
FIG. 6 is a flowchart showing a procedure for selecting patient information in a PC of FIG. 1.

FIG. 6 is a flowchart showing a procedure for selecting patient information in the PC 20. The management unit 56 outputs the listing of the patient information recorded in the recording unit 60 (S30). The viewing preparation unit 44 has the display apparatus 64 display the listing of the patient information (S32). FIG. 7 illustrates a screen, at a stage of patient selection, displayed on the display apparatus 64. Arranged on the screen are a patient selection button 200, a planning button 202, an order issuing button 204 and a recording/evaluation button 206. At a stage of patient selection, the patient selection button 200 is selected. The screen contains a patient's room space 208, a patient ID space 210, a patient name space 212, a gender space 214, an age space 216, an admission date space 218, an expected discharge date 220, a hospital days space 222, and a comment space 224. Such contents correspond to the patient information recorded in the recording unit 60.

Refer back to FIG. 6, if the patient has not been selected by the operation apparatus 62 (N of S34), a wait state continues until selection is done. If, on the other hand, the patient is selected (Y of S34), the input control unit 50 receives selection information. In FIG. 7, the nurse selects a single patient "Taro Tokyo" using the operation apparatus 62. Refer back to FIG. 6. If nursing information for the selected patient is available in the recording unit 60 (Y of S36), the management unit 56 will retrieve the corresponding nursing information (S38). If the nursing information for the selected patient is not available in the recording unit 60 (N of S36), the management unit 56 prepares new nursing information (S40).

An operation of the PC 20 structured as above is now described. The nurse decides on a patient to whom a nursing care is to be conducted, from the listing of patient information displayed on the display apparatus 64. The nurse operates the operation apparatus 62 and selects the patient thus decided. Then, nursing information for the patient selected is displayed on the display apparatus 64.

By employing the above structure, the patient to whom the nursing care is intended is selected from the listing displayed on a display apparatus, so that the selection processing can be done with ease. Also, since the patient to whom a nursing care is to be conducted is selected from the listing displayed on the display apparatus, the selection processing can be performed with accuracy. Also, the screen used for the management of nursing care and the screen used to select a patient are switched around by pressing a button, so that the switching of the both screens can be made easily.

3. Preparation of Nursing Problems and Nursing Care Plans

Preparation of nursing problems/nursing care plans corresponds to Step 12 and Step 14 of FIG. 4. The problems to be resolved here may be expressed as follows. It is desired that the preparation of nursing problems be made with ease and the preparation of nursing problems be made with accuracy, Also, it is desired that nursing problems corresponding respectively to patients be prepared. It is desired that the preparation of a nursing care plan be made with ease. It is desired that the preparation of a nursing care plan be made with accuracy. It is desired that nursing care plans corresponding respectively to patients be prepared. To prepare the nursing problems/nursing care plans, the viewing preparation unit 44, the display apparatus 64, the operation apparatus 62, the input control unit 50, the control unit 42, the management unit 56, the recording unit 60, the problem preparation supporting unit 30, the first database 32, the plan preparation supporting unit 34 and the second database 36 are principally used here.

The problem preparation supporting unit 30 supports the preparation of nursing problem items for patients. To support the preparation of nursing problem items, the problem preparation supporting unit 30 uses nursing problem database contained in the first database 32. FIG. 8 illustrates a data structure of the nursing problem database contained in the first database 32. The nursing problem database includes a diagnosis-and-treatment department space 130, a disease space 132, a nursing problem space 134, and a nursing problem code space 136. The diagnosis-and-treatment department space 130 records a plurality of diagnosis and treatment departments for medical services in a hospital. The plurality of diagnosis and treatment departments include "gastroenterology" and "pediatrics", for example. The disease space 132 records a plurality of diseases, to be treated by departments, for a plurality of diagnosis-and-treatment departments, respectively.

For example, diseases such as esophagitis and colon cancer are recorded in correspondence to the diagnosis and treatment department which is gastroenterology (or department of digestive organs) here. The nursing problem space 134 records a plurality of kinds of items, to be included in the nursing problems, corresponding respectively to a plurality of diseases. For example, "there is a risk of suffering from a hemorrhagic shock due to hematemesis or melena" and the like are recorded in response to the colon cancer. As identifiers, nursing problem codes are assigned respectively to a plurality of kinds of items to be included in the nursing problems. The nursing problem code space 136 records the nursing problem codes corresponding respectively to a plurality of kinds of items to be included in the nursing problems. As described above, the diagnosis and treatment departments, the diseases and the nursing problem items are brought into correspondence with one another. That is, the nursing problem database defines a plurality of kinds of items, to be included in the nursing problems, across a plurality of diagnosis and treatment departments. Hereinafter, a "diagnosis and treatment department" will be referred to also or simply as "department".

Refer back to FIG. 2. The problem preparation supporting unit 30 presents a plurality of kinds of items to the nurse in a unified manner, by way of the viewing preparation unit 44 and the display apparatus 64. Further, the problem preparation supporting unit 30 has the nurse select a nursing problem item or items via the operation apparatus 62 and the input control unit 50. Here, "in a unified manner" corresponds to putting together and arranging a plurality of kinds of items by department and patient and also corresponds to integrating a plurality of kinds of items into a predetermined category or categories. More specific explanation is as follows. The problem preparation supporting unit 30 presents a plurality of departments to the nurse by way of the viewing preparation unit 44 and the display apparatus 64, and then receives from the nurse a specification as to the selection of a department.

The problem preparation supporting unit 30 extracts from the first database 32 a plurality of patient names corresponding to the department selected by the nurse. Then the problem preparation supporting unit 30 presents the plurality of extracted patient names to the nurse via the viewing preparation unit 44 and the display apparatus 64. Further, the problem preparation supporting unit 30 receives from the nurse a specification as to the selection of a disease name. The problem preparation supporting unit 30 extracts from the first database 32 a plurality of kind's of items corresponding to the selected disease name and then presents the plurality of extracted items to the nurse via the viewing preparation unit 44 and the display apparatus 64. Finally, the problem preparation supporting unit 30 receives a specification as to the selection of an item from the nurse via the operation apparatus 62 and the input control unit 50 and then extracts from the first database 32 a nursing problem code corresponding to the item selected by the nurse. As a result of the above processing, the problem preparation supporting unit 30 outputs the prepared nursing problem code to the plan preparation supporting unit 34.

As described above, the first database 32 stores a plurality of kinds of items to be included in nursing problems, as fixed phrases, respectively. And the problem preparation supporting unit 30 has the nurse select any of the fixed phrases. Further, the problem preparation supporting unit 30 presents an open-ended entry space to the nurse. This open-ended entry space corresponds to a space provided for giving a comment to a fixed phrase. There are cases where a nursing problem item for a patient is not determined uniquely, in which case the comment is entered. The management unit 56 associates the comment in the open-ended entry space entered by the nurse with the selected fixed phrase. The thus associated comment in the open-ended entry space together with the fixed phrase is stored in the recording unit 60. That is, they are stored in the nursing problem space 102 of FIG. 3.

Refer back to FIG. 2. The plan preparation supporting unit 34 supports the preparation of nursing care plans by searching through a nursing care plan database included in the second database 36 based on the nursing problem codes prepared for patients. Here, the nursing care plan database includes nursing care plan items which are brought into correspondence in advance with a plurality of kinds of items to be included in the nursing problem, respectively. FIG. 9 illustrates a data structure of the nursing care plan database included in the second database 36. The nursing care plan database includes a nursing problem code space 140, a target space 142, and a plan space 144. The nursing problem code space 140 records nursing problem codes corresponding respectively to a plurality of items included in the nursing problem. The target space 142 records targets or objectives corresponding respectively to the nursing problem codes. For example, a statement like "Find the bleeding in early stages and prevent a critical shock state" is recorded as a target or objection. Also, it can be said that the targets and plans correspond to the nursing problem codes. The plans are classified into OP, CP and EP as described above.

As described above, the second database 36 stores nursing care plan items as fixed phrases, respectively. And the plan preparation supporting unit 34 has any of the fixed phrases selected according to the nursing problem code selected in the problem preparation supporting unit 30. Further, the plan preparation supporting unit 34 presents an open-ended entry space to the nurse. This open-ended entry space corresponds to a space provided for giving a comment to a fixed phrase. There are cases where a nursing problem item for a patient is not determined uniquely, in which case the comment is entered. The management unit 56 associates the comment in the open-ended entry space entered by the nurse with the selected fixed phrase. The thus associated comment in the open-ended entry space together with the fixed phrase is stored in the recording unit 60. That is, they are stored in the nursing care plan space 104 of FIG. 3.

Refer back to FIG. 2. The viewing preparation unit 44 displays GUIs to be presented respectively for the problem preparation supporting unit 30, the plan preparation supporting unit 34 and the display of implementation results and evaluations described later, on the screen of the display apparatus 64. Hereinafter, the GUI to be presented for the problem preparation supporting unit 30 will be called a "problem list"; the GUI to be presented for the plan preparation supporting unit 34 will be called a "nursing care plan"; and the GUI to be presented for the display of implementation results and evaluations will be called a "nursing record". Here, the management unit 56 operates to perform the "nursing record". The communication unit 52, the input control unit 50 and the operation apparatus 62 are used for the entry of the nursing records. The viewing preparation unit 44 is so structured that the problem list, the nursing care plan and the nursing record are all displayed within a single screen. That is, provided is a screen such that the nursing problem, the nursing care plan, the nursing result and the evaluation can be read through by the nurse.

The viewing preparation unit 44 has a GUI, to be presented for the display of evaluations in the nursing record, displayed on a part of area where a GUI to be presented for the display of implementation results is displayed. That is, presented is a screen where the correspondence between an implementation result and an evaluation is clarified. Further, the evaluation also contains information on the current status of a patient, and an area for displaying a GUI to be presented for the display of an evaluation is provided in a manner that it is divided by an area corresponding to information on a patient condition and an area corresponding to an evaluation to information other than the information on a patient condition.

Here, the evaluation corresponds to a "SOAP format" which is one of recording modes for recording a process or progress. "S (subjective)" corresponds to subjective actions or appeals by patients, which are, for example, direct remarks by patients regarding nursing problems or those according thereto. That is, S may be said to represent subjective information about patients. For example, S is "want to have the body wiped" or "change into pajamas". "O (objective)" corresponds to numerical values such as laboratory results and vitals or contents based on an objective observation by a nurse and experiments. That is, O may be said to represent objective information about patients. For example, O is "at a doctor's round visit, a lower limb/upper limb and a precordial region were not wiped and consequently the skin is a bit sticky" or "cleanliness activity cannot be conducted by his/her own ability and thus he/she cannot change the clothes by himself/herself because of paralysis in left upper and lower limbs together with movement restrictions as a result of a treatment".

"A (assessment)" corresponds to nurses' judgment to S or O or thought processes. That is, A may be said to represent an evaluation by a nurse. For example, A is "with skin contamination/moistness left unattended, a risk of occurrence of decubitus increases". "P (plan)" corresponds to a future schedule or plan based on A. For example, P is "(1) Perform a bed bath of a lower limb/upper limb and a precordial region; (2) Observe the skin condition; and (3) Change underwear/nightwear after the bed bath". The information on a patient condition corresponds to S and O in the SOAP format, whereas an evaluation to information other than the information on a patient condition corresponds to A and P in the SOA format.

In cooperation with the operation of the problem preparation supporting unit 30, the viewing preparation unit 44 defines, on a screen, a first area where a plurality of departments are to be displayed, a second area where a plurality of patients are to be displayed, and a third area where a plurality of kinds of items to be included in a nursing problem are to be displayed. The first to the third area are not overlapped with one another on the screen, and the size, position and the like of each area may be arbitrary. To clarify the correspondence among departments, diseases and items, the first to the third area may be arranged adjacent to each other. The viewing preparation unit 44 displays a plurality of departments in the first area. When any of a plurality of departments displayed in the first area is selected by a nurse via the operation apparatus 62, the viewing preparation unit 44 displays a plurality of patients associated with the selected department, in the second area. When any of the plurality of patients displayed in the second area is selected by the nurse, the viewing preparation unit 44 displays a plurality of kinds of items associated with the selected patient, in the third area.

In cooperation with the plan preparation supporting unit 34, the viewing preparation unit 44 displays information in the nursing care plan displayed on the screen. That is, after the plan preparation supporting unit 34 conducts a search through the second database 36 based on nursing problem items prepared for patients, the viewing preparation unit 44 displays search results in the area allotted to the nursing care plan.

Figure 10:
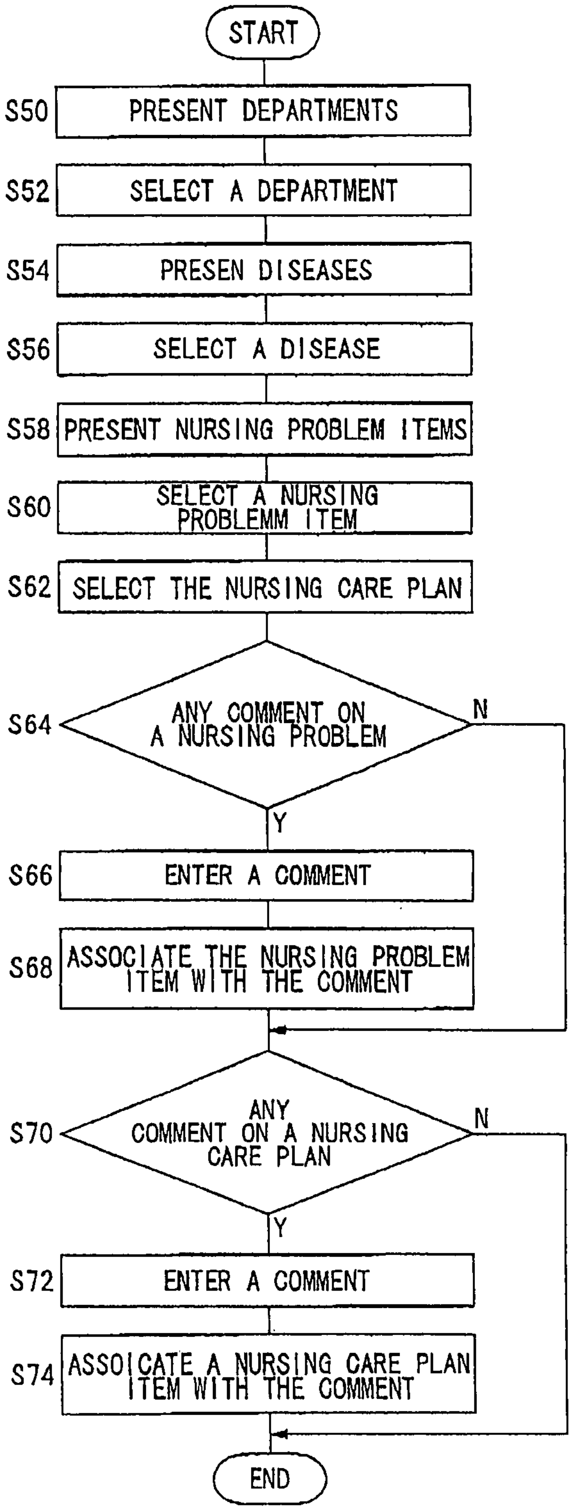
FIG. 10 is a flowchart showing a procedure for preparing nursing problems and nursing care plans in a PC of FIG. 2.
Figure 11:
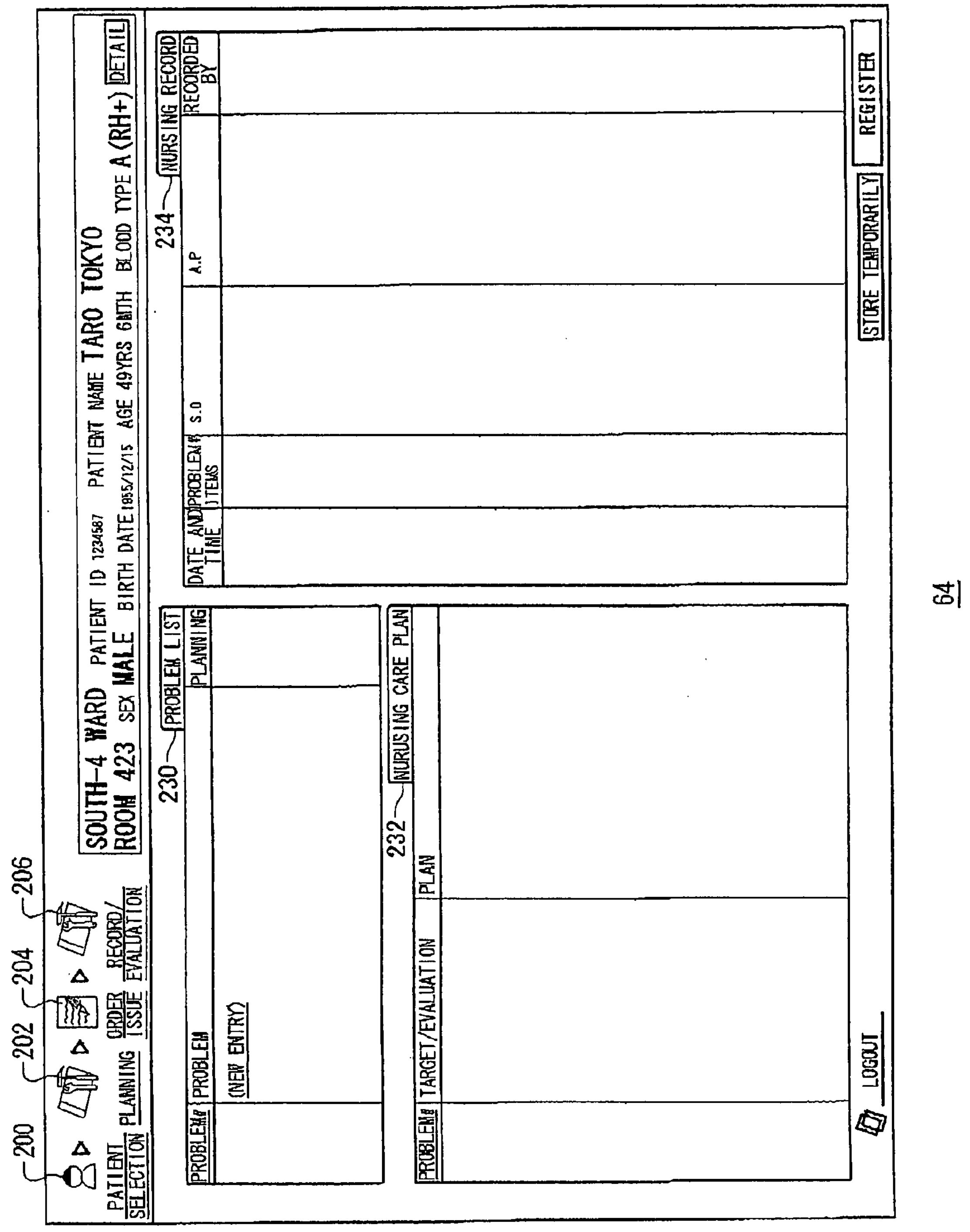
FIG. 11 illustrates an initial screen, at a planning stage displayed, on a display apparatus of FIG. 2.

FIG. 10 is a flowchart showing a procedure for preparing nursing problems and nursing care plans in the PC 20. The viewing preparation unit 44 has the display apparatus 64 display an initial screen. FIG. 11 illustrates an initial screen, at a planning stage, displayed on the display apparatus 64. Similar to FIG. 7, a patient selection button 200 to a recording/evaluation button 206 are displayed but the planning button 202 is selected here. Also, a problem list space 230, a nursing plan space 232, a nursing record space 234 are displayed on the screen, and these correspond to a problem list, a nursing care plan and a nursing record, respectively. As shown in FIG. 11, the problem list, the nursing care plan and the nursing record are so arranged as to be read through, Refer back to FIG. 10. The problem preparation supporting unit 30 presents a plurality of departments in the display apparatus 64 (S50). A department is selected by the nurse via the operation apparatus 62 (S52).

Figure 12:
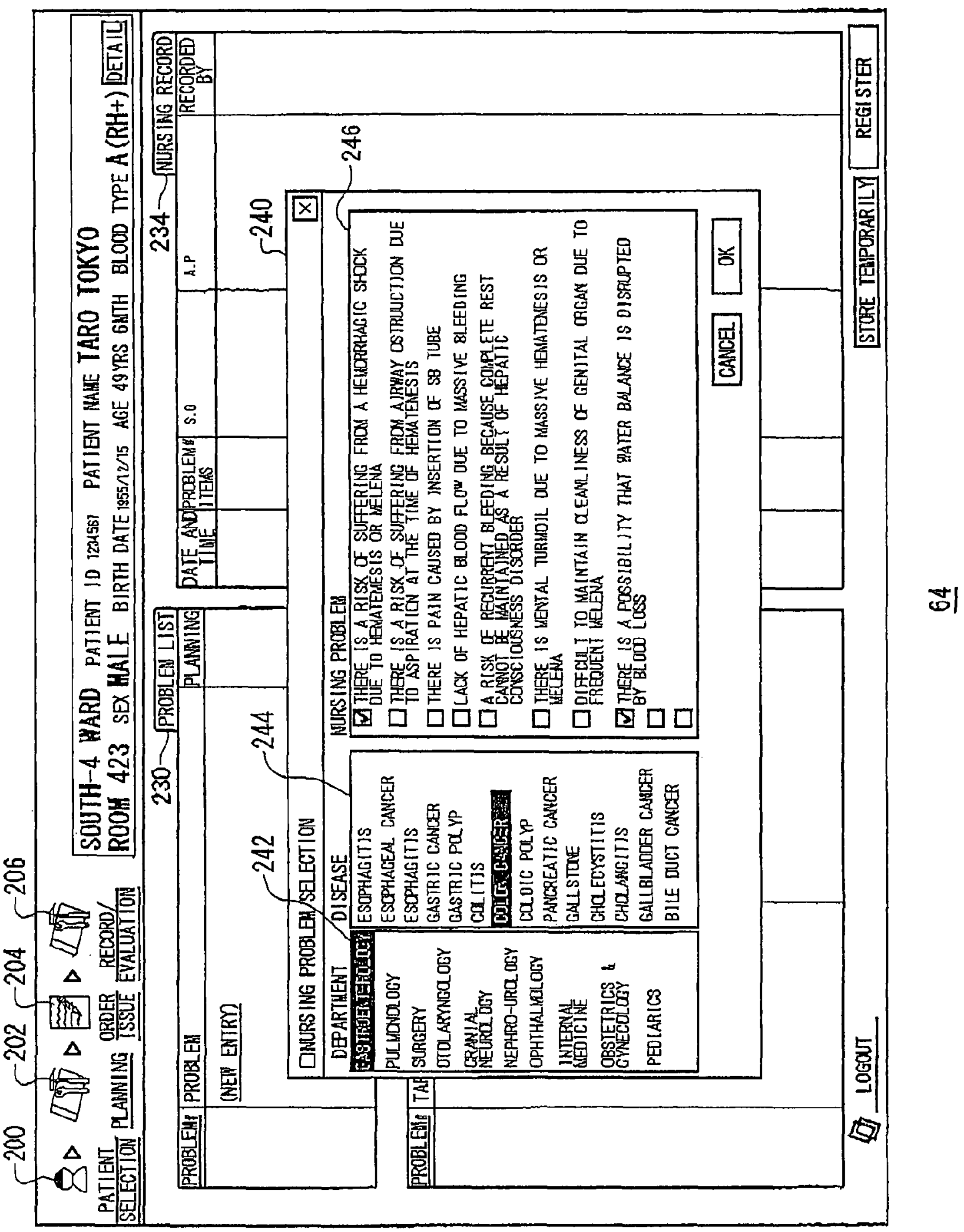
FIG. 12 illustrates a screen for a nursing problem selection displayed on a display apparatus of FIG. 2.

Consequently, the problem preparation supporting unit 30 presents a plurality of patients to the display apparatus 64 (S54) A patient is selected by a nurse using the operation apparatus 62 (S56). Further, the problem preparation supporting unit 30 presents to the display apparatus 64 a plurality of kinds of items for the nursing problems (S58). An item or items are selected by the nurse via the operation apparatus 62 (S60). FIG. 12 illustrates a screen for the nursing problem selection displayed on the display apparatus 64. A nursing problem selection window 240 is displayed in the center of the screen. The nursing problem selection window 240 contains a department space 242, a patient space 244 and a nursing problem space 246, which correspond respectively to the above-described first to third areas.

FIG. 12 corresponds to Step 60 of FIG. 10. In the example shown in FIG. 12, "gastroenterology" was already selected in the department space 242 and "colon cancer" was already selected in the disease space 244. Any of the nursing problem selection window 240 is already selected in FIG. 12. At the stage of Step 50, nothing is displayed in the disease space 244 and the nursing problem space 246. That is, once an option is selected, a subsequent option is displayed.

Figure 13:
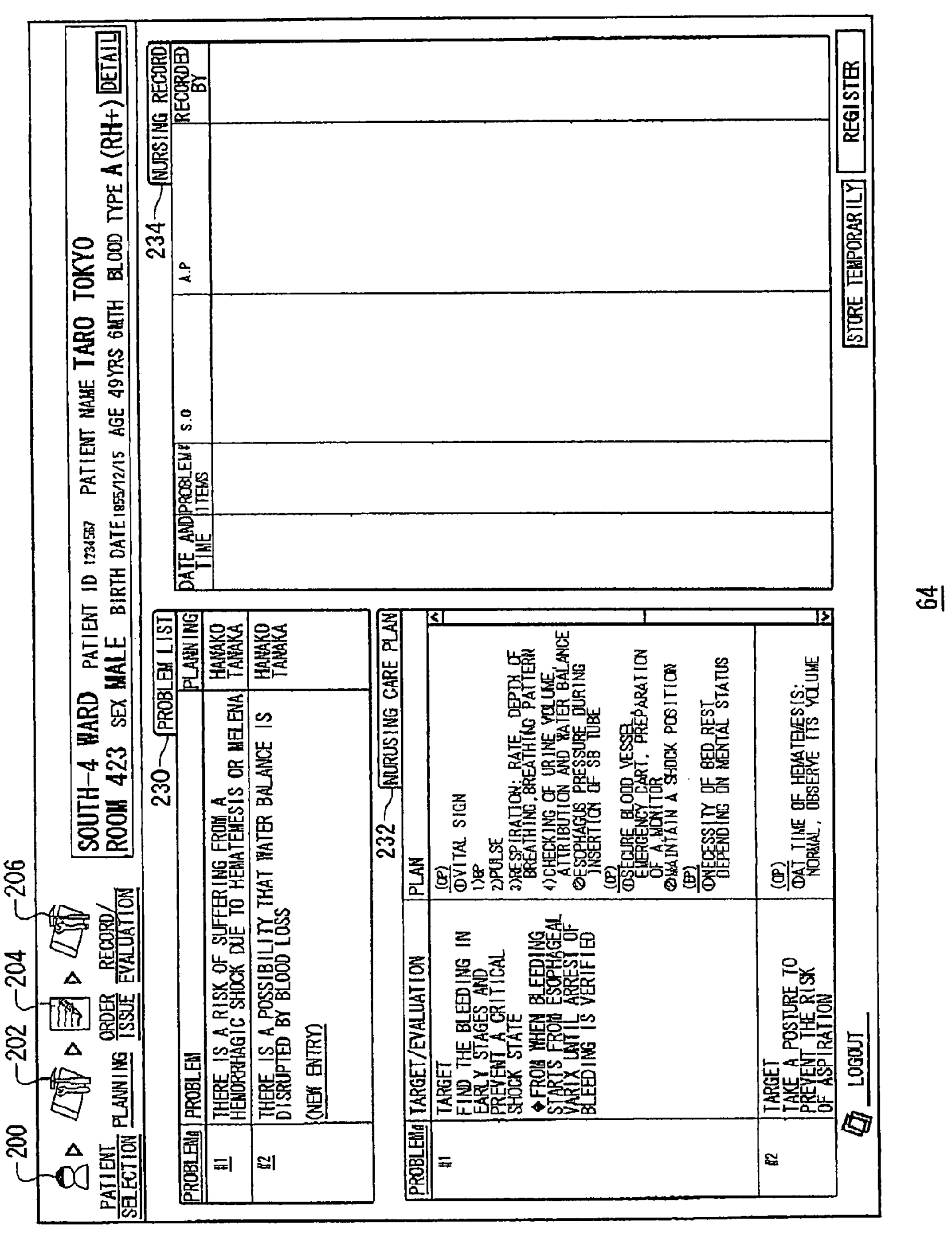
FIG. 13 illustrates a screen displayed after a nursing care plan displayed on a display apparatus of FIG. 2 has been entered.

Refer back to FIG. 10. When a nursing problem item is selected, the plan preparation supporting unit 34 selects the nursing care plan while conducting a search through the second database 36 (S62). FIG. 13 illustrates a screen displayed after a nursing care plan displayed on the display apparatus 64 has been entered. Nursing problem items are displayed in the problem list space 230, and nursing care plan items are displayed in the nursing care space 232. Here, "#1" and so forth correspond to the identifiers used to identify a set of items that are brought into correspondence with one another among the nursing items included in the nursing care plan, the implementation results and the evaluations. Refer back to FIG. 10. The management unit 56 prompts the entry of a comment on the nursing problem; and if there is a comment to the nursing problem (Y of S64), the nurse will enter the comment using the operation apparatus 62 (S66).

Figure 14:
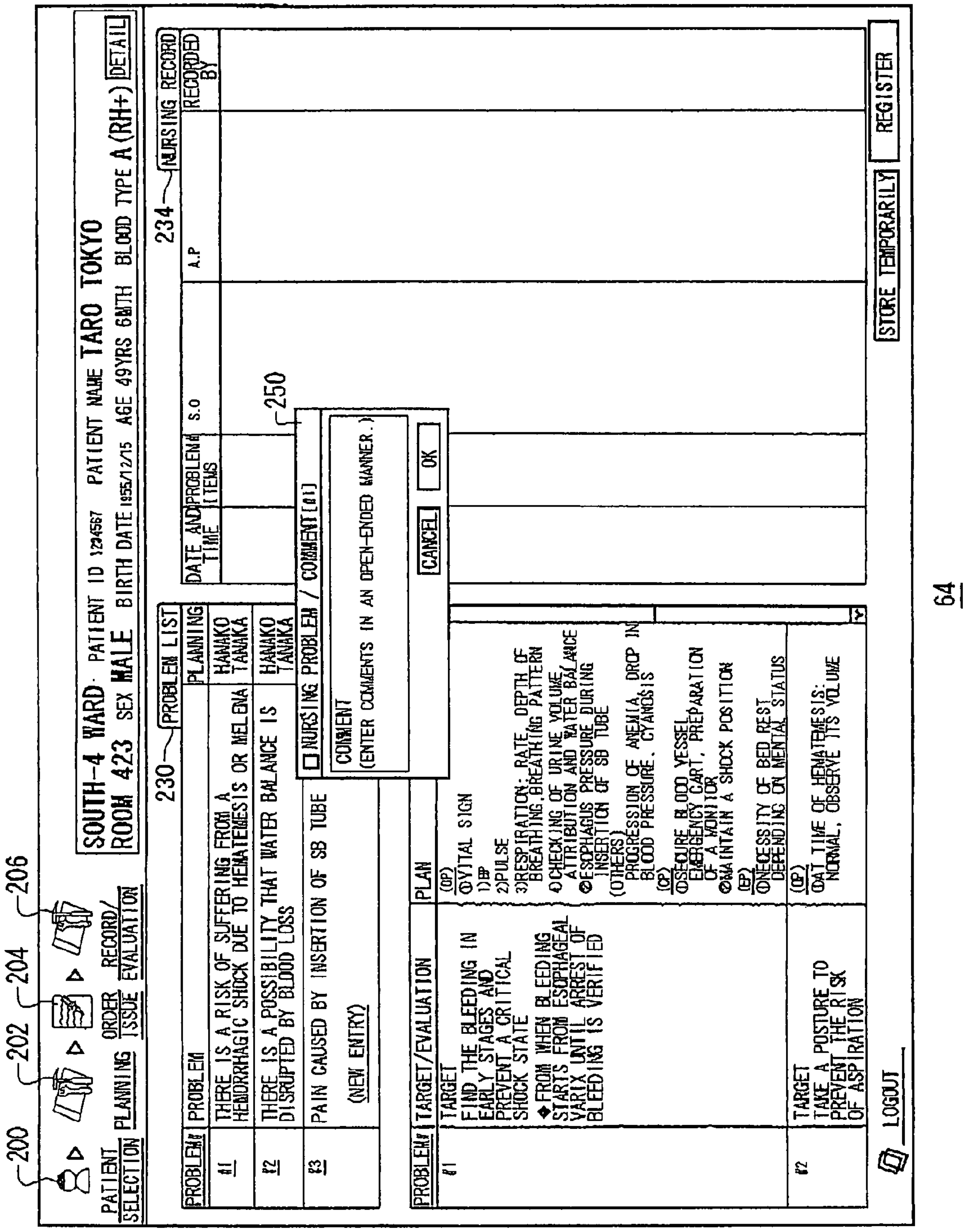
FIG. 14 illustrates an additional window for a comment on a nursing problem displayed on a display apparatus of FIG. 2.
Figure 15:
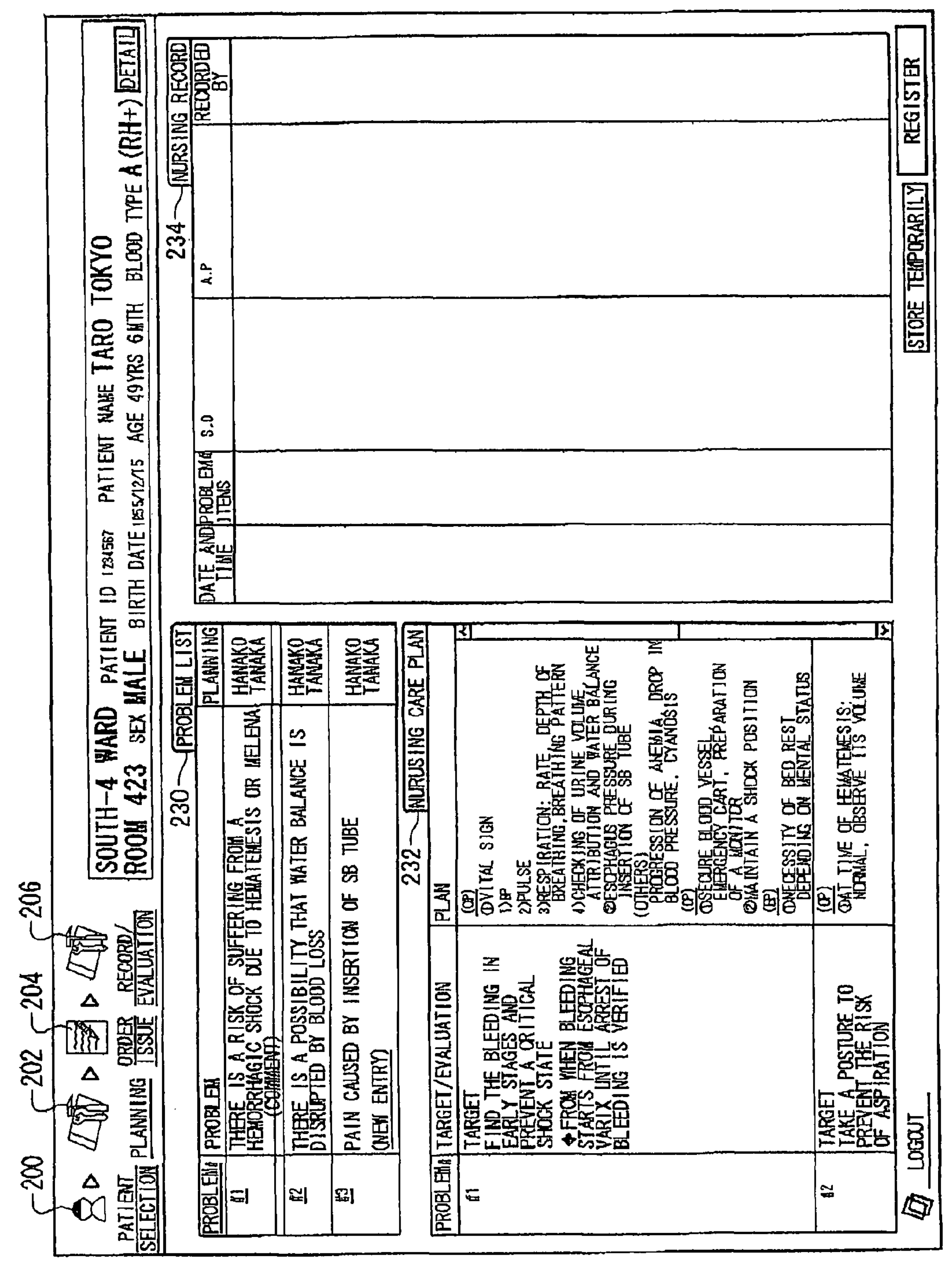
FIG. 15 illustrates a screen displayed after a comment on a nursing problem displayed on a display apparatus of FIG. 2 has been entered.

The management unit 56 associates nursing problem items with the comment (S68) and then records them in the recording unit 60. If there is no comment on a nursing problem (N of S64), such processing will not be performed. FIG. 14 illustrates an additional window for a comment on the nursing problem displayed on the display apparatus 64. A nursing problem open-ended entry window 250 is displayed in the center part of a screen. The nurse enters a comment into the nursing problem open-ended entry window 250. FIG. 15 illustrates a screen displayed after the comment on the nursing problem displayed on the display apparatus 64 has been entered. The comment is entered in the space provided for the problem "#1" in the problem list space 230.

Figure 16:
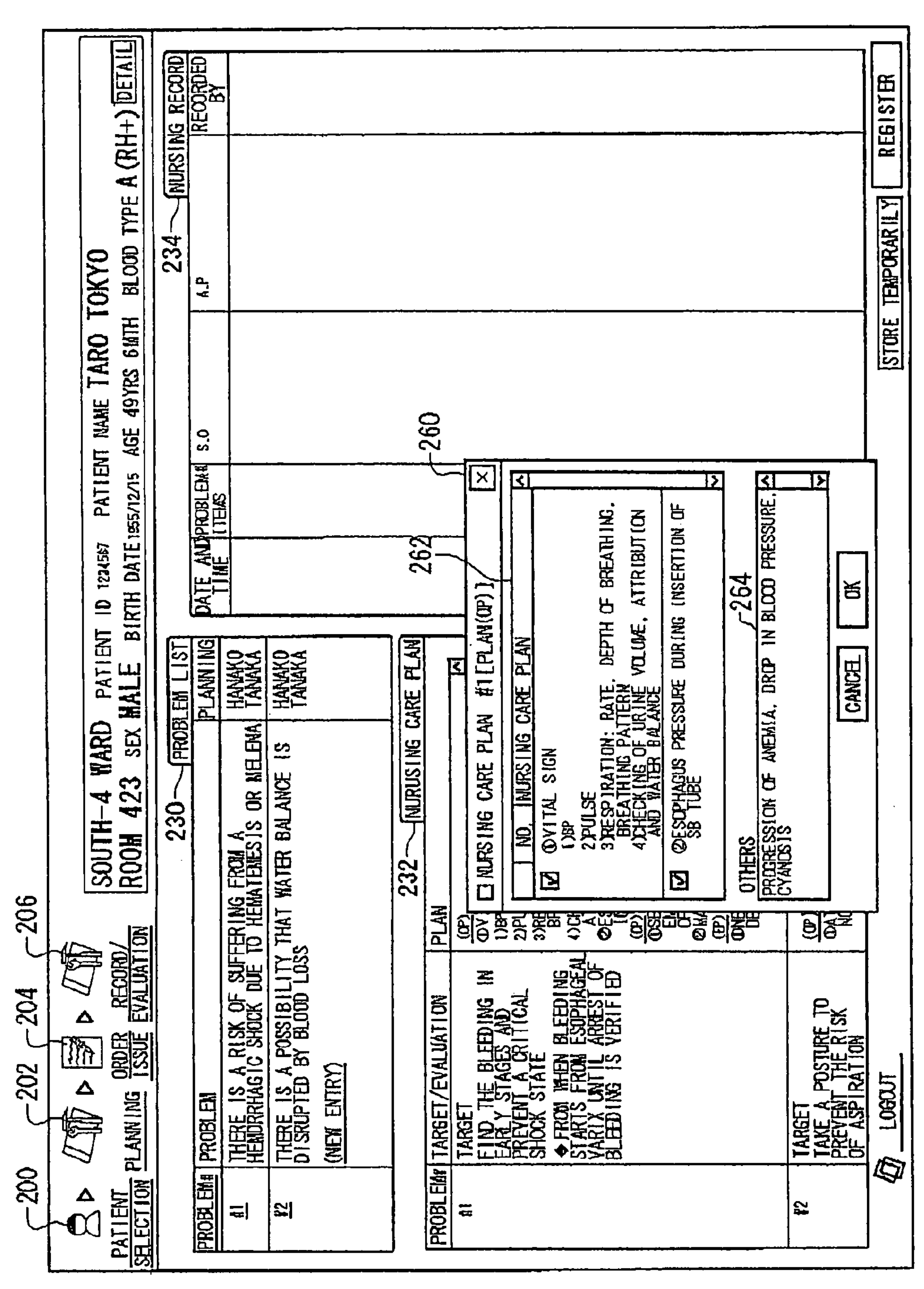
FIG. 16 illustrates an edit screen of a nursing care plan displayed on a display apparatus of FIG. 2.
Figure 17:
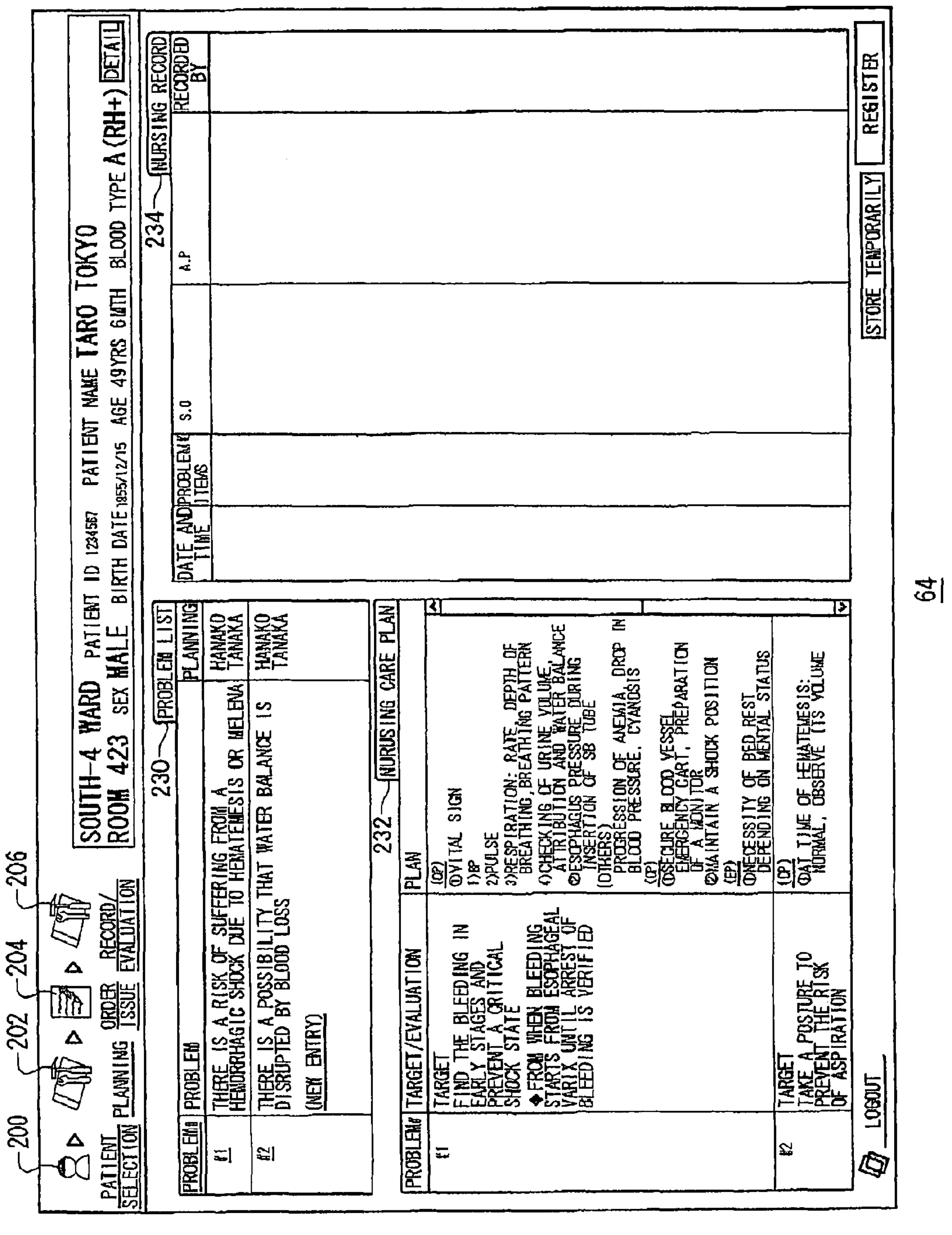
FIG. 17 illustrates a screen after a nursing care plan displayed on a display apparatus of FIG. 2 has been edited.

Refer back to FIG. 10. If there is any comment on a nursing care plan (Y of S70), the nurse will enter the comment using the operation apparatus 62 (S72). The management unit 56 associates nursing plan items with the comment (S74) and then records them in the recording unit 60. If there is no comment on a nursing care plan (N of S70), such processing will not be performed. FIG. 16 illustrates an additional window for a comment on the nursing problem displayed on the display apparatus 64. A nursing care plan edit window 260 is displayed in the center part of a screen. The nursing care plan edit window 260 includes a typical statement space 262 and an open-ended entry space 264. The nurse edits the already entered nursing care plan items by entering a predetermined specification to the typical statement space 262. Also, the nurse enters a comment into the open-ended entry space 264. FIG. 17 illustrates a screen displayed after the nursing care plan displayed on the display apparatus 64 has been edited. The comment is entered in the plan for "#1" in the nursing care plan space 232.

An operation of the PC 20 structured as above will now be described. From among a plurality of kinds of items to be included in the nursing problem displayed on the display apparatus 64, the nurse selects via the operation apparatus 62 a nursing problem item or items which is/are to fall under the relevant category. The PC 20 selects a nursing care plan or plans corresponding to the selected nursing problem item or items, and displays it on the display apparatus 64. The nurse enters a comment to the nursing problem and a comment to the nursing care plan using the operation apparatus 62. The PC 20 records the prepared nursing problem items, the nursing care items and the comments thereto by bringing them into correspondence with one another.

By employing the above-described structure, when the nursing problems are to be prepared, selection is made from predefined items, thus making the preparation of nursing problems easier. Mistakes made in the preparation of nursing problems can be reduced. The nursing problems are defined through a plurality of stages. Thus, if one of the plurality of stages is selected, the candidates for the selection for the next stage will be displayed. As a result, the selection processing becomes clear and mistakes made in the selection can be reduced. Since a plurality of stages are so arranged as to be positioned adjacent to one another on a single screen, the correspondence therebetween can be clarified. When the nursing problems are to be prepared, not only the predefined items but also comments may be added, so that the nursing problems suited respectively for patients can be prepared.

Since a nursing care plan item is selected from among the nursing problem items by referring to a database where the nursing problem items and the nursing care plans are brought into correspondence with each other, the nursing care plan can be prepared with ease. Since the nursing care plans are defined beforehand, mistakes made in the preparation of the nursing care plans can be reduced. When the nursing care plans are to be prepared, not only the predefined items but also comments may be added, so that the nursing care plans suited respectively for patients can be prepared. Since nursing problems, nursing care plans, implementation results and evaluations are arranged on a single screen, the relationship among them can be clarified. Since the correspondence among them is clarified, the accuracy in conducting the nursing actions can be enhanced. Since the evaluation is displayed in a part of area where the implementation result is to be displayed, the relationship between the implementation result and the evaluation can be clarified. Since the information on the current status of a patient and other evaluations are displayed in an area where the evaluation is to be displayed in a manner that they are brought into correspondence with each other, the relationship therebetween can be clarified.

4. Oder Issuance

The issuing of orders corresponds to Step 16 of FIG. 4. Here the problems to be resolved here may be indicated as follows. It is desired that mistakes in the preparation of order be minimized. It is desired that the processing amount for the issuing of orders be reduced. It is also desired that the mistakes made in conducting the nursing actions be reduced.

A description is given of the order issuance before describing a specific structure thereof. FIG. 18 is a schematic view showing an order issuance processing in the nursing information management system 10. FIG. 18 illustrates a case where an order for injection is issued as an order issuance. The nurse prepares an order (S80) and registers the order (S82). In the case of injection, when the order has been registered, the processing branches out into the following processings. A first processing specifies to a not-shown ward system the reception of a specification in the ward (S84). The reception of a specification is done by the nurse. A second processing specifies for a not-shown pharmaceutical division system to dispense and pay out medicines (S86). The dispensing and paying out of medicines is done by a pharmacist.

A third processing specifies to a not-shown ward system the mixed injection of medicines in the ward (S88). The mixed injection is also called "mixing". The mixed injection is performed by the nurse. A fourth processing specifies to the nursing information management system 10 the start of injection to a patient in the ward (S90). A fifth processing specifies to the nursing information management system 10 the termination of injection to a patient in the ward (S92). The injection is performed by the nurse. Here, the injection includes both intravenous injection by drip and one-shot injection. In the case of intravenous injection by drip, the administration is done spending a long duration of time, so that a work for the start of the dosing treatment and a work for the termination thereof generally differ from each other. In the case of one-shot injection, the dosing treatment can be terminated in a single action, so that the start of the dosing treatment and the termination thereof are done almost simultaneously.

To issue orders, the viewing preparation unit 44, the display apparatus 64, the operation apparatus 62, the input control unit 50, the control unit 42, the management unit 56, the recording unit 60, the specification unit 38, the third database 40 and the communication unit 52 in FIG. 2 are principally used.

Figure 19:
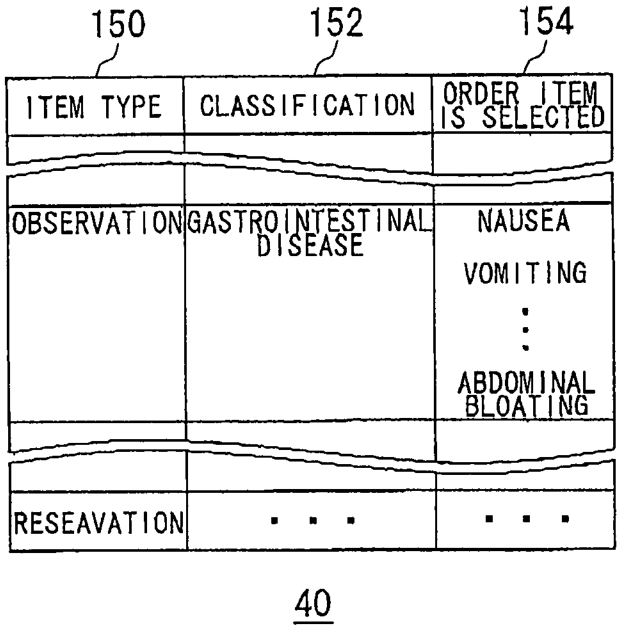
FIG. 19 illustrates a data structure of a database for use in orders included in a third database of FIG. 2.

The specification unit 38 supports the generation of orders for a specification, based on the nursing items, in an area of screen displayed by the viewing preparation unit 44. For the purpose of supporting the generation of orders, the specification unit 38 uses a database for use in orders included in the third database 40. FIG. 19 illustrates a data structure of the order database included in the third database 40. The database for use in orders includes an item type space 150, a classification space 152 and an order item space 154. The database for use in order is defined in a manner such that a plurality of classifications defined in the classification space 152 are associated respectively with those in the item type space 150 and a plurality of order items defined in the order item space 154 are associated respectively with those in the classification space 152.

The item type space 150 defines the type of an order. Here, the types of orders include "observation", "care", "guidance", "supervisory measures", "others" and "reservation". The classification space 152 defines the classification of diseases, Here, the classification of diseases includes "gastrointestinal disease", "cardiovascular disease" and so forth. The order item space 154 defines the contents of orders. Here, the contents of orders include "nausea", "vomiting" and so forth. Such a database for use in orders is displayed on the display apparatus 64 by the viewing preparation unit 44, and the nurse selects a predetermined item or items from the database for use in orders by referring to the nursing items. For instance, if the nursing items relate to a gastrointestinal disease, the nurse will select a gastrointestinal disease from the classification space 152.

Refer back to FIG. 2, the above-described selection by the nurse is received by the operation apparatus 62 and the input control unit 50. The orders generated are recorded in the recording unit 60. The specification unit 38 displays, on the display apparatus 64, the contents indicating that the generated orders shall be transmitted. Thereafter, if the specification unit 38 receives a confirmed operation from the nurse via the operation apparatus 62, the specification unit 38 will output the orders to the communication unit 52. The orders are also sent to the PDA 22 via the server 12.

Figure 20:
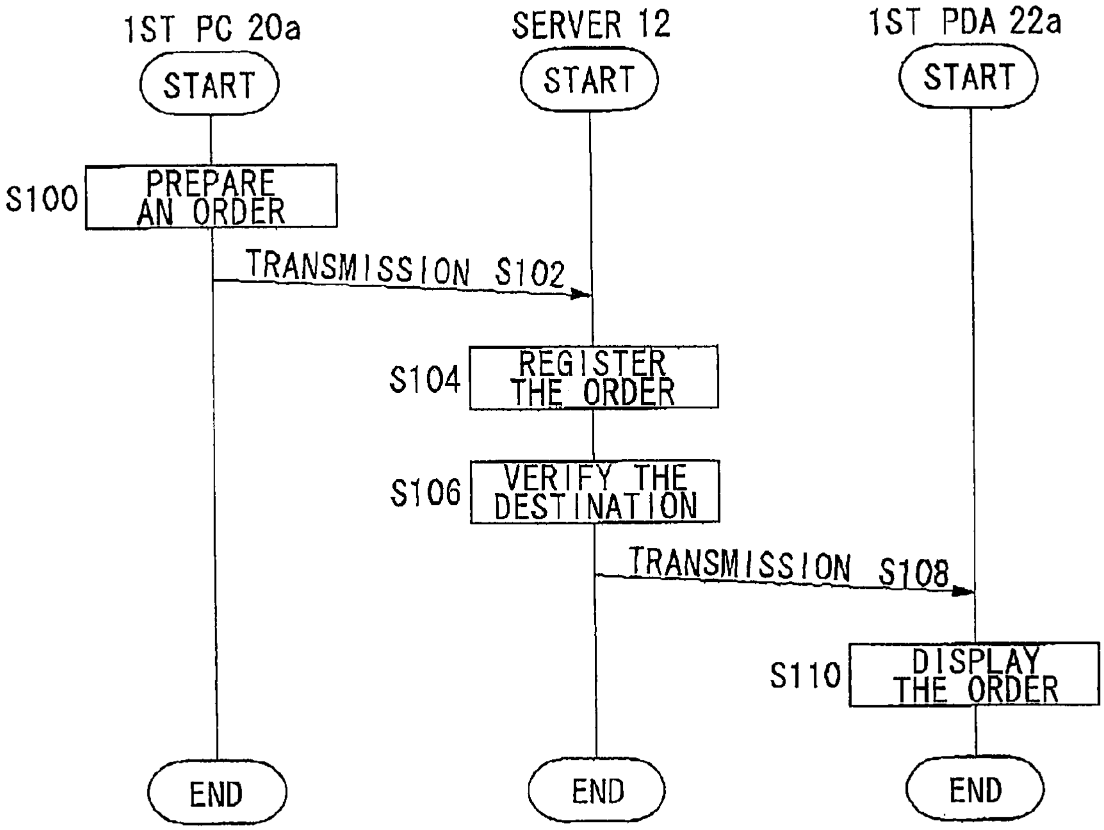
FIG. 20 is a sequence diagram showing a procedure for processing the issuance of orders in a nursing information management system of FIG. 1.

FIG. 20 is a sequence diagram showing a procedure for processing the issuance of orders in the nursing information management system 10. The nurse prepares orders in the first PC 20*a* (S100). Based on the specification of the order issuance by the nurse, the first PC 20*a* transmits the prepared orders to the server 12 (S102). The server 12 registers the orders (S104). Also, the server 12 verifies the destinations to which the registered order are to be transmitted (S106). As a result, suppose that the destination is the first PDA 22*a*. Then, the server 12 sends the registered order to the first PDA 22*a* (S108). The first PDA 22*a* displays the received order on a not-shown display (s110).

Figure 21:
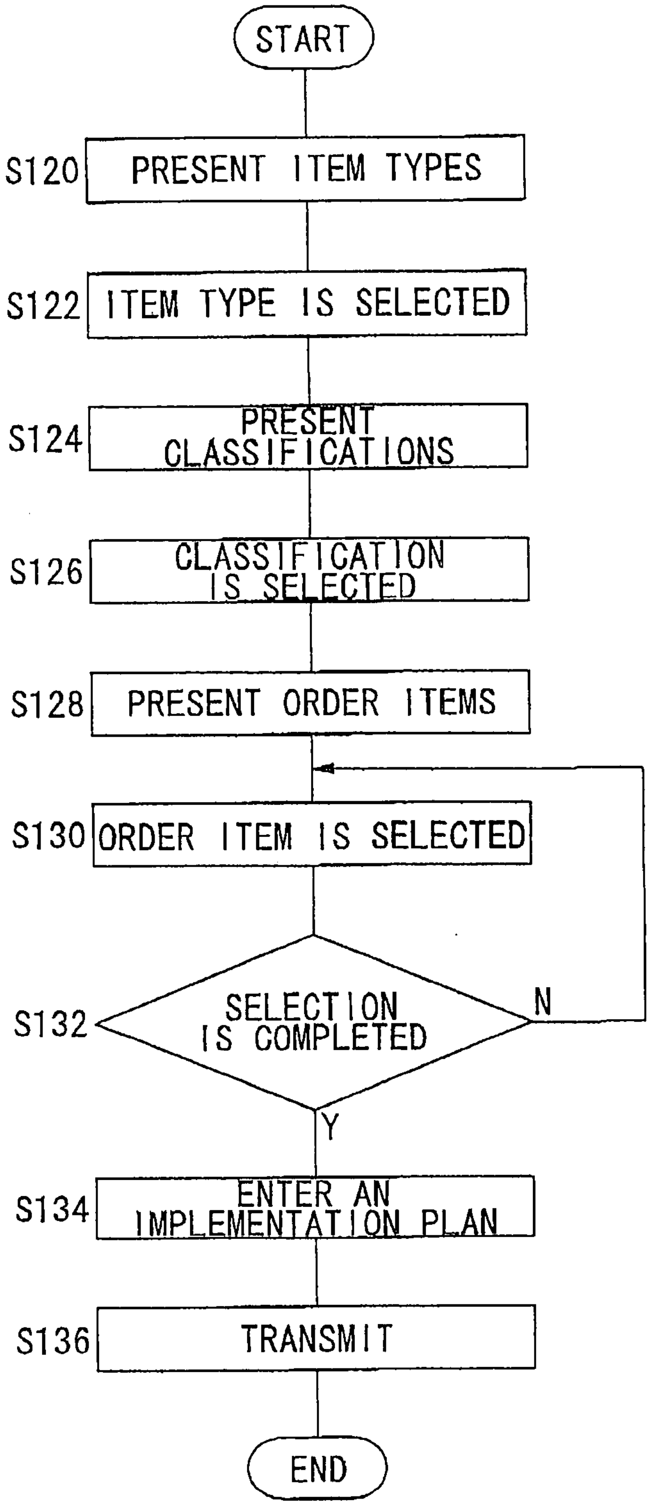
FIG. 21 is a flowchart showing a procedure for processing the issuance of orders in a PC of FIG. 2.

FIG. 21 is a flowchart showing a procedure for processing the issuance of orders in the PC 20. The specification unit 38 has the display apparatus 64 present the item types, by referring to the third database 40 (S120). A item type is selected by the nurse via the operation apparatus 62 (S122). The specification unit 38 receives a specification of the selection. The specification unit 38 has the display apparatus 64 present the classifications, by referring to the third data base 40 (S124). A classification is selected by the nurse via the operation apparatus 62 (s126). The specification unit 38 receives a specification of the selection. The specification unit 38 has the display apparatus 64 present the order items, by referring to the third database 40 (S128). An order item is selected by the nurse via the operation apparatus 62 (S130).

Figure 22:
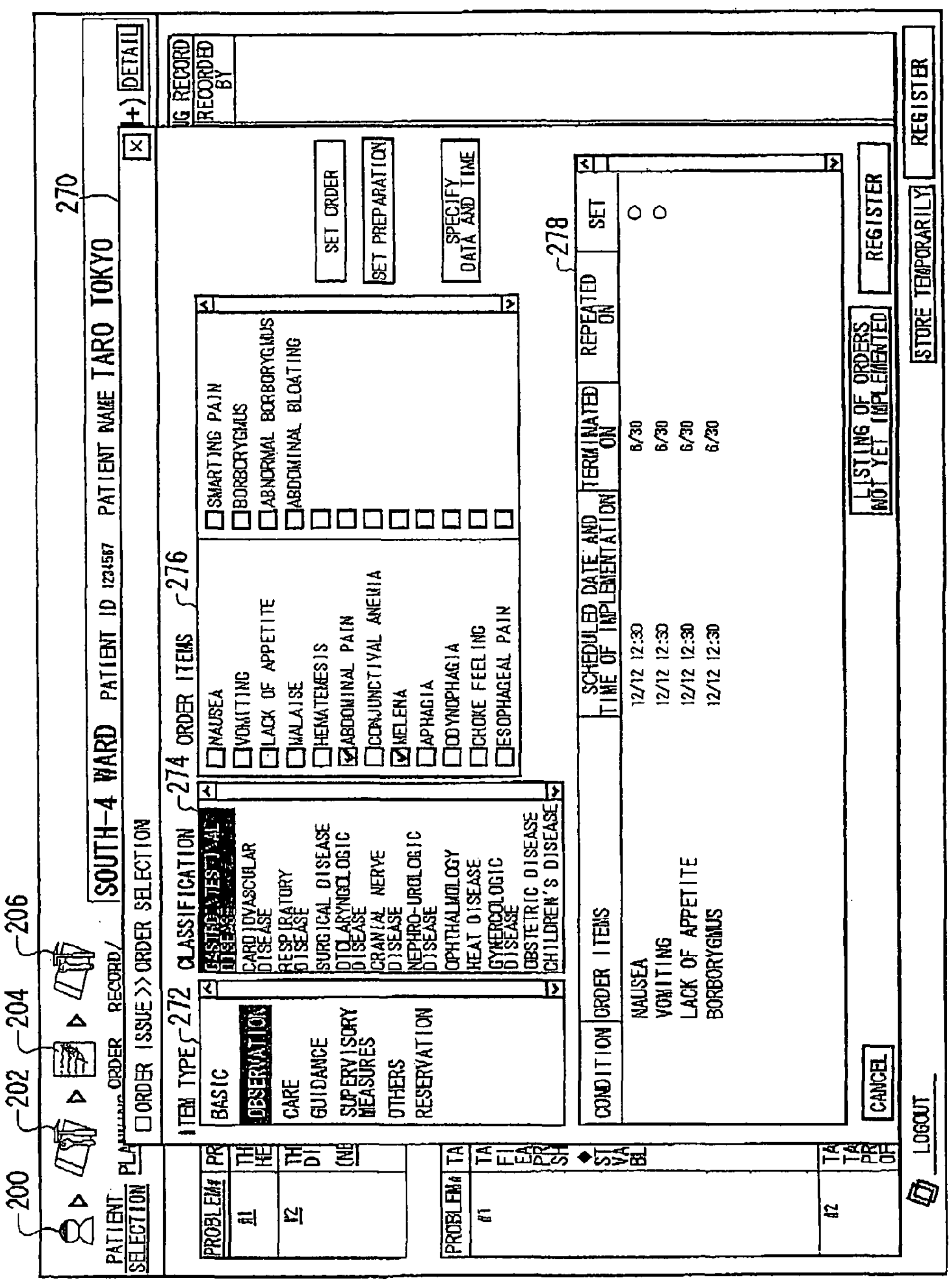
FIG. 22 illustrates a screen displayed on a display apparatus of FIG. 2 at a stage of order issuing.

The specification unit 38 receives a specification of the selection. If the selection of an order item has not been completed (N of S132), the processing of Step 130 is repeated. If, on the other hand, the selection of an order has been completed (Y of S132), the nurse enters a plan for implementation using the operation apparatus 62 (S134). The specification unit 38 receives the entered plan for implementation. FIG. 22 illustrates a screen displayed on the display apparatus 64 at a stage of order issuing. FIG. 22 corresponds to Step 134 of FIG. 21. Though the patient selection button 200 to the record/evaluation button 206 are displayed in FIG. 22, the order issue button 204 is selected this time. An order issue window 270 is displayed in the center of the screen. The order issue window 270 includes an item type space 272, a classification space 274, an order item space 276 and a plan space 278. The item type space 272, the classification space 274 and the order item space 276 correspond respectively to the item type space 150, the classification space 152 and the order item space 154 of FIG. 19.

The plan space 278 corresponds to a plan for implementation. Here, if at a stage of selecting any from the item type space 272 the contents of the classification space 274 and the order item space 276 are not displayed and any from the item type space 272 is selected, the contents of the classification space 274 will be displayed. That is, if the selection is made at a predetermined option in the order of the item type space 272, the classification space 274 and the order item space 276, options following them are displayed. Refer back to FIG. 21. The specification unit 38 combines the selected item type, classification, order item and plan for implementation so as to turn them into an order. As the specification unit 38 receives a specification of the order via the operation apparatus 62 from the nurse, the communication unit 52 transmits the order to the server 12 (S136).

An operation of the nursing information management system 10 structured as above is now described. Using the operation apparatus 62, the nurse prepares orders by referring to the nursing items displayed on the display apparatus 64. If the prepared order is fine, the nurse enters, using the operation apparatus 62, a check indicating that the order has been verified. The PC 20 sends the order to the server 12. The order is also sent to the PDA 22.

By employing the above-described structure, the nurse prepares the orders by referring to a nursing care plan displayed on the screen. Thus the occurrence of mistakes in the preparation of orders can be reduced. Also, the transmission of the prepared orders achieves the registration of them in the server, thus unifying the preparation of orders and the registration thereof. Since the preparation of orders and the registration thereof can be unified, the processing load in the issuance of orders can be reduced. If the orders are transmitted to a server corresponding to other systems, the issuance of orders can be integrated with other systems. Since verification by the nurse is done at the time of sending the order, a prepared order containing any error can be corrected. Since the transmitted order is sent to the PDA carried by the nurse, the nurse can verify the contents of the order through his/her PDA. Also, the occurrence of mistakes in conducting nursing actions can be reduced.

5. The Recording and Displaying of Implementation Results

The recording and displaying of implementation results corresponds to Step 20 of FIG. 4. The problems to be resolved here may be expressed as follows. It is desired that when displaying the implementation results, the listing of the implementation results be displayed even though a display area available is limited. It is desired that the verification required by a nurse be made with ease. To record and display the implementation results, the viewing preparation unit 44, the display apparatus 64, the control unit 42, the management unit 56, the recording unit 60, the communication unit 52, the storage 48 and the selector 46 are principally used here. It is assumed that the nurse performs a nursing care action in Step 18 of FIG. 4. The nurse enters the implementation results of the nursing care actions into the PDA 22. The PDA 22 transmits the received implementation results to the PC 20.

The communication unit 52 receives the implementation results of the nursing items for patients. The received implementation results may be a result for a single nursing item or that for a plurality of nursing items. In the latter case, the implementation result includes body temperature and urine volume, for example. As information attached to or accompanied by the implementation result, the communication unit 52 receives also information on a person, who has performed a nursing care action, and time at which the nursing care action was implemented (hereinafter this information will be referred to as "added information"). The communication unit 52 outputs the received implementation result and the added information to the recording unit 60. The recording unit 60 records the inputted implementation results and the added information.

The storage 48 stores, in advance, predetermined conditions used in the selection unit 46. Though the details will be discussed later, the selector 46 selects at least part of implementation results recorded in the recording unit 60, and displays the selected implementation result on the display apparatus 64. The storage 48 stores conditions that serve as criteria for the selection in the selector 46. Now, if there are a plurality of kinds of implementation results in the implementation results in the recording unit 60, the storage 48 stores conditions corresponding respectively to the plurality of kinds of nursing items. For instance, those conditions are a condition for temperature and a condition for urine volume, which are conditions for a nursing item to be displayed on the display apparatus 64. The storage 48 defines a condition for the discrepancy between the implementation result recorded in the past and that recorded anew. The implementation result recorded in the past is, for example, one recorded last time. For instance, that there is a variation of ±1° C. from the body temperature recorded last time is defined as a condition for body temperature. Also, a definite value may be defined as a condition. For instance, a condition for body temperature is set as being higher than 37° C.

FIG. 23 shows conditions stored in the storage 48. The conditions include an item space 160 and a variation space 162. Here, that the variation from the last time is "greater than 1° C." is set as a condition for "body temperature". That the variation from the last time is "greater than 50 cc" is set as a condition for "urine volume". That the variation from the last time is "greater than 10" is set as a condition for "pulse". Refer back to FIG. 2. The operation apparatus 62 receives a specification of changes in the conditions stored, from the nurse via the operation apparatus 62. Further, the storage 48 updates the condition by the specification received.

From among the implementation results recorded in the recording unit 60, the selector 46 selects implementation results that satisfy a condition stored in the storage 48. As described above, the conditions stored in the storage 48 are defined for the discrepancies between the implementation results recorded in the past and the newly recorded implementation results. Hence, if a newly recorded implementation result satisfies the condition, the selector 46 will select the newly recorded implementation result. According to the above-described example, if the discrepancies between the newly recorded implementation results and those recorded last time become larger, the selector 46 will select the newly recorded implementation results. That is, the selector 46 selects an implementation result that exhibits a somehow large variation. This is because the nurse directs more attention to a case exhibiting a larger variation. The viewing preparation unit 44 has the listing of the implementation result selected by the selector 46 displayed on a partial area, allotted for displaying the listing, of the screen of the display apparatus 64. Since the implementation result to be displayed is selected, as many implementation results to be verified by the nurse as possible are displayed on the screen even if the area allotted on the screen is limited.

Figure 24:
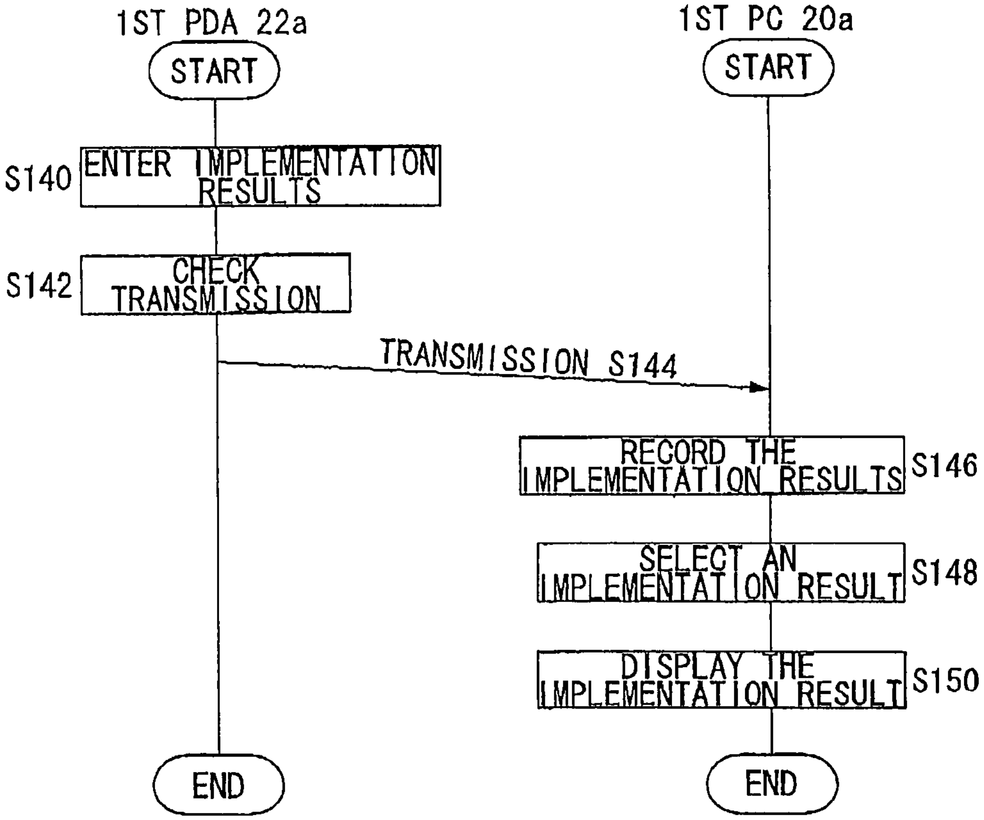
FIG. 24 is a sequence diagram showing a procedure for recording and displaying an implementation result in a nursing information management system of FIG. 1.
Figure 25:
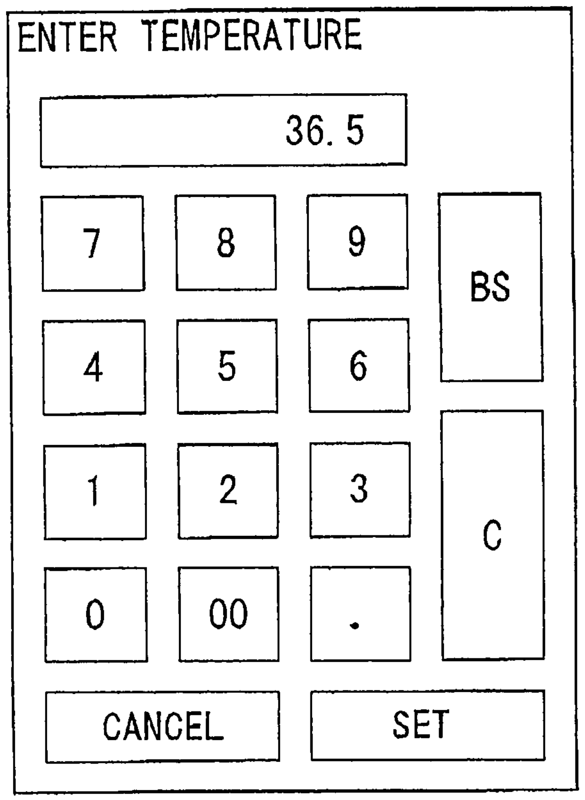
FIG. 25 illustrates an entry screen of an implementation result displayed by a PDA of FIG. 1.

FIG. 24 is a sequence diagram showing a procedure for recording and displaying an implementation result in the nursing information management system 10. A nurse enters an implementation result of a nursing action into the first PDA 22*a* (S140). FIG. 25 illustrates an entry screen of the implementation result displayed by a PDA 22. FIG. 24 corresponds to a case when a measured body temperature is entered. FIG. 25 illustrates buttons through which numerals are entered onto the center part of the screen. The nurse taps on buttons corresponding to the values to be inputted, and enters values representing an implementation result. As the entry of values for the implementation results has been completed, the nurse taps on a "set" button. If there are any other implementation results to be entered, the first PDA 22*a* will switch the screen to the one for the entry thereof. Note that the first PDA 22*a* requests the entry of implementation results corresponding to nursing items. The nursing items has been conveyed to the first PDA 22*a* by the orders which had already been issued.

Figure 26:
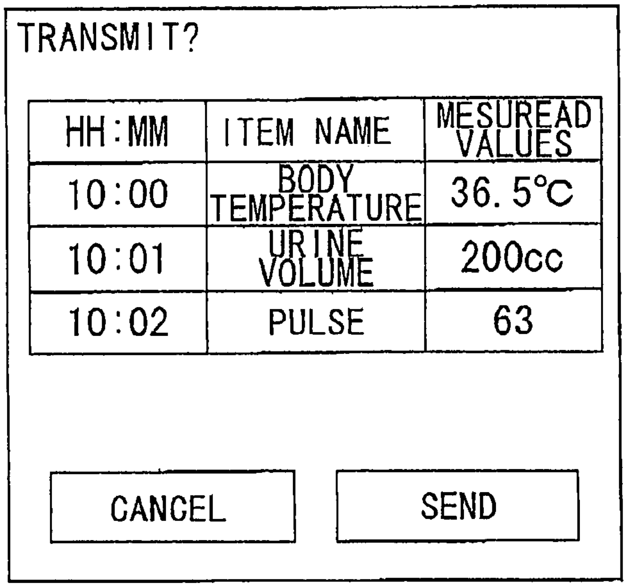
FIG. 26 illustrates a send screen for an implementation result displayed by a PDA of FIG. 1.

Refer back to FIG. 24. When the first PDA 22*a* receives an implementation result, it will prompt the nurse to check a transmission (S142). FIG. 26 illustrates a send screen for the implementation result displayed by the PDA 22. As contents to be sent to the screen, displayed are "body temperature", "urine volume" and "pulse", which are nursing items, and their respective measured values and measured time. If the contents of them are correct, the nurse will tap on a "send" button (S144). Refer back to FIG. 24. The first PDA 22*a* sends the implementation result to the first PC 20*a*. The first PC 20*a* records the implementation result (S146). Following this, the first PC 20*a* selects the implementation result (S148). Further, the first PC 20*a* displays the implementation result (S150).

Figure 27:
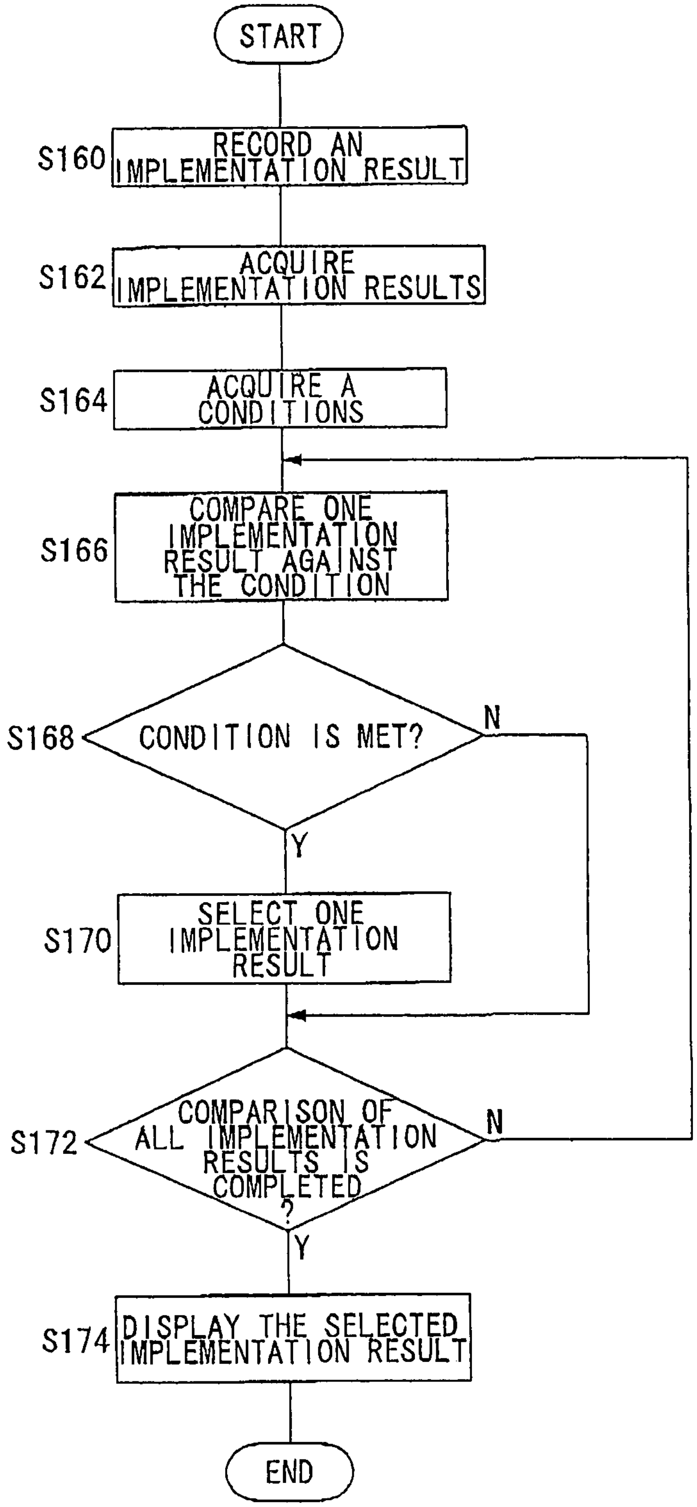
FIG. 27 is a flowchart showing a procedure for displaying an implementation result in a PC of FIG. 2.

FIG. 27 is a flowchart showing a procedure for displaying an implementation result in the PC 20. The recording unit 60 records the implementation result entered (S160). The selector 46 acquires implementation results from the recording unit 60 (S162) and acquires a condition from the storage 48 (S164). If there are a plurality of kinds of implementation results, the selector 46 will compare one of the implementation results against the condition (S166). If one of the implementation results satisfies the condition (Y of S168), the selector 46 will select the one of the implementation results (S170). If, on the other hand, one of the implementation results does not satisfy the condition (N of S168), no selection processing will be performed. If the comparing of all of the implementation results against the condition has not been completed (N of S172), the selector 46 will repeat the processing of Step 166.

Figure 28:
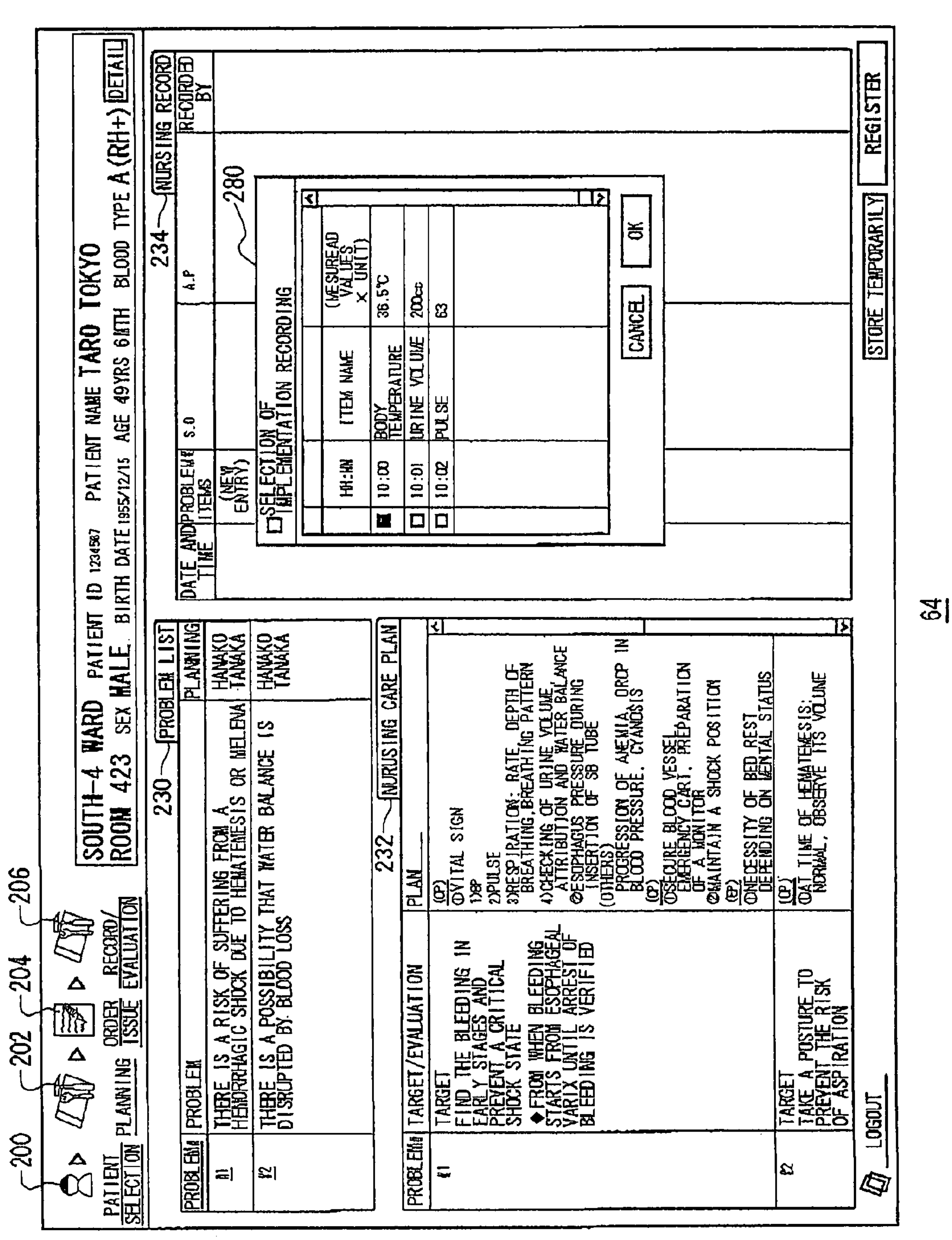
FIG. 28 illustrates an initial screen, at a stage of recording/evaluation, displayed on a display apparatus of FIG. 2.
Figure 29:
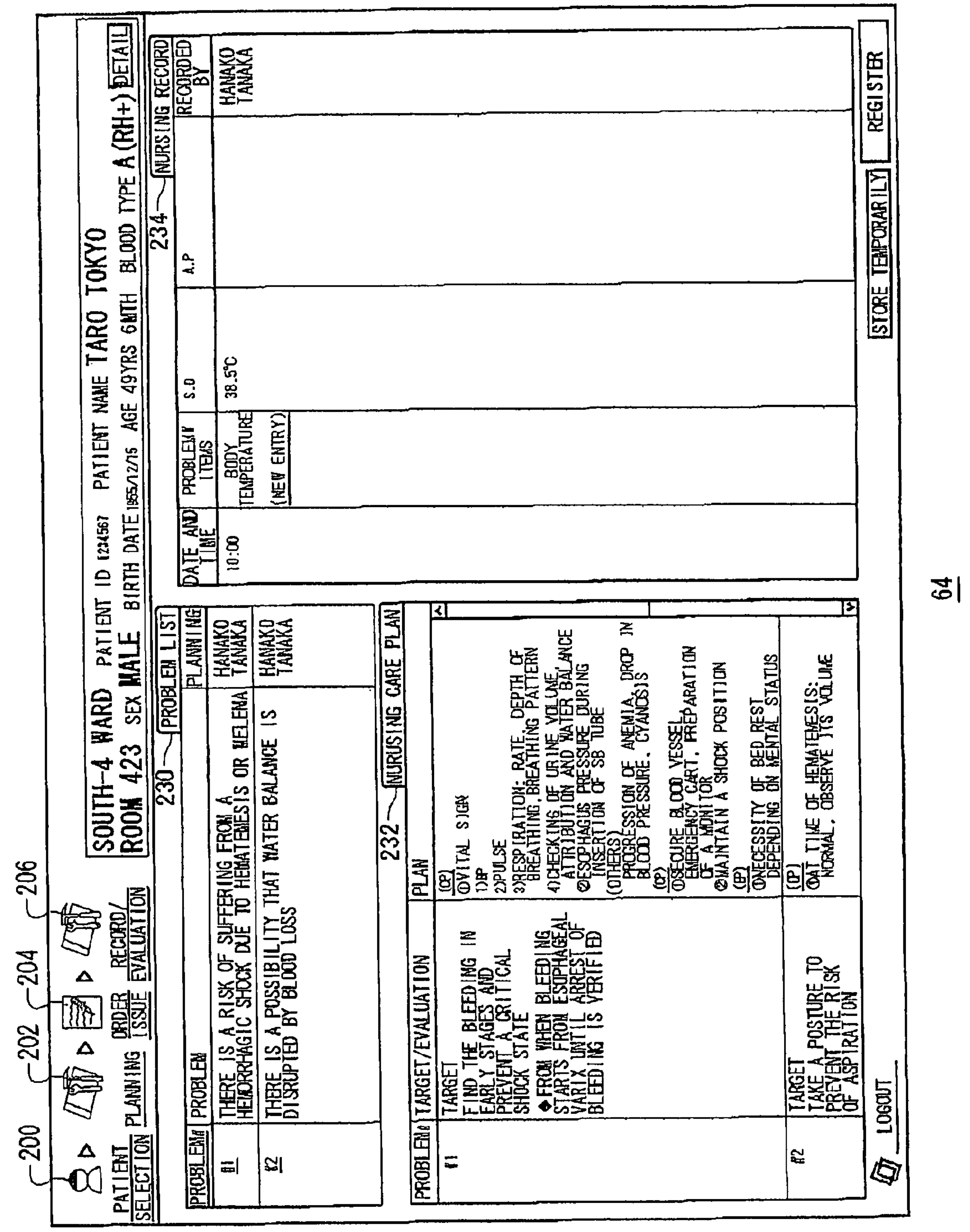
FIG. 29 illustrates a screen displayed after an implementation result displayed on a display apparatus of FIG. 2 has been entered.

If the comparing of all of the implementation results against the condition has been completed (Y of S172), the selector 46 will display the selected implementation result on the display apparatus 64 (S174). FIG. 28 illustrates an initial screen, at a stage of recording/evaluation, displayed on the display apparatus 64. A patient selection button 200 to a recording/evaluation button 206 are displayed but the recording/evaluation button 206 is selected here. At this stage, no implementation result is displayed in the nursing record space 234. Though an implementation result window 280 is displayed in FIG. 28, this may not be displayed at all. The content displayed on the implementation window 280 corresponds to the sent content of the implementation result shown in FIG. 26. FIG. 29 illustrates a screen displayed after the implementation result displayed on the display apparatus 64 has been entered. Since the body temperature was selected here by the selector 46, the body temperature is displayed in the nursing record space 234 as the implementation result.

A description will now be given of an operation of the nursing information management system 10 structured as above. The nurse conducts a nursing action to a patient after confirming the nursing items displayed on the PDA 22. The nurse enters an implementation result into the PDA 22. The PDA 22 sends the implementation result to the PC 20. The PC 20 stores the received implementation result in the recording unit 60. If the variation of the implementation result stored is larger than a predetermined condition, the selector 46 will select this implementation result. The display apparatus 64 displays the selected implementation result.

By employing the above structure, at the time of displaying the implementation results, an implementation result is selected based on a predetermined condition and then displayed, so that as many necessary implementation results as possible can be displayed even though a display area provided for the implementation results is narrow. Since conditions to select the implementation results are stored beforehand, a condition required to select an implementation result that the nurse should look out for can be set. Since a condition is set for discrepancy between the implementation result in the past and the current implementation result, a case where the discrepancy in the implementation results is large can be selected. Also, even if a plurality of kinds of implementation results are defined, conditions corresponding respectively thereto are set, so that a necessary implementation result can be selected. Since an implementation result with less importance is not displayed on the screen, the verification of necessary information for the nurse becomes easier. Even in the case when the implementation result does not turn out to be desirable, the chance of overlooking it is low so as to give warning to the nurse. Also, the change of a nursing care plan can be reviewed.

6. Feedback and Entry of Variance

Feedback and entry of variance correspond to Step 22, Step 24 and Step 26 of FIG. 24. The problems to be resolved here may be indicated as follows. It is desired that the contents of evaluation be reflected in the nursing care plan. It is desired that the nursing care plan be suited to a patient. It is desired that a patient be recovered as soon as possible. It is desired that the actual information and the decision be displayed so that they can be clarified. Also, a factor causing the discrepancy between an implementation result of a nursing item and a target in the nursing item the implementation of which has been specified be analyzed.

In order to achieve a feedback and the input of variance, the viewing preparation unit 44, the display apparatus 64, the input control unit 50, the operation apparatus 62, the control unit 42, the management unit 56, the recording unit 60, the plan preparation supporting unit 34 and the counting unit 58 in FIG. 2 are principally used here.

6.1. Entry of Evaluations

The input control unit 50 receives an evaluation of an implementation result of a nursing items, from a nurse via the operation apparatus 62. Here, as described above, the evaluation is defined in the SOAP format. The recording unit 60 records the received evaluation. In so doing, the management unit 56 assigns to the evaluation an identification number of a nursing problem item corresponding to the evaluation. As a result, the nursing problem items stored in the recording unit 60, the nursing items included in the nursing care plan, the implementation results and the evaluations are brought into correspondence with one another by predetermined identification numbers. Such correspondence is shown in FIG. 3, for example.

The viewing preparation unit 44 has the received evaluations displayed on the display apparatus 64. The viewing preparation unit 44 divides the screen into at least two areas and displays S and O in a first area on the screen, which has been divided into at least two areas, and displays A and P in a second area by associating them with S and O displayed in the first area. That is, among the constituents included in the SOAP format, S and O corresponding to the information on the status of a patient and A and P corresponding to evaluations other than the information on the status of a patient are distinguished from each other and displayed on the screen accordingly. Hence, the distinction therebetween is clarified. The combination of S and O and the combination of A and P are brought into correspondence with each other, so that the relationship therebetween can be clarified.

6.2. Feedback

When receiving an evaluation from the nurse via the operation apparatus 62, the input control unit 50 receives the entry of a new nursing care plan in cooperation with the evaluation. More specifically, when entering P, the input control unit 50 receives a new nursing care plan that reflects the content of A. That is, the content of a nursing care plan which has not been entered is entered. While the entered nursing care plan is being managed by the management unit 56, it is recorded in the recording unit 60. When receiving the evaluation from the nurse, the input control unit 50 receives a specification about the completion or continuation of the nursing care plan. If a specification of the completion of the nursing care plan was received, the management unit 56 performs processing such as closing the information corresponding thereto in the nursing information recorded in the recording unit 60, and performs an end processing on the corresponding information.

If, on the other hand, a specification of the continuation of the nursing care plan was received, the information corresponding thereto in the nursing information recorded in the recording unit 60 continues to be effective. If the input control unit 50 receives a specification about the continuation of a nursing care plan, it will receive also a specification as to whether the nursing care plan is to be changed or not. If the nursing care plan is not to be changed, the nursing information recorded in the recording unit 60 will continue to be effective. If on the other hand, the nursing care plan is to be changed, the input control unit 50 will also receive contents of changes in the nursing care plan. The management unit 56 will reflect the changes in the nursing information recorded in the recording unit 60. Note that the plan preparation supporting unit 34 may reflect the received specification in the already prepared nursing care plan. In this manner, the contents of the evaluation are reflected in the nursing care plan.

6.3. Entry of Variance

If there is any discrepancy between the implementation results of nursing items and the targets in the nursing items specified to be implemented, the input control unit 50 receives also the input of variance factors when it receives evaluations from the nurse via the operation apparatus 62. A variance factor is said to represent information on a factor of discrepancy between the nursing care plan including a nursing target for a patient and the implementation result. The case where there is a discrepancy between an implementation result and a target in the nursing items specified to be implemented corresponds to a case where a recovery condition of a patient attended and a recovery condition of the patient which was planned beforehand differ and are apart from each other. That is, the discrepancy includes a case where the recovery is earlier than planned and a case where the recovery is slower than planned. In the case when there is any discrepancy, the management unit 56 presents a plurality of candidates for the variance factor to the nurse via the display apparatus 64. When the nurse selects any of the plurality of candidates via the operation apparatus 62, the management unit 56 receives the variance factor.

Figure 30:
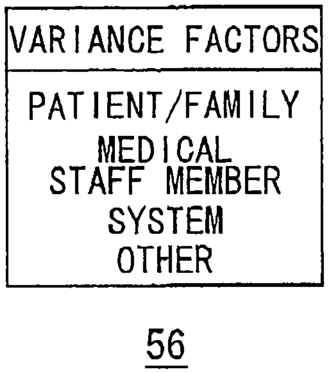
FIG. 30 is a data structure showing the candidates of a variance factor stored in a management unit of FIG. 2.

FIG. 30 is a data structure showing the candidates for the variance factor stored in the management unit 56. Here, “patient/family”, “medical staff member”, “system” and “other” are defined as variance factors. The factor “patient/family” indicates that the variance is attributable to a patient and/or his/her family members. More specifically, a case where the curing is delayed because of diabetes, the patient’s family members lack the understanding and so forth corresponds to this factor. In order to cope with this, the reviewing or reexamination of adaptation and therapeutic regimens will be effective. The factor “medical staff member” indicates that the variance is attributable to medical staff members. More specifically, a case where an incorrect drug is given, a patient is misidentified, an incorrect specification/instruction is given and so forth corresponds to this factor. In order to cope with this, educating the medical staff members and giving an on-the-job training (OJT) to them will be effective. The factor “system” indicates that the variance is attributable to systems. More specifically, a case where equipment malfunctions and the reservation is full corresponds to this factor. In order to cope with this, the efficient utilization of equipment and facilities will be effective. The factor “other” is attributable to factors other than the aforementioned. For example, social factors, the inability of securing a hospital to be transferred and the absence or inadequacy of domestic caring. In order to cope with this, the coordination of disease examination, the reviewing of a regulation for the number of hospital beds and home visiting nursing will be effective.

Furthermore, the management unit 56 presents to the nurse an open-ended entry space for the entry of an evaluation. This open-ended entry space corresponds to a space provided for giving a comment to the evaluation. The management unit 56 associates the comment in the open-ended entry space entered by the nurse with the selected variance factor. The thus associated comment in the open-ended entry space is stored in the recording unit 60. Also, as shown in FIG. 3, the recording unit 60 records the implementation results and the variance factors by associating them with the nursing care plans.

The counting unit 58 counts the number of variance factors stored in the recording unit 60, for each of a plurality of candidates regarding variance factors. That is, since “patient/family”, “medical staff member”, “system” and “other” are defined as a plurality of candidates, the counting unit 58 classifies the received variance factors into a plurality of candidates, respectively, and counts the number of variance factors for each of the plurality of candidates. In so doing, the counting unit 58 performs the counting by directing attention to the relationship between the implementation results and the targets. That is, when the number of variance factors received for one candidate, for example, “patient/family” is counted, the received variance factors are separated into positive variance factors and negative variance factors so as to conduct the counting. The positive variance factor is a variance factor for a case where the recovery is earlier than a target, and this corresponds to a variance factor which is to serve as a target for improvement. On the other hand, the negative variance factor is a variance factor for a case where the recovery is slower than the target, and this corresponds to a variance factor which needs to be improved.

FIG. 31 illustrates a counting result recorded in the counting unit 58. The counting result includes a variance space 170, a factor space 172 and a number-of-times space 174. In the variance space 170, variance factors are separated into positive factors and negative factors. Here, “+” corresponds to the positive factors and “−” the negative variance. The above-described plurality of candidates are respectively defined in the factor space 172. The number-of-times space 174 indicates the number of variance factors for each of the plurality of candidates. In the case of FIG. 31, there are many of “medical staff member” as the positive variance whereas there are many of “system” as the negative variance. From this counting result, it is concluded that “medical staff member” needs to be improved in order to make the recovery earlier than the target and “system” needs to be improved in order to improve the case where the recovery is slower than the target.

6.4. Operation

Figure 32:
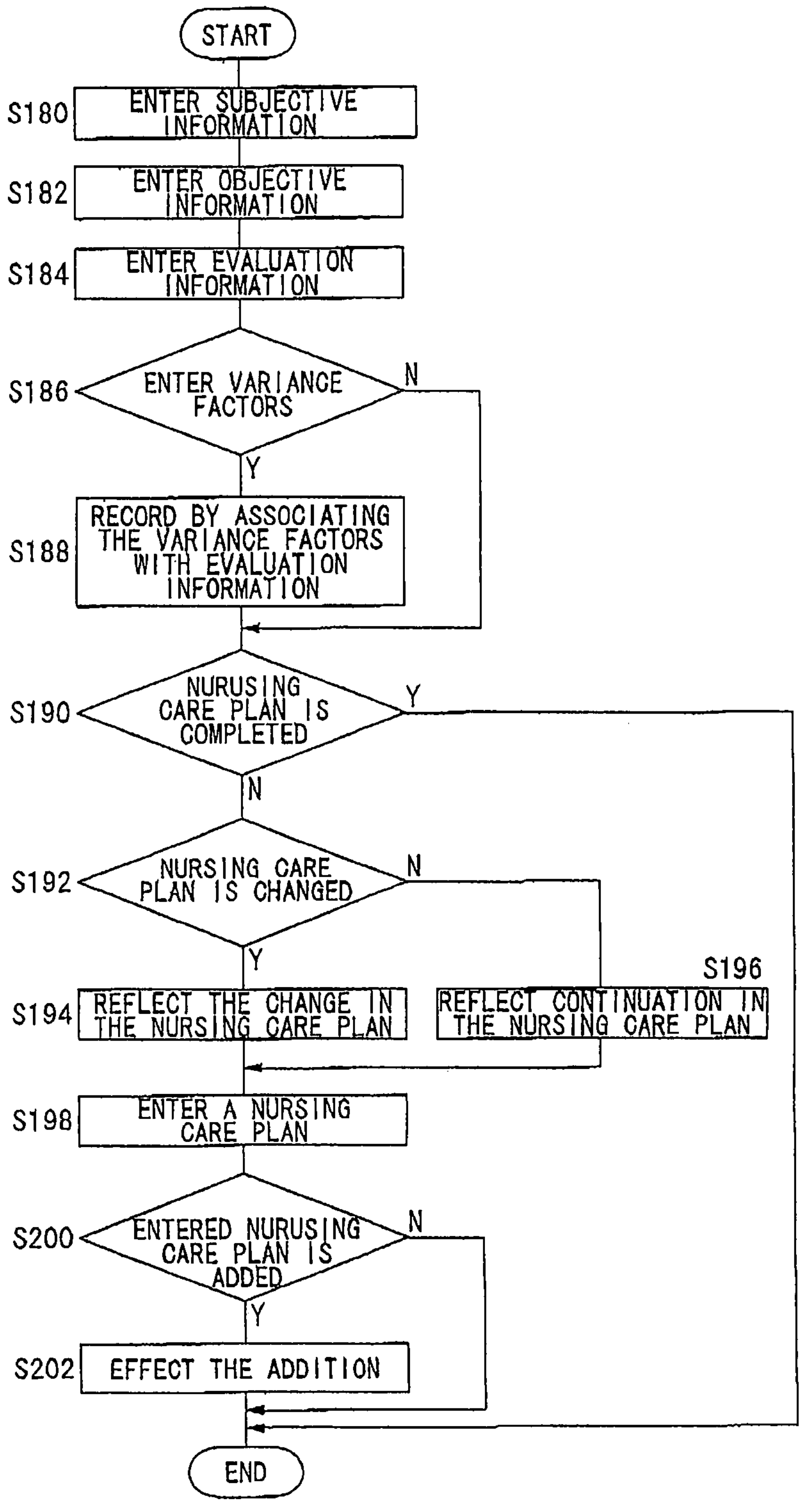
FIG. 32 is a flowchart showing a procedure for feedback processing in a PC of FIG. 2.
Figure 33:
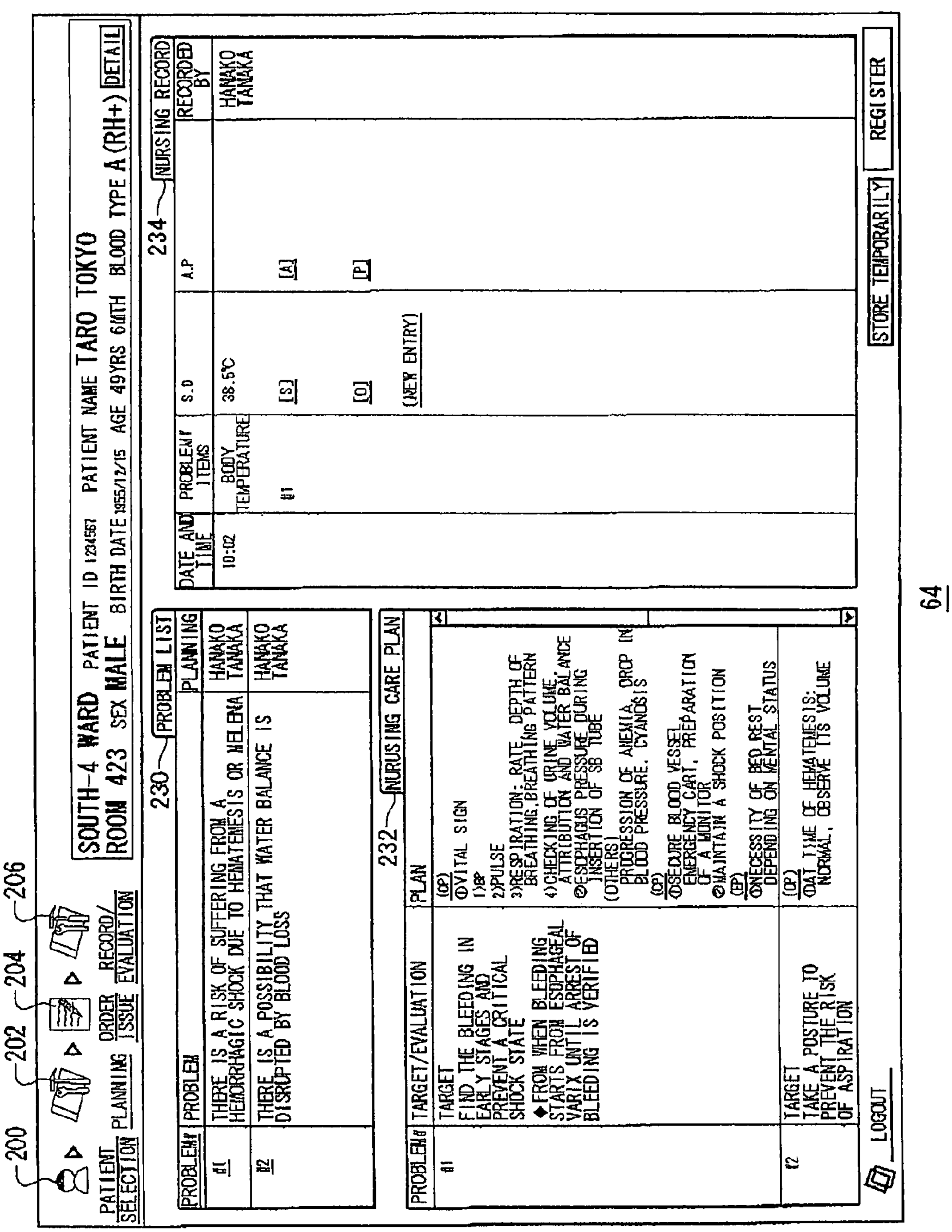
FIG. 33 illustrates an initial screen obtained when an evaluation is entered and displayed on a display apparatus of FIG. 2.
Figure 34:
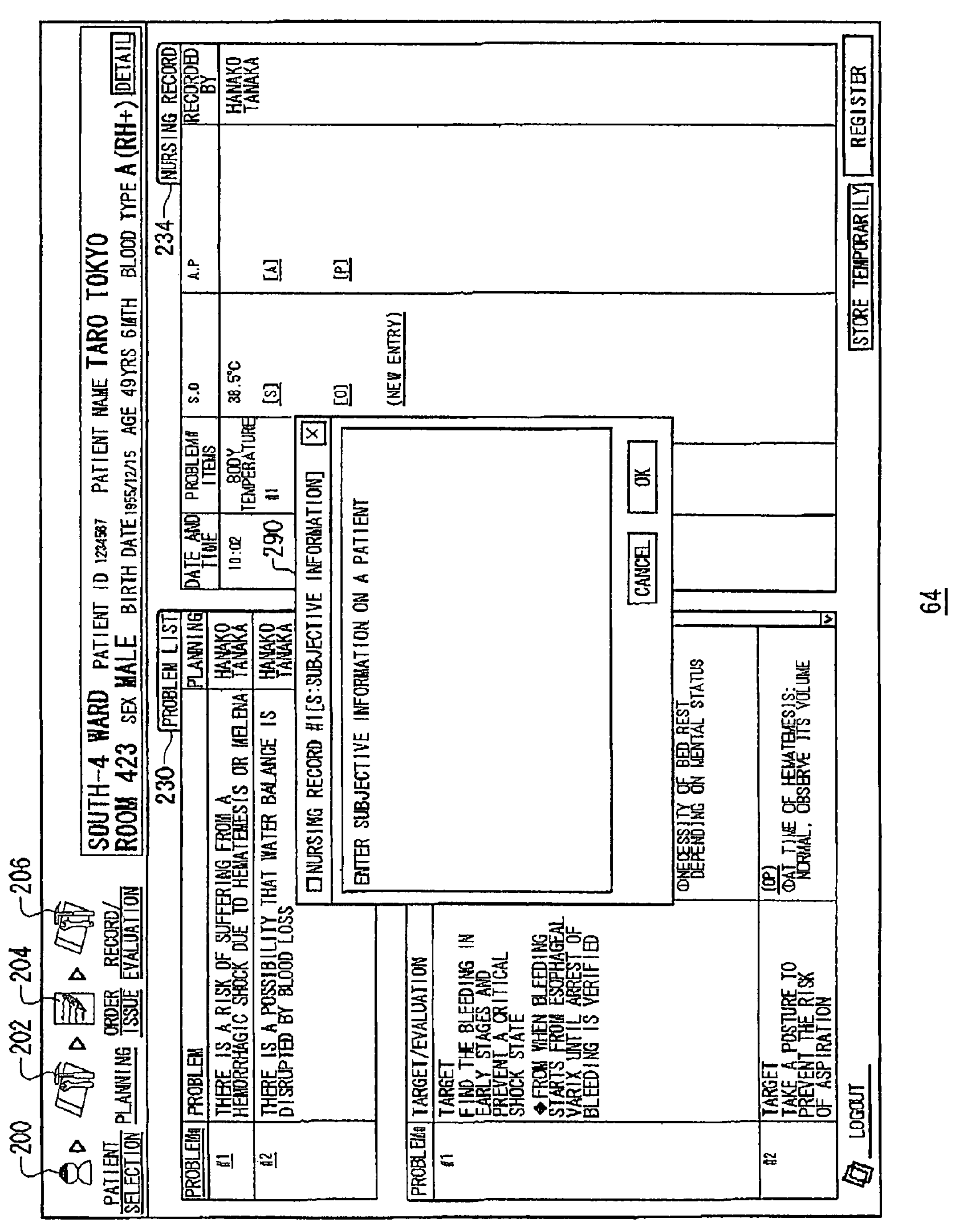
FIG. 34 illustrates an input screen of subjective information displayed on a display apparatus of FIG. 2.

FIG. 32 is a flowchart showing a procedure for feedback processing in the PC 20. The input control unit 50 receives the entry of subjective information (S) via the operation apparatus 62 (S180). The received subjective information is recorded in the recording unit 60. FIG. 33 illustrates an initial screen obtained when an evaluation is entered and displayed on the display apparatus 64. FIG. 33 illustrates a screen at a stage before subjective information is entered. In FIG. 33, the recording/evaluation button 206 is selected, and areas to display “S”, “O”, “A” and “P” are provided in the nursing record space 234. FIG. 34 illustrates an entry screen of the subjective information displayed on the display apparatus 64. A subjective information entry window 290 is displayed in FIG. 34. The nurse enters subjective information using the operation apparatus 62.

Figure 35:
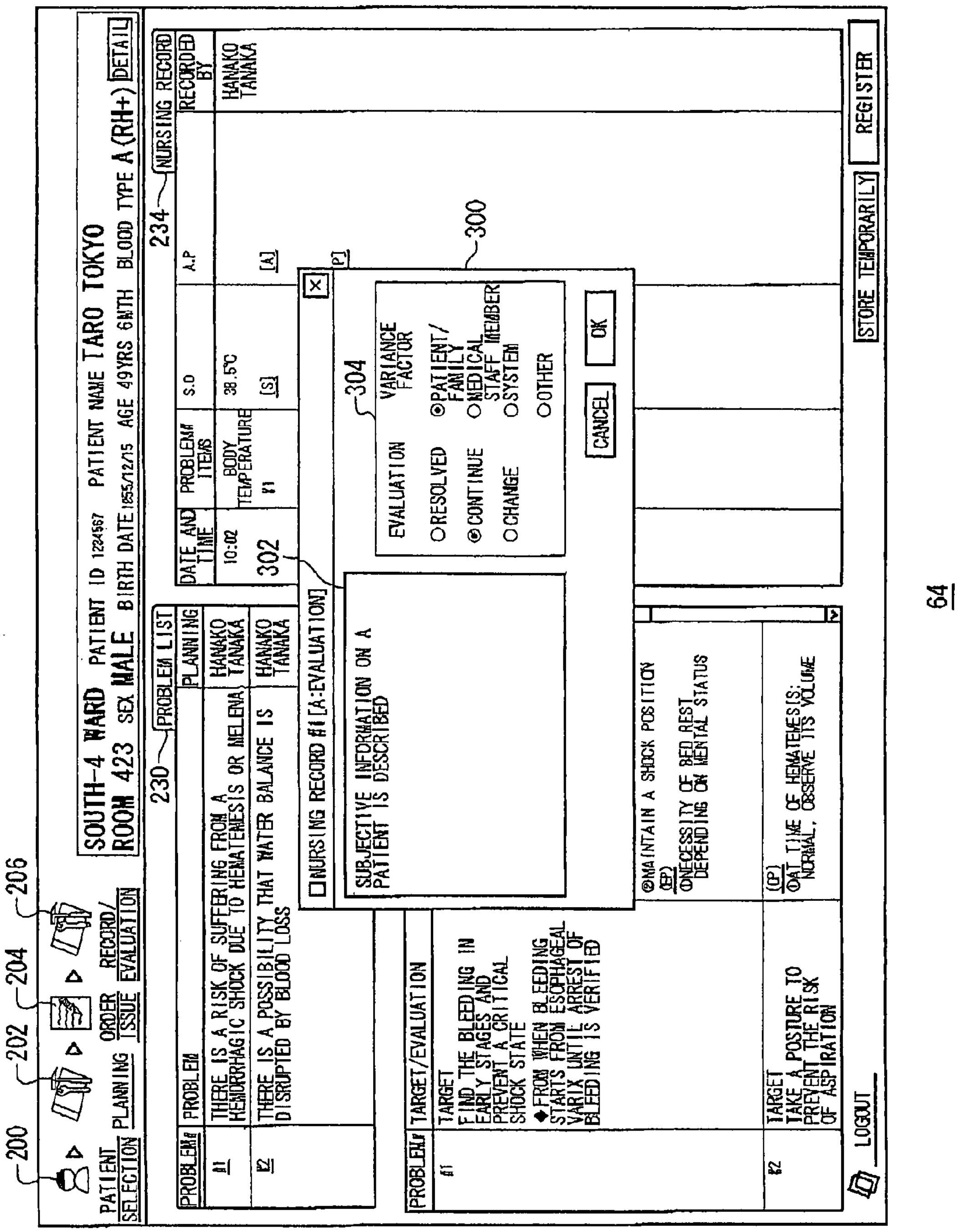
FIG. 35 illustrates an entry screen of evaluation information displayed on a display apparatus of FIG. 2.

Refer back to FIG. 32. The input control unit 50 receives the entry of objective information (O) via the operation apparatus 62 (S182) The received objective information is recorded in the recording unit 60. The same screen as that of FIG. 34 is displayed on the display apparatus 64. The input control unit 50 receives the entry of evaluation information (A) via the operation apparatus 62 (S184). The received evaluation information is recorded in the recording unit 60. FIG. 35 illustrates an entry screen of evaluation information displayed on the display apparatus 64. An evaluation information entry window 300 is displayed on the screen. The evaluation entry window 300 includes an open-ended entry space 302 and an evaluation/variance factor space 304. Using the operation apparatus 62, the nurse enters evaluation information into the open-ended entry space 302. Refer back to FIG. 32. If the input control unit 50 receives the entry of a variance factor (Y of S186), the recording unit 60 will record the received variance factor by associating it with the evaluation information (S188).

If, on the other hand, the input control unit 50 does not receive the entry of a variance factor (N of S186), proceed to the next step. In the evaluation/variance factor space 304 of FIG. 35, the entry of a variance factor is made by selecting any of a plurality of candidates including “patient/family” and so forth. Refer back to FIG. 32. If the input control unit 50 receives a specification to terminate a nursing care plan (P) (Y of S190), the processing will be terminated. If, on the other hand, the input control unit 50 does not receive a specification to terminate a nursing care plan (N of S190) and it receives a specification to change a nursing care plan (Y of S192), the management unit 56 or the plan preparation supporting unit 34 will reflect the change in the nursing care plan (S194). Also, the recording unit 60 records the changed nursing care plan. If the input control unit 50 does not receive a specification to change a nursing care plan (N of S192), the management unit 56 or the plan preparation supporting unit 34 will reflect the continuation thereof in the nursing record (S196).

Figure 36:
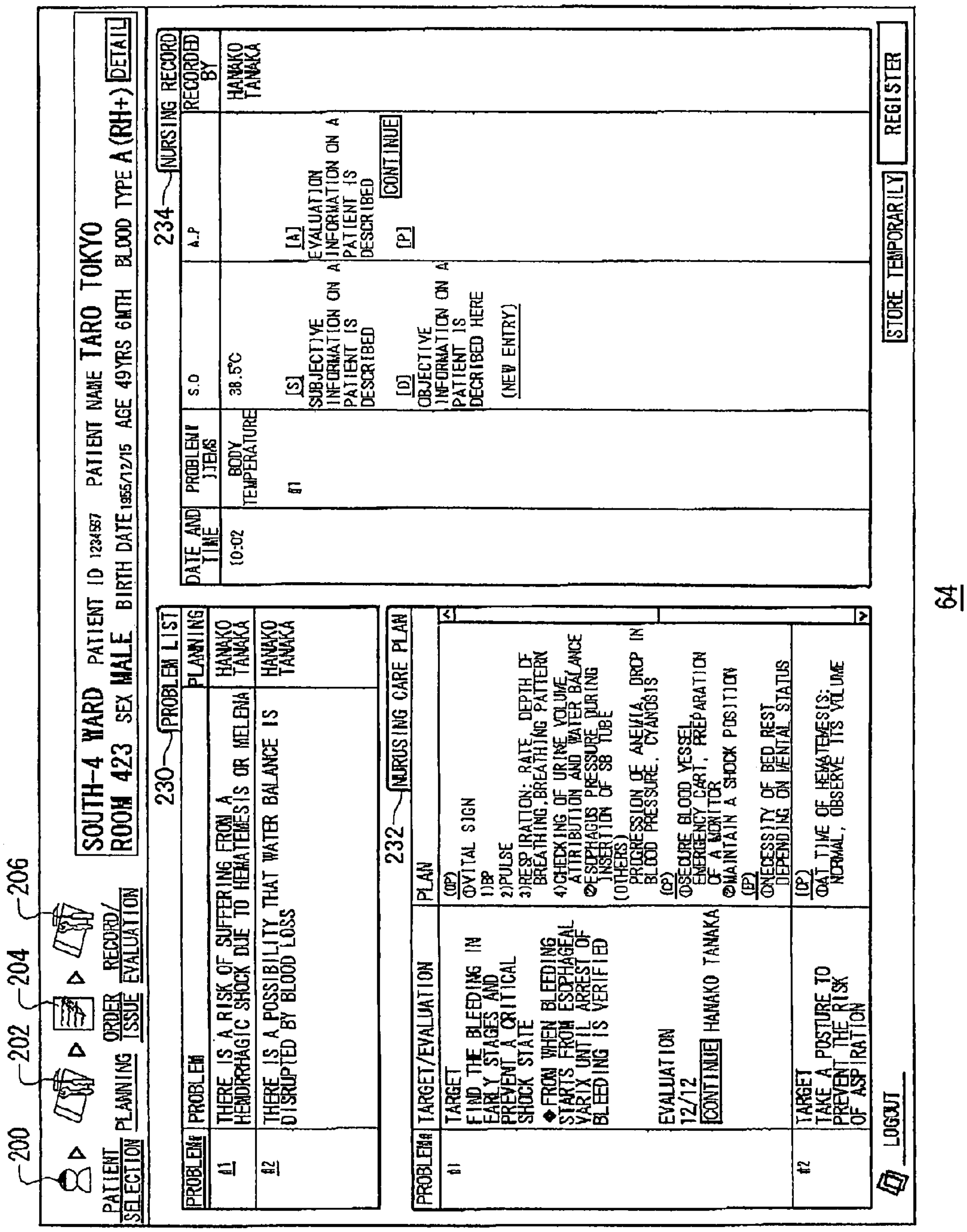
FIG. 36 illustrates a screen obtained after the evaluation information displayed on a display apparatus of FIG. 2 has been entered.

Such termination, continuation and change of a nursing care plan as described above are done by selecting any of "resolved", "continue" and "change" in the evaluation/variance factor space 304 of FIG. 35. FIG. 36 illustrates a screen obtained after the evaluation information displayed on the display apparatus 64 has been entered. FIG. 36 corresponds to a case where the continuation of a nursing care plan is specified. In FIG. 35, when the continuation thereof is selected, "continue" is displayed under "A" of the nursing record space 234. "Continue" is also displayed in "evaluation" of the nursing care plan space 232. Refer back to FIG. 32. The input control unit 50 receives the entry of a nursing care plan via the operation apparatus 62 (S198). Also, the received nursing care plan is recorded in the recording unit 60. Further, if the input control unit 50 receives a specification to add the inputted nursing care plan via the operation apparatus 62 (Y of S200), the management unit 56 or the plan preparation supporting unit 34 will implement the addition (S202).

Figure 37:
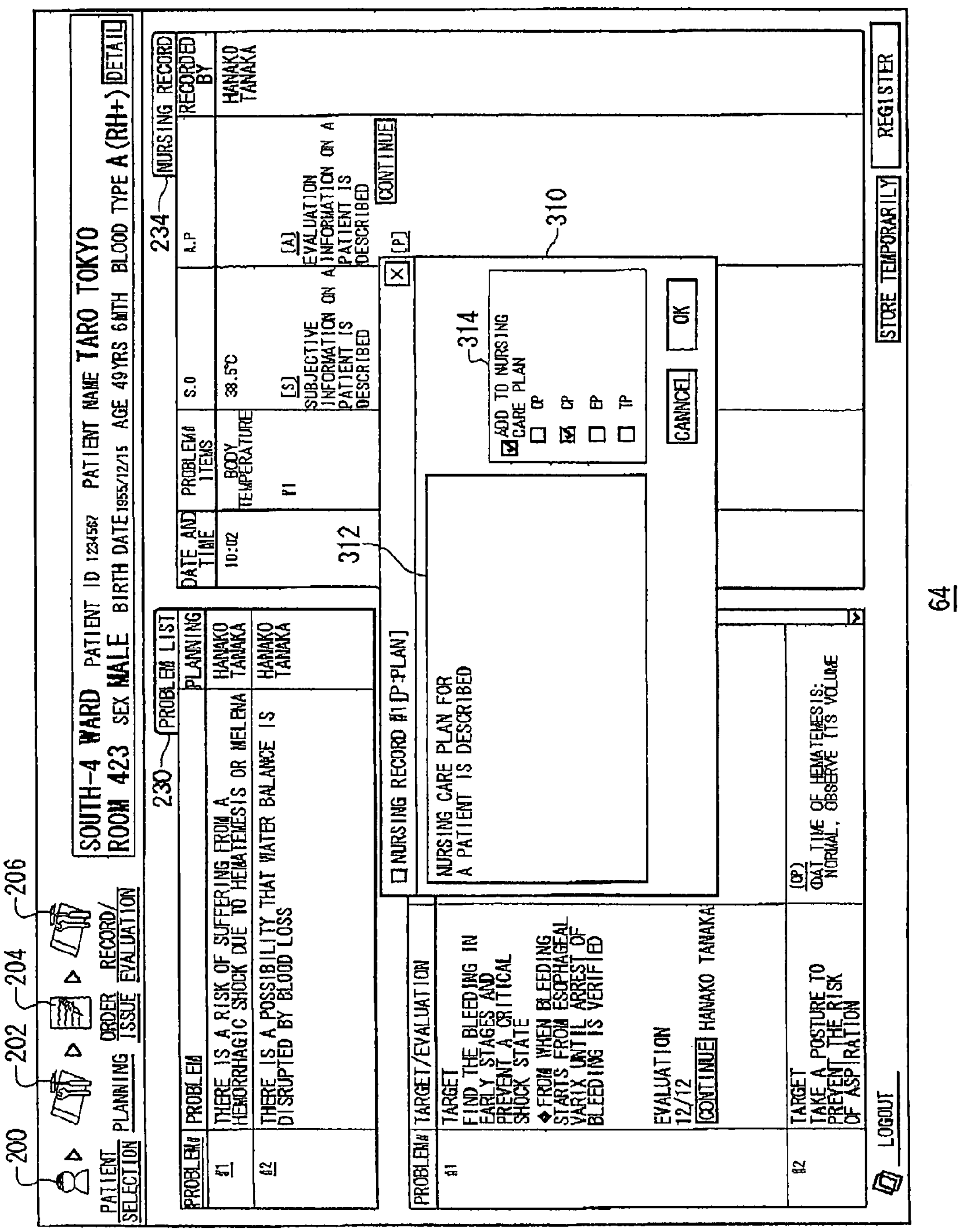
FIG. 37 illustrates an entry screen of a nursing care plan displayed on a display apparatus of FIG. 2.

That is, the added nursing care plan is reflected in the nursing care plan space 232 displayed on the display apparatus 64. If, on the other hand, the input control unit 50 does not receive a specification to add the inputted nursing care plan via the operation apparatus 62 (N of S200), the processing will be terminated. FIG. 37 illustrates an entry screen of the nursing care plan displayed on the display apparatus 64. A nursing care plan window 310 is displayed on the screen. The nursing care plan window 310 includes an open-ended entry space 312 and a selection space 314. Using the operation apparatus 62, the nurse enters a nursing care plan into the open-ended entry space 312. Further, if the entered content is added to the nursing care plan space 232, a predetermined item contained in the selection space 314 is selected. FIG. 38 illustrates a screen obtained after the nursing care plan displayed on the display apparatus 64 has been entered. The content described in the open-ended entry space 312 of FIG. 37 is reflected in "P" in the nursing record space 234. Also, "plan added" is displayed in the nursing care plan space 232.

Figure 39:
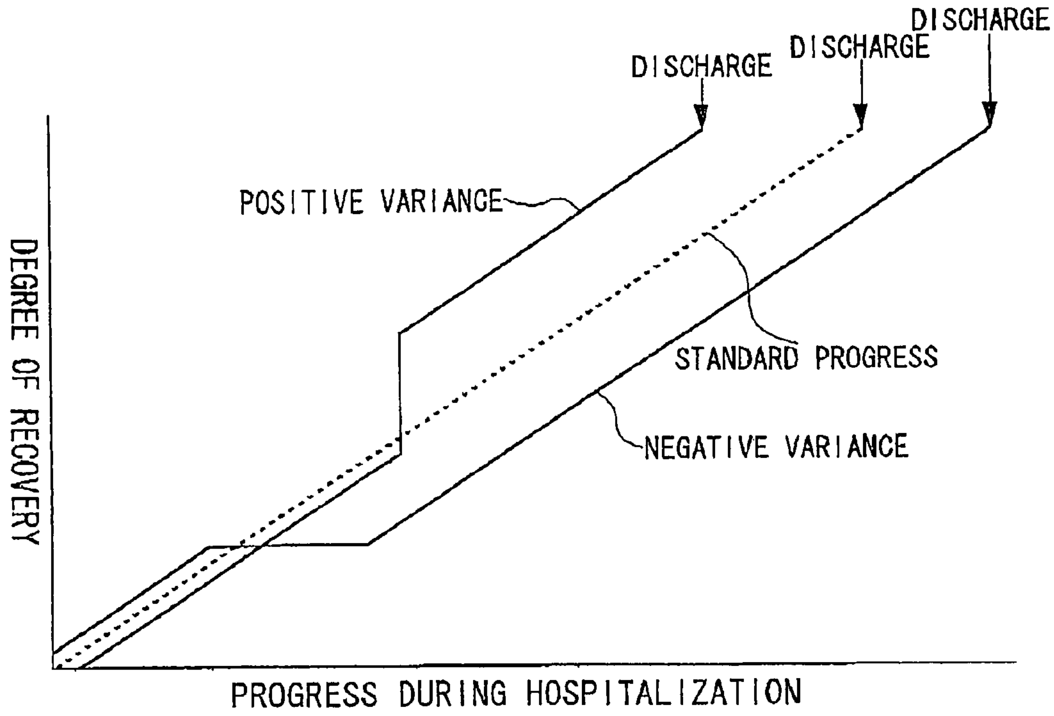
FIG. 39 is a graph to explain an effect of a variance analysis concerning an embodiment.

FIG. 39 is a graph to explain an effect of a variance analysis concerning the present embodiment. The horizontal axis in the graph indicates a progress during hospitalization, which means here the number of hospital stays. The vertical axis of the graph indicates the degree of recovery of a patient, and this means that the higher the position in the graph, higher the degree of recovery is. A "standard progress" indicated by a dotted line in the graph is a progression serving as a target when variance factors are entered. For clarity of the graph, the standard progress is indicated by a straight line here. The timing of discharge is indicated by an arrow mark. A positive variance corresponds to a case where the discharge timing is earlier than the standard progress. On the other hand, a negative variance corresponds to a case where the discharge timing is slower than the standard progress.

For a patient, a shorter duration of hospitalization is desired. The shorter the duration of hospitalization, smaller the expenditure in the hospital. As a result, the improvement of nursing contents by which to shorten the duration of hospitalization is desired. If the present progress indicates a negative variance, the variance factors at the present time will be analyzed and the nursing contents will be improved so that the progress is brought close to a positive variance. Such analysis of variance factors is performed by a medical institution or an external institution, based on the counting results in the counting unit 58. Finally, the duration of hospitalization can be reduced by bringing the present standard progress closer to a positive variance.

An operation of the PC 20 structured as above will be now be described. The nurse enters an evaluation of the nursing result in accordance with the SOAP format. Using the operation apparatus 62, the nurse also enters variance factors. Using the operation apparatus 62, the nurse further enters a new nursing care plan in connection with the evaluation. These pieces of information are recorded in the recording unit 60 by bringing them into correspondence with one another. Also, the counting unit 58 performs the counting for the variance factors.

By employing the structure described as above, a nursing care plan can be added in connection with the evaluation, so that the contents of the evaluation can be reflected in the nursing care plan. If a nursing care plan which is more suitable than the already prepared nursing care plan is added, the recovery of a patient will be facilitated. Since the added nursing care plan is also displayed in an area where the nursing care plan is to be displayed, the correspondence between the added contents and the contents already displayed can be clarified. Since the completion or continuation of a nursing care plan can be entered in connection with the evaluation thereof, the contents of the evaluation can be reflected in the nursing care plan while the contents of the evaluation is being verified. When the continuation thereof is selected, this is displayed accordingly, so that the contents of what has been selected is clarified. Since a change in the nursing care plan can be entered in connection with the evaluation, the nursing care plan can be modified to a more appropriate plan. Reflecting the contents of evaluation in the nursing care plan makes the nursing care plan more suitable. The recovery of a patient can be improved. The length of hospital stay for a patient can be shortened. When the evaluation is displayed, a combination of S and O and a combination of A and P are displayed separately, so that their differences can be clarified. Since the combination of S and O and the combination of A and P are displayed by associating one combination with the other, the correspondence therebetween can be clarified.

If there is any discrepancy between the implementation results of nursing items and the targets in the nursing items specifying the implementations, its contributing factors are entered, so that the contributing factors can be analyzed. By analyzing the contributing factors, the contents of a nursing care can be improved. Since the contents of a nursing care is improved, the duration of patient hospitalization can be shortened. Also, the hospital cost can be reduced. When the contributing factors are entered, candidates for the factors are also presented beforehand and a nurse is requested to select proper factors from among those candidates. Thus the entry of contributing factors can be simplified. Since the candidates for the factor are defined beforehand, the analysis of the contributing factors is facilitated. When the entered factors are gathered and counted, the counting is conducted by directing attention to a relationship with the implementation results, so that the level or characterization of the contributing factors becomes clear and a feedback of the contributing factors can be properly implemented. The entered factors are counted by dividing them into the categories of a positive variance and a negative variance, the improving measures for the nursing care best suited to a situation can be specified.

7. Entry of Variances

As described above, in the above embodiments, the variance factors, namely information on discrepancy (hereinafter referred to as "discrepancy information") are associated with the entire nursing care or entire examination for patients. Here, the entire nursing care or entire examination for patients corresponds to one hospitalization unit, for example. In a nursing care supporting system, the discrepancy information in units of patient hospitalization is also verified and, at the same time, large information having the size of one hospitalization unit is also acquired. Accordingly, when statistical data of discrepancy information is to be utilized for a hospital operation, it can only be verified in terms of one hospitalization unit. In order to resolve such a problem, a description will be given here of the entry of variance factors. That is, a purpose of the present embodiment is to acquire, in finer levels, the contributing factors resulting from the discrepancies between plans in the medical actions and the implementation contents thereof, analyze them and improve and ensure appropriate medical action. Note that relevant parts other than the entry of variance factors are the same as those in the above-described embodiments and the corresponding parts in the above chapters 6.3 and 6.4 may be replaced by the following description.

In the above embodiment, the variance factors are entered in such a manner that the variance factors are associated with nursing care plans which have been set. Here, the variance factors are also associated with the nursing problems, prepared at the time of the preparation of nursing care plans, in addition to the nursing care plans. The structure of the PC 20 here is the same as that of FIG. 2. The first database 32 and the second database 36 record standard problems of a patient per disease and their standard plans corresponding to the standard problems. Hereinbelow, a standard problem and a standard plan will be generically and collectively referred to as "standard plan". As shown in FIG. 8 and FIG. 9, the standard plan corresponds to a nursing problem and a nursing care plan which are defined beforehand where targets, problems and plans are brought into correspondence with one another. Note that in the first database 32 the standard plan also includes information on departments, as shown in FIG. 8.

The problem preparation supporting unit 30 and the plan preparation supporting unit 34 set nursing problems concerning patients' diseases and nursing care plans corresponding to these nursing problems. More specifically, as described above, the problem preparation supporting unit 30 and the plan preparation supporting unit 34 select nursing problems for patients to be given a nursing care and nursing care plans from the standard plans recorded in the first database 32 and the second database 36. In so doing, the problem supporting unit 30 also sets information on departments. Note that the nursing problems may not be set by the problem preparation supporting unit 30 and the nursing care plans only may be set by the plan preparation supporting unit 34. The management unit 56 and the recording unit 60 records implementation contents of nursing actions conducted along with the nursing care plans set, namely evaluations of the implementation results of the above-described nursing items.

The management unit 56 inputs, via the input control unit 50, information on contributing factors of discrepancy between the nursing care plans set and the implementation contents thereof. Here, the information on the discrepancy factors corresponds to the above-described variance factors. In so doing, the management unit 56 inputs variance factors for each of the problems of a patient's disease. When inputting the variance factors, the management unit 56 also inputs information on departments. While presenting, via the display apparatus 64, problems concerning a patient's disease to be associated with variance factors, the management unit 56 prompts the nurse to make an entry. FIG. 40 illustrates a data structure for an entry setting of variance factors stored in the management unit 56, and the management unit 56 prompts the nurse to make an entry based on this data structure, The unit in which the variance factors are entered (hereinafter referred to as "variance entry unit", "in units of variance entry" or "per variance entry") is set by the nurse. As shown FIG. 40, if per hospitalization is set in units of variance entry, it will become unable to enter the variance factors in units of department, in units of disease and in units of problem and therefore the management unit 56 will receive the entry of variance factors in units of hospitalization. If per department is selected in units of variance entry, it will become unable to enter the variance factors in units of disease and in units of problem and therefore the management unit 56 will receive the variance factors in units of department. If per disease is selected in units of variance entry, it will become unable to enter the variance factors in units of problem and therefore the management unit 56 will receive the variance factors in units of department and in units of disease. If per problem is selected in units of variance entry, the management unit 56 will receive the variance factors in units of department, in units of disease and in units of problem. Refer back to FIG. 2.

At the time of entry of variance factors, the management unit 56 uses a list similar to that at the preparation of nursing problems by the problem preparation supporting unit 30, for example, the list shown in FIG. 12. Note that, similar to FIG. 12, a standard plan is used for the contents of a list. Accordingly, in order to be related to the same nursing problem, the nursing plans and the variance factors are brought into correspondence to each other. In addition to what has been described above, the management unit 56 has the following functions for the entry of variance factors.

(1) A plurality variance factors can be registered for each patient hospitalization.

(2) An entry screen of variance factors has a registration function only and there is no reference function for the registered contents.

(3) The management unit 56 receives the selection of positive/negative of variance factors (positive (+), negative (−) or none).

(4) When "+" or "−" is selected as positive/negative of variance factors, the entry of variance days is received.

(5) The selection of variance factors is received. As described above, the variance factors are stored in the management unit 56.

(6) The selection of detailed variance factors is received. The detailed variance factors are set in the management unit 56.

(7) Pressing a displayed "register" button completes the registration of an item set on the screen.

The recording unit 60 records problems on a patient's disease, namely the unit of variance entry, and information on entered variance factors by associating them with each other. The recording unit 60 records these pieces of information in a manner shown in FIG. 3. The counting unit 58 displays the data accumulated in the recording unit 60 for each variance entry. Also, the counting unit 58 performs statistical processing on the data accumulated in the recording unit 60. The nurse gathers and counts the displayed data and reexamines the standard plan.

Figure 41:
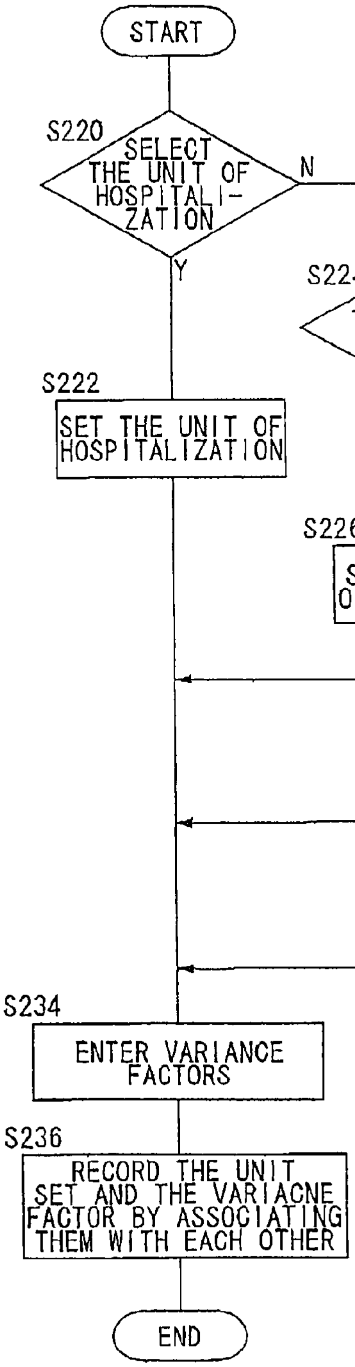
FIG. 41 is a flowchart showing a procedure for entering variance factors in a PC of FIG. 2.

FIG. 41 is a flowchart showing a procedure for entering variance factors in the PC 20.

If per hospitalization or the unit of hospitalization (i.e., entry in units of hospitalization) is selected (Y of S220), the management unit 56 will set the unit of hospitalization as the unit of variance entry (S222). If the unit of hospitalization is not selected (N of S220) and the unit of department is selected (Y of S224), the management unit 56 will set the unit of department as the unit of variance entry (S226). If the unit of department is not selected (N of S224) and the unit of disease is selected (Y of S228), the management unit 56 will set the unit of disease as the unit of variance entry (S230). If the unit of disease is not selected (N of S228), the management unit 56 will select the unit of problem as the unit of variance entry (S232).

Figure 42:
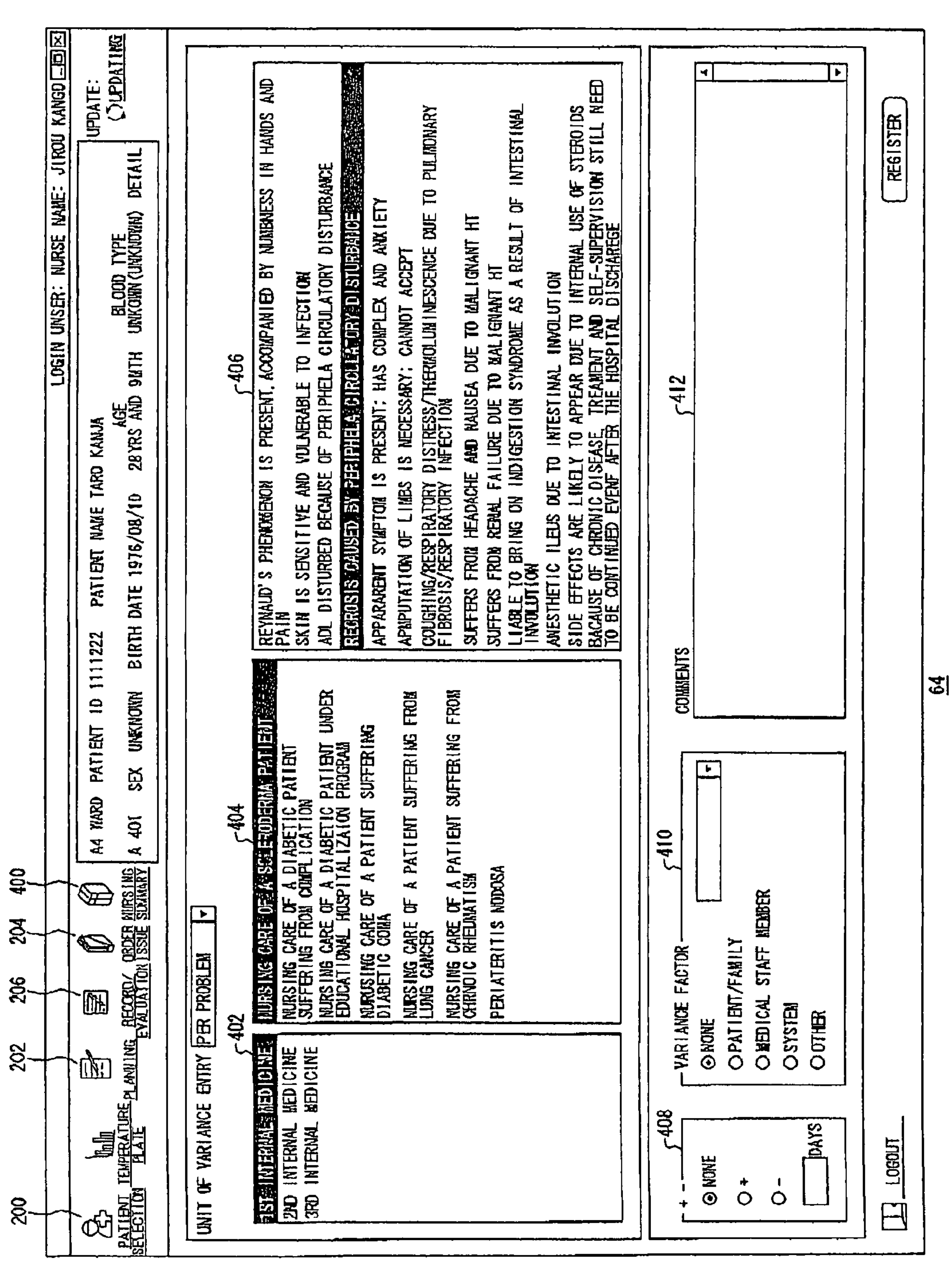
FIG. 42 illustrates an entry screen of variance factors displayed on a display apparatus of FIG. 2.

FIG. 42 illustrates an entry screen of variance factors displayed on the display apparatus 64. On the top of screen, there are provided a department space 402, a disease space 404 and a nursing problem space 406. As shown in FIG. 42, if "per problem" (the unit of problem) is selected as the unit of variance entry, the department space 402, the disease space 404 and the nursing problem space 406 will become selectable. If "per disease" (the unit of disease) is selected as the unit of variance entry, the department space 402 and the disease space 404 will become selectable. If, on the other hand, "per department" (the unit of department) is selected as the unit of variance entry, the department space 402 only will become selectable. Refer back to FIG. 41.

The management unit 56 receives the entry of variance factors (S234). In FIG. 42, predetermined information is entered in an evaluation space 408, a variance factor space 410 and an open-ended entry space 412. The same explanation made so far serves the purpose of describing these spaces and therefore the repeated description is omitted here. Refer back to FIG. 41. The recording unit 60 records items in units of variance entry set and the variance factors by associating them with each other (S236). For instance, in the case of FIG. 42, a variance factor is recorded by associating this variance factor with "necrosis is caused by peripheral circulatory disorder" as a nursing problem.

The variance factors recorded in the recording unit 60 undergo statistical processing and/or counting processing by the counting unit 58. Hereinbelow, an example of a processing result by the counting unit 58 will be depicted. Here, a case where the above-described unit of variance entry is set to "per problem" is exemplified. As shown in FIG. 42, the number of "negative" factors and the number of "positive" factors are counted in such a manner as to be associated with each item indicated in "problem". Here, "negative" and "positive" are results entered in the evaluation space 408 in FIG. 42. Though not shown in FIG. 43, the counting unit 58 may perform counting on each item indicated in the variance factor space 410 of FIG. 42. FIG. 44 shows still another counting result recorded in the counting unit 58. The counting unit 58 enumerates the comments entered in the open-ended entry space 412, in a list format.

Hereinbelow, a modification will be described. In the above-described embodiments, nursing problems are set in the problem preparation supporting unit 30, and the management unit 56 receives variance factors by associating them with the nursing problems set. In this modification, suppose that another nursing problem occurs in a situation where the nursing care is implemented along with the nursing care plan corresponding to a nursing problem after the nursing problem has been set. Then, the management unit 56 receives variance factors corresponding to nursing problems other than the nursing problems which have already been set in the problem preparation supporting unit 30 and the plan preparation supporting unit 34. An interface at the time of receiving the variance factors is one as shown in FIG. 42. And if the unit of variance entry is set as the unit of problem, a variance factor will be entered after a new item is selected, in the nursing problem space 406, from the department space 402.

By employing the above-described structure, the variance factors are entered by associating them with the nursing problems and the like, so that the variance factors can be managed per nursing problem and the like. Since a department, a disease and a nursing problem can be selected as the problems on a patient's disease, the management of variance factors according to need can be carried out. Since the unit to be associated with variance factors is set by an interface similar to that used in setting the nursing problems, the processing can be performed with ease. Since the variance factors can be verified in units of finer level such as department, disease and problem, the work necessary for improving and ensuring appropriate medical action can be supported efficiently. Since the variance factors can be verified in finer levels, the standard plan can be suitably updated. Since a problem and a plan therefor are selected from the standard plans which have been recorded beforehand, the setting of problems and plans can be set with ease. Even in the event that another nursing problem arises while the nursing care is being conducted, a variance factor associated with the another problem can be entered.

8. Others

Figure 45A:
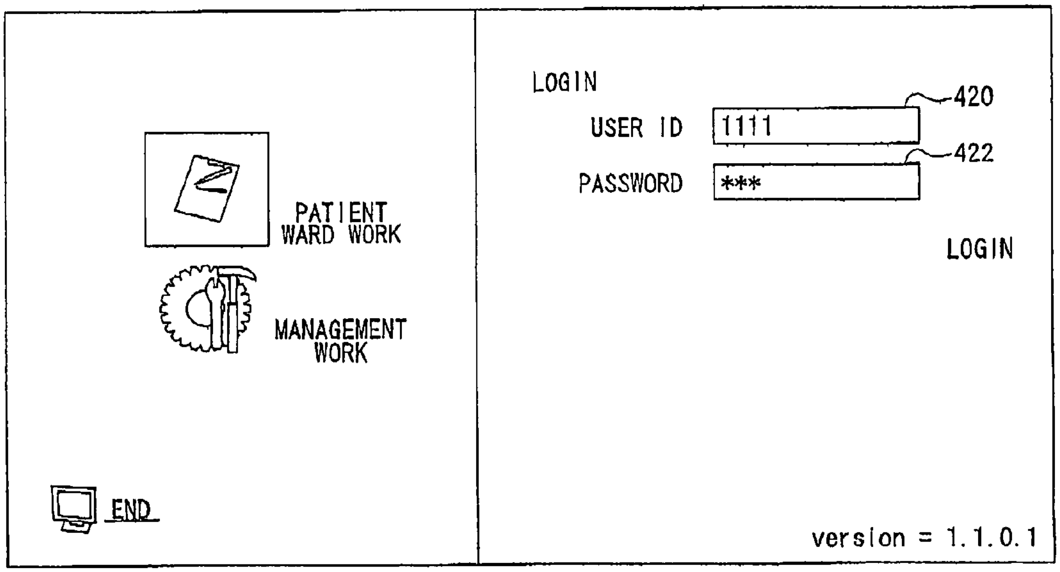
FIG. 45A illustrates an entry screen of nursing problems displayed on a display apparatus of FIG. 2.
Figure 45B:
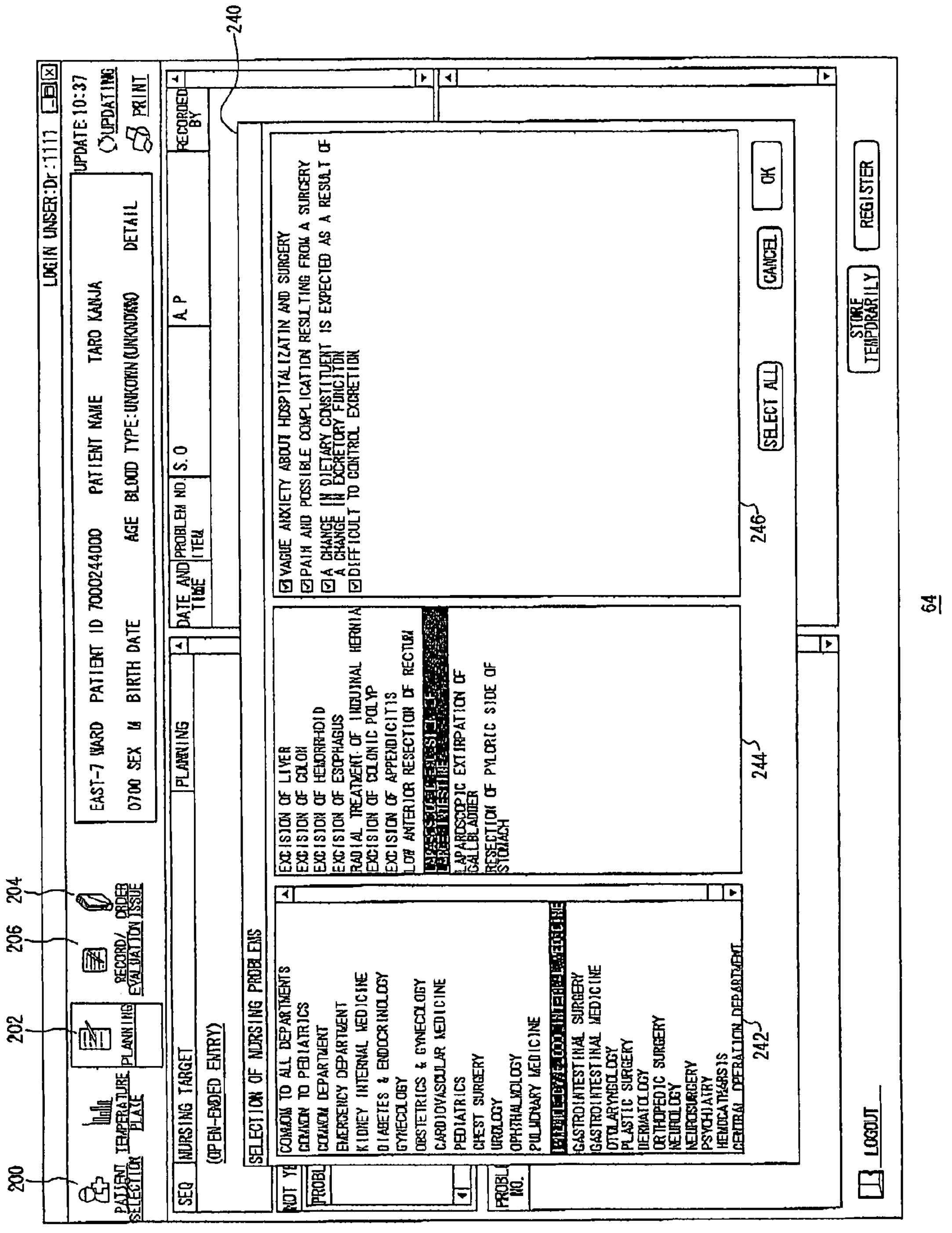
FIG. 45B illustrates an entry screen of nursing problems displayed on a display apparatus of FIG. 2.
Figure 45C:
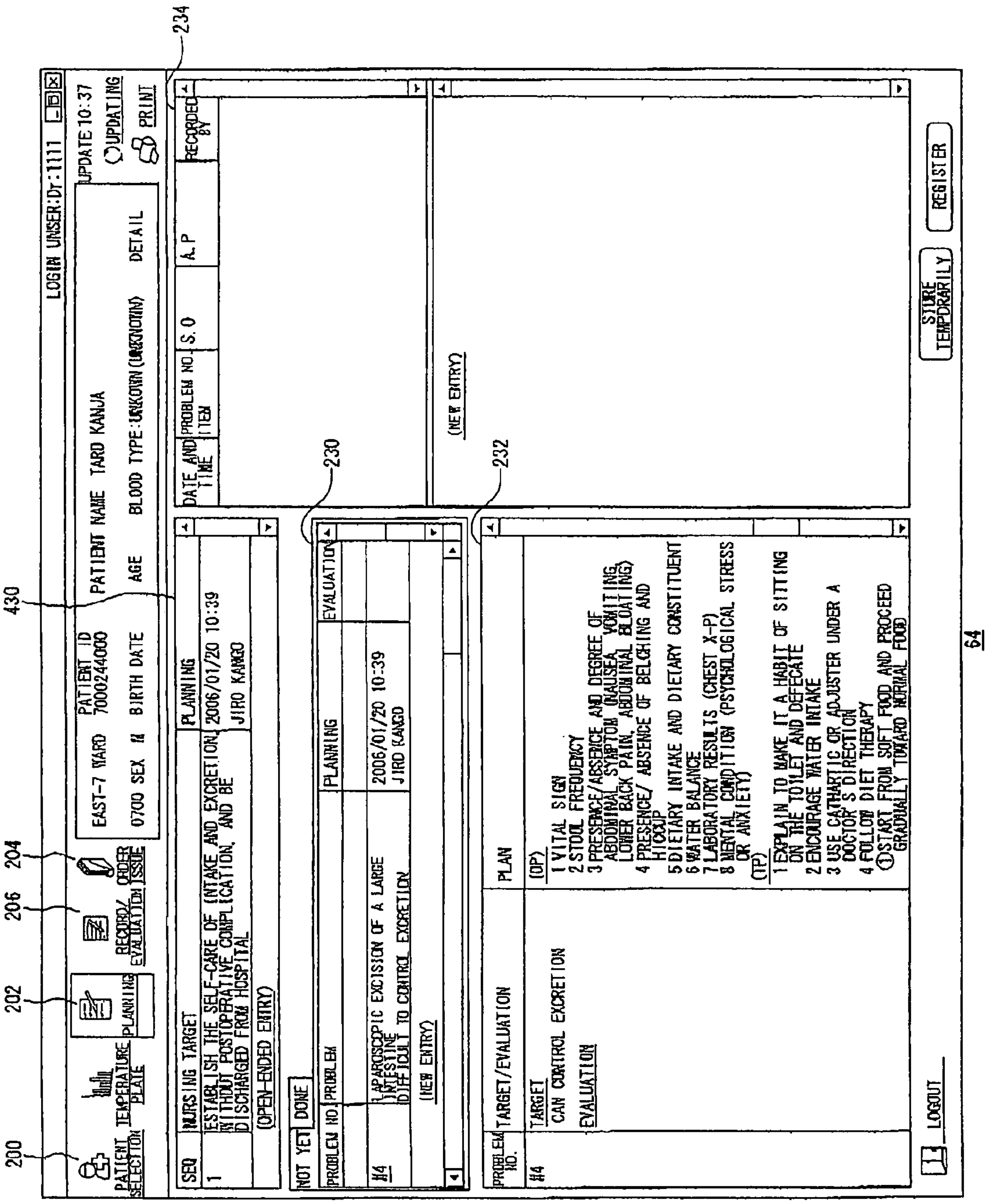
FIG. 45C illustrates an entry screen of nursing problems displayed on a display apparatus of FIG. 2.

A description will now be given of a detailed structure necessary to achieve a nursing information management system according to the present invention. Firstly, the control unit 42 performs the displaying of not only names of persons who are logged in but also information relating to their job descriptions. The control unit 42 displays not only nursing problems but also nursing targets. Here, the nursing target corresponds to a final purpose in conducting a nursing care throughout patient hospitalization. FIGS. 45A to 45C each illustrates an entry screen of nursing problems displayed on the display apparatus of FIG. 2. FIG. 45A illustrates a login screen to log into an application program run by the control unit 42. Here, the application program corresponds to an application program to operate the nursing information management system. A user ID space 420 and a password space 422 are displayed in FIG. 45A. A nurse or the like enters his/her user ID and password by operating the operation apparatus 62.

Similar to FIG. 12, FIG. 45B illustrates a screen for the selection of a nursing problem selection. A nursing problem selection window 240 is shown in FIG. 45B, and a department space 242, a disease space 244 and a nursing problem space 246 are displayed within the nursing problem selection window 240. Here, a user ID "1111" for a login user is displayed at an upper-right corner of the screen. Together with the login user ID "1111", "Dr" indicating the user's job description is also displayed. Note that, besides "Dr", "nurse" can be displayed as a job description. The control unit 42 stores beforehand a table in which the user IDs and the job descriptions are brought into correspondence with each other. A job description corresponding to a verified user ID is displayed on the display apparatus 64 by referring to the table.

FIG. 45C illustrates a screen obtained after a nursing problem has been entered in FIG. 45B. FIG. 45C corresponds to FIG. 13, and a nursing target is displayed in a nursing target space 430. The first database 32 stores also nursing targets by associating them with nursing purposes. The problem preparation supporting unit 30 selects a nursing target associated with the selected nursing purpose, and displays the selected nursing target in the nursing target space 430.

Next, a description will be given of the displaying of nursing problems. Identification numbers such as "#1" are assigned to the nursing problems in the order of their entries and are displayed on the display apparatus 64. In the nursing problems, problems not necessarily relating directly to a nursing care are also defined as common problems. Such common problems are assigned the ID numbers, such as "CP1", in the order of their entries. FIGS. 46A and 46B illustrates identification numbers of nursing problems displayed on the display apparatus 64. FIG. 46A shows the order in which the nursing problems are entered. As shown in FIG. 46A, the nursing problems are entered in the order of "#1", "#2", "CP1" and "#3". The common problem "CP1" is entered between the nursing problem "#2" and the nursing problem "#3". FIG. 46B illustrates an entry screen of the nursing problems obtained when the entry has been made as shown in FIG. 46A. In FIG. 46B, the common problem "CP1" is displayed above the nursing problem "#1". That is, the control unit 42 performs a control so that the common problem is displayed on top of the nursing problems regardless of the order in which the common problem was entered. Here, the displaying corresponds to the displaying in the nursing care plan space 232.

Figure 47A:
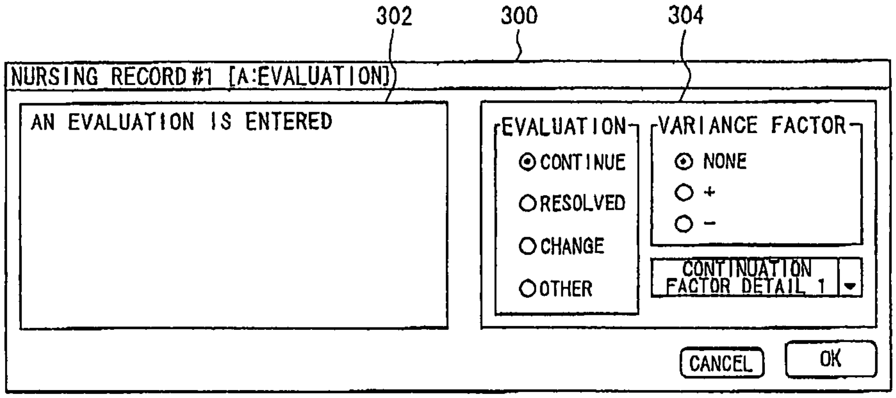
FIGS. 47A and 47B each illustrates an entry screen of a nursing record displayed on a display apparatus of FIG. 2.
Figure 47B:
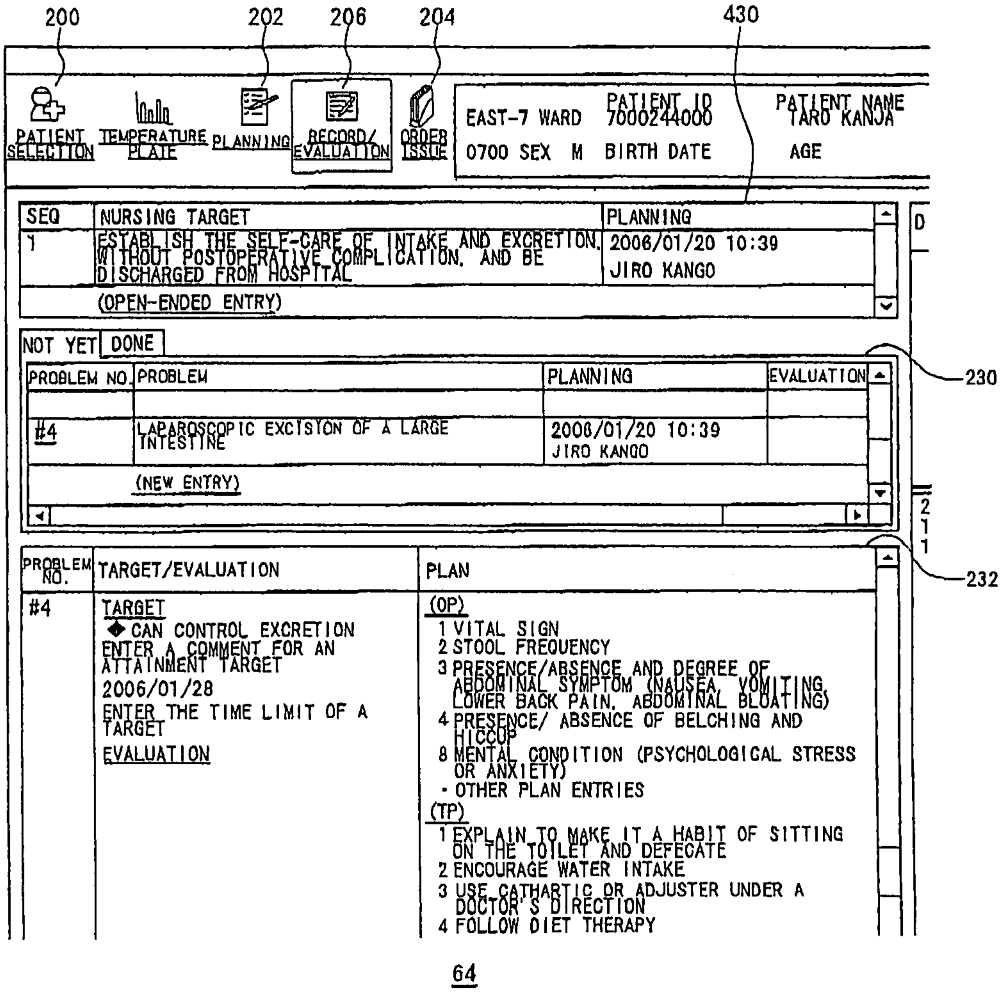

Next, a description will be given of relationships between the nursing problems and the variance factors. As described above, a variance factor corresponds to any discrepancy between an implementation result of a nursing care and a nursing care plan, and the nursing problems are often resolved when the variance factors are entered. Accordingly, if the fact that the nursing problems are resolved is explicitly indicated to the nursing problems to which the variance factors had been entered, the usability to the nurses increases. FIGS. 47A and 47B each illustrates an entry screen of a nursing record displayed on the display apparatus 64 of FIG. 2. FIG. 47A illustrates a screen at the time when a variance factor is entered. Similar to FIG. 35, an open-ended entry space 302 and an evaluation/variance factor space 304 are displayed within an evaluation information entry window 300 in FIG. 47A.

FIG. 47B illustrates an entry screen, on the display apparatus 64, obtained after a nursing evaluation and a variance factor have been entered. In a problem list space 230, "not yet" indicating that a nursing problem has not yet been resolved and "done" indicating that a nursing problem has been resolved are displayed in tabs. By selecting the respective tabs, resolved problems or unresolved problems are displayed in the problem list space 230. In so doing, when "resolved" is selected as an evaluation in FIG. 47A, the control unit 42 moves the nursing problem corresponding to the checked evaluation, to the problem list space 230 under the "done" tab. Note that the control unit 42 may perform a control such that no entry of variance factors is implemented unless the nursing problem becomes "done" in FIG. 47B.

A description will now be given of a case where a plurality of nursing problems correspond to a single nursing record. As a general rule, a single nursing record corresponds to a single nursing problem. However, there are cases where a single nursing record corresponds to a plurality of nursing problems. In such a case, if a plurality of identical nursing problems are displayed so that a single nursing record corresponds to a plurality of nursing problems, the contents thereof will be displayed in a complicated manner and therefore the convenience for nurses will be lost. Accordingly, the control unit 42 associates a plurality of nursing problems with a single nursing record. FIGS. 48A and 48B each illustrates an entry screen of a nursing problem in a display apparatus of FIG. 2. FIG. 48 A illustrates a nursing record space 234 when a nursing record corresponding to a single nursing problem has been set. Here, for instance, clicking on a right button of a mouse displays a nursing problem window 434 of FIG. 48A. Other nursing problems which have already been set are displayed within the nursing problem window 434. When one of the other nursing problems displayed on the nursing problem window 434 is selected, a selected nursing problem is displayed within the nursing record space 234 as shown in FIG. 48B.

Figure 49:
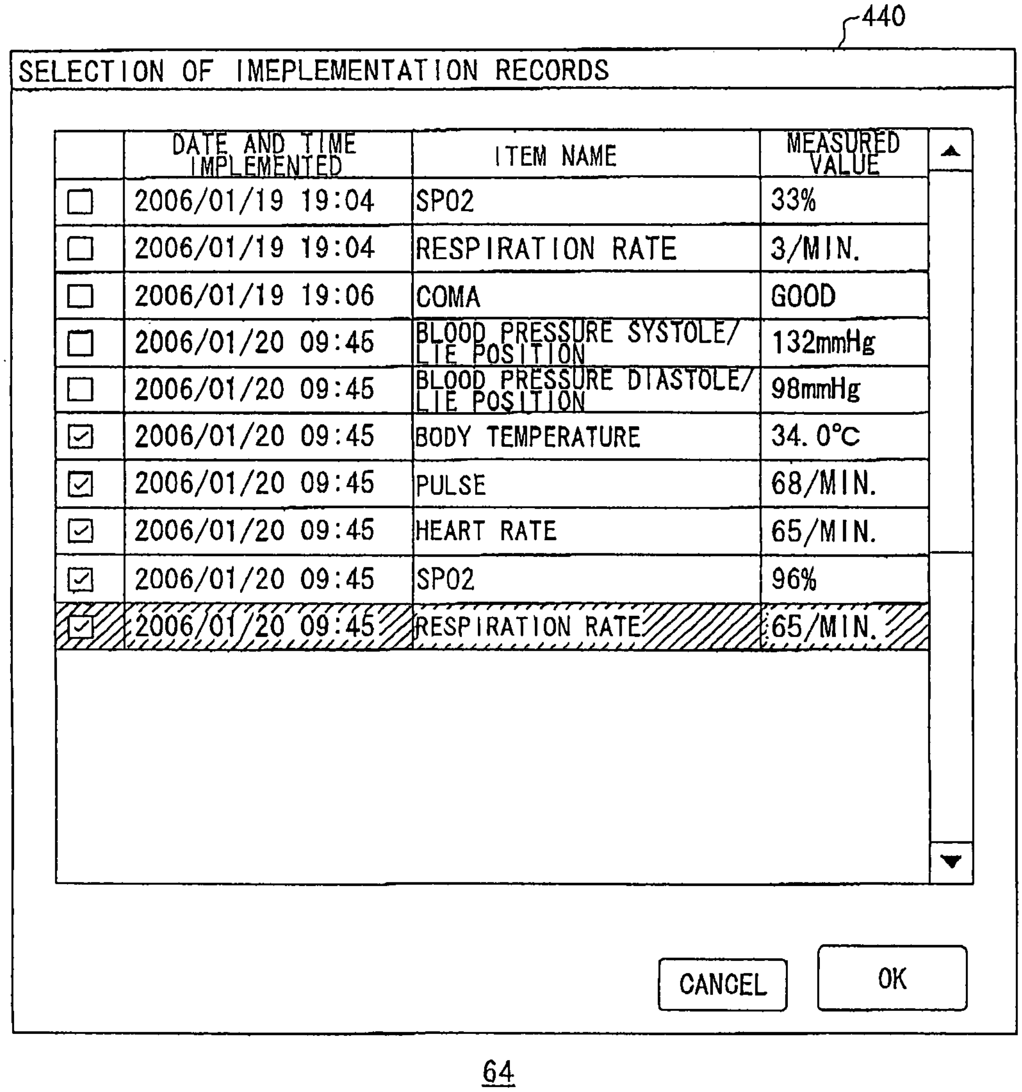
FIG. 49 illustrates a selection screen of an implementation record displayed on a display apparatus of FIG. 2.

Next, a description will be given of a case when a nursing record is sent to the PC 20 from the PDA 22. Although the nurse enters the nursing records into the PDA 22, the PC 20 generally does not require all of them to be recorded. FIG. 49 illustrates a selection screen of an implementation record displayed on the display apparatus 64. FIG. 49 corresponds to FIG. 28. An implementation record transmitted from the PDA 22 is recorded on the selection window 440 for implementation records. The management unit 56 selects an item to be recorded in the recording unit 60 if the nurse enters a check in implementation record items using the operation apparatus 62. The management unit 56 records the selected items in the recording unit 60.

Figure 50:
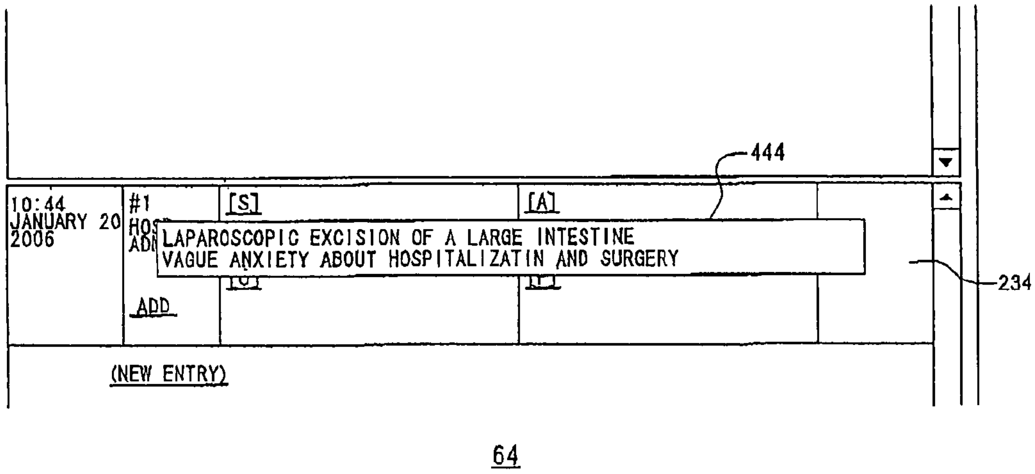
FIG. 50 illustrates an entry screen of evaluation information displayed on a display apparatus of FIG. 2.

Next, a description will be given of a relationship between a nursing record and a nursing problem. The nursing records and the nursing problems are brought into correspondence with each other. On the display apparatus 64, the nursing problems are displayed in the problem list space 230 and the nursing records are displayed on the nursing record space 234. It is preferable that when the nurse verifies a nursing record, nursing problems can be understood without the nurse's verifying or referring to the problem list space 230. FIG. 50 illustrates an entry screen of evaluation information displayed on the display apparatus 64. When the nurse moves a pointer of the mouse onto the nursing record space 234 using the operation apparatus 62 while verifying a nursing record in the nursing record space 234, the control unit 42 displays a nursing problem window 444 on the nursing recording space 234. A nursing problem corresponding to the nursing record is displayed on the nursing problem window 444. By verifying the contents displayed on the nursing problem window 444, the nurse can understand the nursing problem without verifying or referring to the problem space 230.

Next, a description will be given of what a nurse operates in the operation apparatus 62. As obvious from what has been described so far, in the nursing information management system in the PC 20 the nurse viewing the screen displayed on the display apparatus 64 enters a specification using a mouse as the operation apparatus 62. Here, an interface to enhance the operability in entering a specification is described. FIGS. 51A and 51B each illustrates a display screen for issuing orders in the display apparatus 64 of FIG. 2. FIG. 51A is a screen in a case when the order issuing button 204 is selected. One of a plurality of items displayed in an unimplemented-order stop space 450 is already selected by the pointer of the mouse. When a subsequent selection button 452 is selected, the control unit 42 selects also all the items subsequent to the already selected items.

Similar to FIG. 51A, FIG. 51B illustrates a screen in a case when the order issuing button 204 is selected. FIG. 51B corresponds to a display screen obtained when a plurality of items in the unimplemented-order stop space are consecutively selected and then a subsequent release button 454 is selected. When the subsequent release button 454 is selected by the pointer of the mouse, the control unit 42 releases the selection of the selected subsequent items. With these operations, the selection of a plurality of items and the release of the selection thereof are done by the selection of the subsequent selection button 452 and the selection of the subsequent release button 454, respectively, so that these operations provide usability to the nurses.

Figure 52:
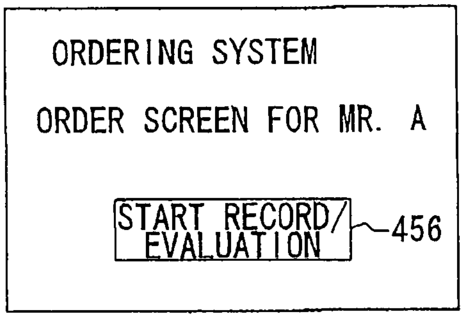
FIG. 52 illustrates a start screen of a nursing information management system in a PC of FIG. 1.

Next, a description will be given of an operation when the nursing information management system is started from a system other than the nursing information management system. Assume that the PC 20 starts a system other than the nursing information system, for example, an ordering system. There are cases where the starting of the nursing information management system is desired while the nurse starts the ordering system using the PC 20. In such a case, it is desired that the nursing information management system be started with ease and simplicity. FIG. 52 illustrates a start screen of the nursing information management system in the PC 20. Here, a screen for an ordering system is displayed on the display apparatus 64. When the nurse selects a record/evaluation start button 456 while using the operation apparatus 62, such screens as shown FIG. 35, FIG. 42 and the like are displayed on the display apparatus 64.

Figure 53:
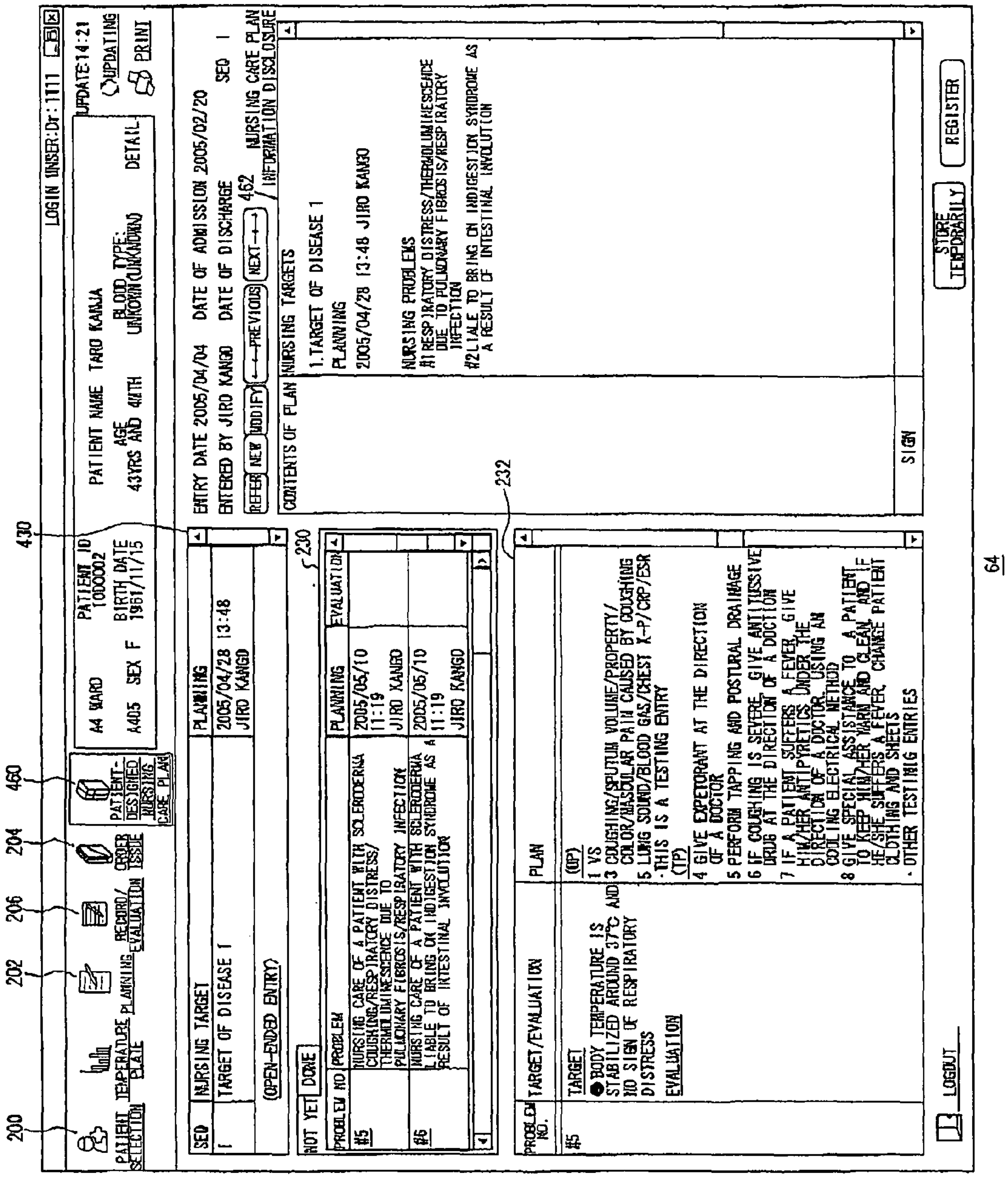
FIG. 53 illustrates a screen of nursing care plans, displayed on a display apparatus of FIG. 2, which is intended to shown to a patient.

Next, a description will be given of a screen used to explain the set nursing problems, nursing care plans and the like to a patient. FIG. 53 illustrates a screen of nursing care plans, displayed on the display apparatus 64, which is designed to be shown to a patient. A patient-designed nursing care plan button 460 is selected here. When the patient-designed nursing care plan button 460 is selected, the control unit 42 displays a nursing care plan information disclosure space 462 in the nursing record space 234 on the display apparatus 64. The control unit 42 displays the nursing targets, the nursing problems and the nursing care plans stored in the recording unit 60, on the nursing care plan information disclosure space 462 without modifying them. In so doing, the control unit 42 receives a specification to edit from a nurse via the operation apparatus 62, and changes the displayed contents of the nursing care plan information disclosure space 462 according to the specification to edit, Based on the contents displayed in the nursing care plan information disclosure space 462, a doctor and/or a nurse provide an explanation to a patient. The recording unit 60 stores any change made in the contents.

The present invention has been described based on the exemplary embodiments. These embodiments are merely exemplary, and it is understood by those skilled in the art that various modifications to the combination of each component and each process thereof are possible and that such modifications are also within the scope of the present invention.

In the embodiments of the present invention, the storage 48 stores predetermined conditions, and the selector 46 selects implementation results, satisfying the predetermined conditions, among the implementation results stored in the recording unit 60, and outputs their results to the viewing preparation unit 44. However, the present embodiments are not limited thereto and the selection of implementation results may be made manually. In such a case, the operation apparatus 62 receives from a nurse a specification about the listing of implementation results to be displayed in an area occupying a part of the screen, and performs a selection processing for selecting implementation results on the implementation results recorded in the recording unit 60, using the received specification as the predetermined conditions. This corresponds to a process where the implementation results to be selected are checked in the implementation result window 280 as shown in FIG. 28 and the result thereof is displayed in the nursing record space 234. According to this modification, a nurse's individual notion regarding the implementation results to be displayed can be reflected. That is, it suffices as long as a necessary and appropriate implementation result is selected.

In the embodiments of the present invention, the problem preparation supporting unit 30 outputs the nursing codes corresponding to the selected nursing problems, to the plan preparation supporting unit 34. Then the plan preparation supporting unit 34 selects nursing care plans from the second database 36, based on the nursing problem codes. However, the present embodiments are not limited thereto and, for instance, the problem preparation supporting unit 30 may output the selected nursing problem items to the plan preparation supporting unit 34 and the plan preparation supporting unit 34 may select nursing care plans from the second database 36, based on the nursing problem items. Alternatively, in the problem preparation supporting unit 30 and the plan preparation supporting unit 34, all of the processings may be carried out using codes corresponding to the nursing care plan items (hereinafter referred to as "nursing care plan codes"). In such case, for example, the coding problem codes or nursing care plan codes are converted into messages in the viewing preparation unit 44. According to this modification, the degree of freedom in the structure of the problem preparation supporting unit 30 and the plan preparation supporting unit 34 is improved. That is, it suffices if a nursing care plan corresponding to a nursing problem item is derived.

In the above-described embodiments of the present invention, a description has been given principally of a structure of the PC 20 but this structure may be provided for the server 12. In the present embodiments, the distinction between the PC 20 and the server 12 is made for convenience only, and it suffices if an apparatus connected to the PDA 22 has the above-described structure. According to this modification, the degree of freedom in the PC 20 and server 12 is improved.

While the preferred embodiments of the present invention have been described using specific terms, such description is for illustrative purposes only, and it is to be understood that changes and variations may be made without departing from the spirit or scope of the appended claims.

What is claimed is:

1. A nursing information management apparatus, comprising:

a processor configured to execute the following:

a setting unit which sets a plan on a medical action for a patient;

an implementation recording unit which records a content of an implementation of a nursing action conducted along with the plan set by the setting unit;

a discrepancy information input unit in which is defined a plurality of types of units affected by a data entry indicating a contributing factor to a discrepancy between the content of an implementation recorded by the implementation recording unit and the plan set by the setting unit, and in which is defined selectability of each entry unit available when the entry unit is selected, and which acknowledges information on a contributing factor to a discrepancy entered by an user according to the selectability associated with a selected entry unit;

a discrepancy information recording unit which records the information on a contributing factor to a discrepancy inputted by the discrepancy information input unit and the problem related to the patient's disease by associating the information on a contributing factor to a discrepancy and the problem related to the patient's disease; and a counting unit that counts the information on a contributing factor to a discrepancy recorded in the discrepancy information recording unit for each item indicated by the selectability associated with the entry unit, wherein the plurality of types of entry units includes a unit of hospitalization, a unit of department, a unit of disease, and a unit of problem, each with different selectability.

2. The nursing information management apparatus according to claim 1, wherein: the discrepancy information input unit cannot acknowledge information on a factor of discrepancy in the unit of department, in the unit of disease, and in the unit of problem when the unit of hospitalization is set; the discrepancy information input unit cannot acknowledge information on a factor of discrepancy in the unit of disease and in the unit of problem when the unit of department is set; and the discrepancy information input unit cannot acknowledge information on a factor of discrepancy in the unit of problem when the unit of disease is set.

3. A nursing information management apparatus, comprising:

a processor configured to execute the following:

a setting unit which sets a problem related to a patient's disease and a plan for the problem;

an implementation recording unit which records a content of an implementation of a nursing action conducted along with the plan set by the setting unit;

a discrepancy information input unit in which is defined a plurality of types of units affected by a data entry indicating a contributing factor to a discrepancy between the content of an implementation recorded by the implementation recording unit and the plan set by the setting unit, and in which is defined selectability of each entry unit available when the entry unit is selected, and which acknowledges information on a contributing factor to a discrepancy entered by an user according to the selectability associated with a selected entry unit;

a discrepancy information recording unit which records the information on a contributing factor to a discrepancy inputted by the discrepancy information input unit and the problem related to a patient's disease by associating the information on a contributing factor to a discrepancy and the problem related to the patient's disease, and a counting unit that counts the information on a contributing factor to a discrepancy recorded in the discrepancy information recording unit for each item indicated by the selectability associated with the entry unit, wherein the plurality of types of entry units includes a unit of hospitalization, a unit of department, a unit of disease, and a unit of problem, each with different selectability.

4. The nursing information management apparatus according to claim 3, wherein: the discrepancy information input unit cannot acknowledge information on a factor of discrepancy in the unit of department, in the unit of disease, and in the unit of problem when the unit of hospitalization is set; the discrepancy information input unit cannot acknowledge information on a factor of discrepancy in the unit of disease and in the unit of problem when the unit of department is set; and the discrepancy information input unit cannot acknowledge information on a factor of discrepancy in the unit of problem when the unit of disease is set.

5. A nursing information management apparatus according to claim 3, wherein the processor is further configured to execute the following:

a standard plan recording unit which records a standard problem for each patient's disease and a standard plan for each of the standard problems, wherein the setting unit selects a problem and a plan for a patient to be attended, from among standard problems and plans therefor recorded in the standard plan recording unit.

6. A nursing information management apparatus according to claim 3, wherein the processor is further configured to execute the following:

a standard plan recording unit which records a standard problem for each patient's disease and a standard plan for each of the standard problems, wherein the discrepancy information recording unit includes: a means which selects another problem than the problem set by the setting unit, from the standard problems recorded in the standard plan recording unit; and a means which inputs information on a factor of discrepancy between the content of an implementation recorded by the implementation recording unit and a standard plan corresponding to the another selected problem, by associating the information with the another selected problem.

7. A method for managing nursing information, comprising:

setting, using one or more computers, a plan on a medical action for a patient;

recording, using the one or more computers, a content of an implementation of a nursing action conducted along with the plan set by the setting;

acknowledging, using the one or more computers, where a plurality of types of units affected by a data entry indicating a contributing factor to a discrepancy between the content of an implementation recorded by the recording and the plan set by the setting are defined, and selectability of each entry unit available when the entry unit is selected is defined, information on a contributing factor to a discrepancy entered by an user according to the selectability associated with a selected entry unit;

recording, using the one or more computers, the information on a contributing factor to a discrepancy inputted by the inputting and the problem related to the patient's disease by associating the information on a contributing factor to a discrepancy and the problem related to the patient's disease; and counting, using the one or more computers, the information on a contributing factor to a discrepancy recorded, for each item indicated by the selectability associated with the entry unit, wherein the plurality of types of entry units includes a unit of hospitalization, a unit of department, a unit of disease, and a unit of problem, each with different selectability.

8. A method for managing nursing information, comprising:

setting, using one or more computers, a problem related to a patient's disease and a plan for the problem;

recording, using the one or more computers, a content of an implementation of a nursing action conducted along with the plan set by the setting;

acknowledging, using the one or more computers, where a plurality of types of units affected by a data entry indicating a contributing factor to a discrepancy between the content of an implementation recorded by the recording and the plan set by the setting are defined, and selectability of each entry unit available when the entry unit is selected is defined, the information on a contributing factor to a discrepancy entered by an user according to the selectability associated with a selected entry unit;

recording, using the one or more computers, the information on a contributing factor to a discrepancy inputted by the inputting and the problem related to a patient's disease by associating the information on a contributing factor to a discrepancy and the problem related to the patient's disease; and counting, using the one or more computers, the information on a contributing factor to a discrepancy recorded, for each item indicated by the selectability associated with the entry unit, wherein the plurality of types of entry units includes a unit of hospitalization, a unit of department, a unit of disease, and a unit of problem, each with different selectability.

9. A nursing information management method according to claim 8, wherein the setting selects a problem and a plan for a patient to be attended, from among standard problems and standard plans therefor recorded in the recording, by referring to a memory that has recorded the standard problem for each patient's disease and the standard plans for each of the standard problems.

10. A nursing information management method according to claim 8, wherein the inputting includes:

selecting another problem than the problem set by the setting, from recorded standard problems, by referring to a memory that has recorded the standard problem for each patient's disease and the standard plans for each of the standard problems; and inputting information on a factor of discrepancy between the content of an implementation recorded by the recording and a standard plan corresponding to the another selected problem, by associating the information with the another selected problem.

* * * * *